US005756304A

United States Patent [19]
Jovanovich

[11] Patent Number: 5,756,304
[45] Date of Patent: May 26, 1998

[54] SCREENING OF MICROORGANISMS FOR BIOREMEDIATION

[75] Inventor: Stevan B. Jovanovich, Livermore, Calif.

[73] Assignee: Molecular Solutions, Livermore, Calif.

[21] Appl. No.: 502,050

[22] Filed: Jul. 14, 1995

[51] Int. Cl.$^6$ .................. C12Q 1/04; C12Q 1/00; C12M 1/00; C12N 1/00

[52] U.S. Cl. .................. 435/34; 435/262; 435/4; 435/287; 435/252; 435/254.1; 435/800; 435/839; 435/832; 435/821; 436/43; 436/139; 422/50; 422/68.1; 588/251; 588/900

[58] Field of Search .................. 435/34, 262, 4, 435/287, 252, 821, 254.1, 800, 839, 832; 436/43, 139; 422/50, 68.1; 588/251, 900

[56] References Cited

U.S. PATENT DOCUMENTS

| | | | |
|---|---|---|---|
| 4,277,342 | 7/1981 | Hayes et al. | 435/262 |
| 4,468,461 | 8/1984 | Bopp | 435/262 |
| 4,522,723 | 6/1985 | Kauffman et al. | 435/262 |
| 4,789,478 | 12/1988 | Revis et al. | 435/262 |
| 4,859,594 | 8/1989 | Portier | 435/262 |
| 4,962,034 | 10/1990 | Khan | 435/262 |
| 4,973,970 | 11/1990 | Reeser | 435/262 |
| 4,984,594 | 1/1991 | Vinegar et al. | 435/262 |
| 5,059,252 | 10/1991 | Renfro, Jr. | 435/262 |
| 5,062,956 | 11/1991 | Lupton et al. | 435/262 |
| 5,080,782 | 1/1992 | Caplan et al. | 435/262 |
| 5,100,455 | 3/1992 | Pinckard et al. | 435/262 |
| 5,120,160 | 6/1992 | Schwengel | 435/262 |
| 5,133,625 | 7/1992 | Albergo et al. | 435/262 |
| 5,152,341 | 10/1992 | Kasevich | 435/262 |
| 5,155,042 | 10/1992 | Lupton et al. | 435/262 |
| 5,156,722 | 10/1992 | Snyder et al. | 435/262 |
| 5,158,595 | 10/1992 | Stillman | 435/262 |
| 5,160,525 | 11/1992 | Stillman et al. | 435/262 |
| 5,169,532 | 12/1992 | Whitlock | 435/262 |
| 5,183,541 | 2/1993 | Snyder et al. | 435/262 |
| 5,221,327 | 6/1993 | Rusin | 435/262 |
| 5,227,069 | 7/1993 | Van Dort et al. | 435/262 |
| 5,248,329 | 9/1993 | Rusin et al. | 435/262 |
| 5,263,795 | 11/1993 | Corey et al. | 435/262 |
| 5,265,674 | 11/1993 | Fredrickson et al. | 435/262 |
| 5,265,978 | 11/1993 | Losack et al. | 435/262 |
| 5,302,287 | 4/1994 | Losack | 435/262 |

OTHER PUBLICATIONS

Guyader et al; Ann. Biol. Clin.; vol. 49; pp. 301–307, 1991. Month not available.

Comprehensive Environmental Response, Compensation and Liability Act of 1980, PL–96–510 [CERCLA]and Superfund Amendments and Reauthorization Act of 1986 [PL 99–499]Month not available.

Toxic Substances Control Act of 1976 [PL 94–469]Month not available.

Solid Waste Disposal Act of 1965 [PL 89–272], Resource Conservation and Recovery Act of 1976 [PL 94–580]and Hazardous and Solid Waste Amendments of 1984 [PL 98–616]as amended in 1987, Month not available.

Federal Water Pollution Control Act of 1972 [PL 92–500], pp. 951–1017, Month not available.

Clean Water Act of 1977 [PL 95–217], pp. 4327–4339 as amended by the Water Quality Act of 1977 [Pl 100–4], as amended in 1990, Month not available.

Clean Air Act of 1970 [PL 91–604]and CAA Amendments of 1977 [PL 95–95]as amended in 1990 [PL 101–549], pp. 2399–2413, Month not available.

(List continued on next page.)

*Primary Examiner*—Louise Leary
*Attorney, Agent, or Firm*—Medlen & Carroll, LLP

[57] ABSTRACT

The present invention is directed to the application of robotics to screen and optimize microorganisms for their bioremediation capabilities. In particular, the present invention provides methods to screen for the ability of microorganisms to metabolize particular compounds of interest in bioremediation applications. The present invention also provides a method for discovery of microorganisms useful for bioremediation and biomining, as well as other applications where microbial metabolism is useful for catalyzing chemical biotransformations.

32 Claims, 16 Drawing Sheets

OTHER PUBLICATIONS

National Environmental Policy Act of 1969 [PL–588], Month not available.

Environmental Protection Agency, "Cleaning up the Nation's Waste Sites: Market and technology trends," pp. 1–7 [1993], Month not available.

U.S. Office of Technology Assessment, "Complex Cleanup: The Environmental Legacy of Nuclear Weapons Production," OTA–O–485, Month not available.

Day, S.M., "U.S. Environmental Regulations and Policies—Their Impact on the Commercial Development of Bioremediation," *Trends Biotechnol.*, 11:324–328 [1993], Month not available.

T.W. Federle et al., "Microbial Biomass, Activity, and Community Structure in Subsurface Soils," *Ground Water* 24:365–374 [1986], Month not available.

P.L. McCarty et al., "Trace Organics in Groundwater," *Environ. Sci. Technol.*, 15:40 [1981], Month not available.

G.W. Gee et al., "Recent Studies of Flow and Transport in the Vadose Zone," *Rev. of Geophys. Supplement.* pp. 227–239 [1991], Month not available.

S.G. Huling, and J. W. Weaver, "Ground Water Issue," U.S. EPA/540/4–91–002 pp. 1–21, [Mar. 1991], Month not available.

J.F. Tursman and D. J. Cork, "Subsurface Contaminant Bioremediation Engineering," *Crit. Rev. Environ. Control* 22:1–26. CRC Press [1992], Month not available.

C.D. Palmer and P. R. Wittbrodt, "Processes Affecting the Remediation of Chromium–Contaminated Sites," *Environ. Health Perspect.* 92:25–40 [1991], Month not available.

EPA/ORD, "Bioremediation of Hazardous Wastes," pp. 1–3, [1992], Month not available.

Colwell, R.R., "Scientific Foundation of Bioremediation and Gaps Remaining To Be Filled," 10th Forum Microbiol., pp. 40–41, (1992), Month not available.

Hamer, Geoffrey, "Bioremediation: A Response to Gross Environmental Abuse," *Trends Biotechnol.*, 11:317–319, [1993], Month not available.

J.A. Caplan., "The Worldwide Bioremediation Industry: Prospects for Profit," *Trends Biotechnol.*, 11:320–323, [1993], Month not available.

J.W. Blackburn and W.R. Hafker, "The Impact of Biochemistry, Bioavailability and Bioactivity on the Selection of Bioremediation Techniques," *Trends Biotechnol.*, 11:328–333, [1994], Month not available.

E.J. Bouwer and A. J.B. Zehnder. "Bioremediation of Organic Compounds—Putting Microbial Metabolism to Work." *Trends Biotechnol.*, 11:360–367, [1993], Month not available.

Committee on in situ Bioremediation, "In Situ Bioremediation. When does it work?," National Academy Press, Washington, D.C., pp. 33–45, [1993], Month not available.

Silver, S., "Exploiting Heavy Metal Resistance Systems in Bioremediation," *Bioremediation: Scientific And Technological Issues,* pp. 61–67, (1993), Month not available.

Olsen, R.H., et al., "Enumeration and Characterization of BTEX–Degrading Bacteria from Hypoxic Environments Functional with Mixed Acceptors," *Bioremediation: Scientific and Technological Issues,* 145:47–49, [1994], Month not available.

Cole, Jeff, "Controlling Environmental Nitrogen Through Microbial Metabolism," *Trends Biotechnol.*, 11:368–372, [1993], Month not available.

Broda, Paul, "Using Microorganisms for Bioremediation: The Barriers to Implementation," *Trends Biotechnol.*, vol. 10, pp. 304–304 (Sep. 1992), Month not available.

S. Liu and J.M. Suflita, "Ecology and Evolution of Microbial Populations for Bioremediation," *Trends Biotechnol.*, 11:344–351, [1993], Month not available.

G.M. Gadd and C. White, "Microbial Treatment of Metal Pollution—A Working Biotechnology?," *Trends Biotechnol.*, 11:353–359, [1993], Month not available.

H.F. Ridgway et al., "Identification and catabolic activity of well–derived gasoline–degrading bacteria from a contaminated aquifer," *Appl. Environ. Microbiol.*, 56:3565–3575, [1990], Month not available.

Stieber, Michael, et al., "A Rapid Screening Method for Micro–Organisms Degrading Polycyclic Aromatic Hydrocarbons in Microplates," *App. Microbiol. Biotechnol.*, 40:753–755, [1994], Month not available.

R. Boopathy and C.F. Kulpa, "Trinitrotoluene (TNT) as a sole nitrogen source for a sulfate–reducing bacterium *Desulfovibrio*sp (B strain) isolated from an anaeroic digester," *Curr. Microbiol.*, 25:235–241, [1992], Month not available.

R.G. Riley et al., "Chemical contamination on DOE lands and selection of contaminant mixtures for subsurface science research," U.S. DOE, Washington, D.C., [1992], Month not available.

D.Rai et al., "Environmental Chemistry of Chromium," *Sci. Total Environ.*, 86:15–23, [1989], Month not available.

R.H. Smillie et al., "Reduction of Chromium(VI) by Bacterially Produced Hydrogen Sulphide in a Marine Environment," *Water Res.*, 15:1351, [1981], Month not available.

DeLeo, P. and H.L. Ehrlich, "Reduction of Hexavalent Chromium by *Pseudomonas Flourscens*LB300 in Batch and Continuous Cultures," *Appl. Microbiol. Biotechnol.*, 40:756–759, [1994], Month not available.

R. Sims and J. Bass, "Review of In–Place Treatment techniques for Contaminated Surface Soils–Volume I. Technical Evaluation," EPA–540/2–84–003A, EPA, Cincinnati. [1984], Month not available.

Mischiati, Carlo; et al. "Use of an Automated Laboratory Workstation for Isolation of Genomic DNA Suitable for PCR and Allele–Specific Hybridization," *BioTechniques,* 15:146–151, [1993], Month not available.

Overview of an Experiment with a Growth Curve and Cr(VI) Assay.

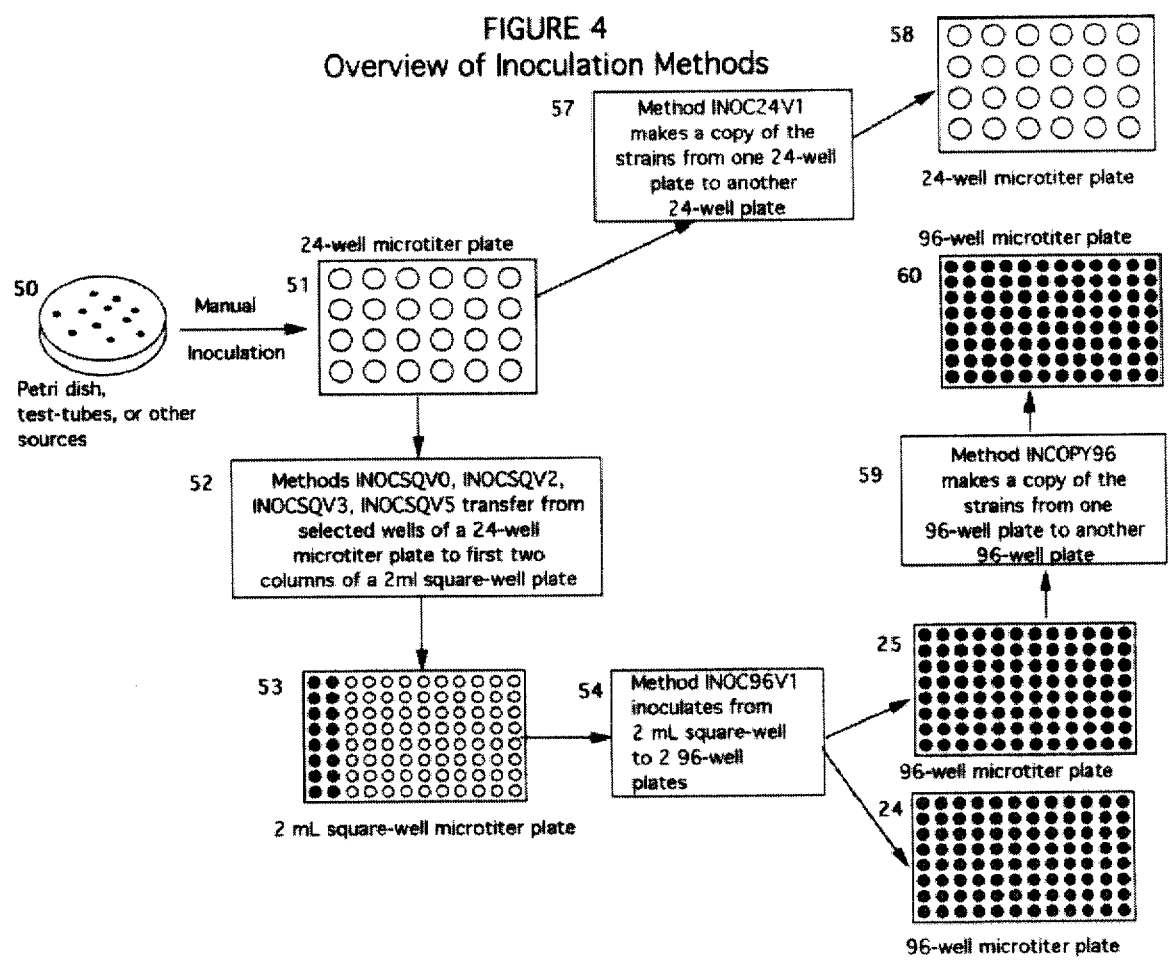

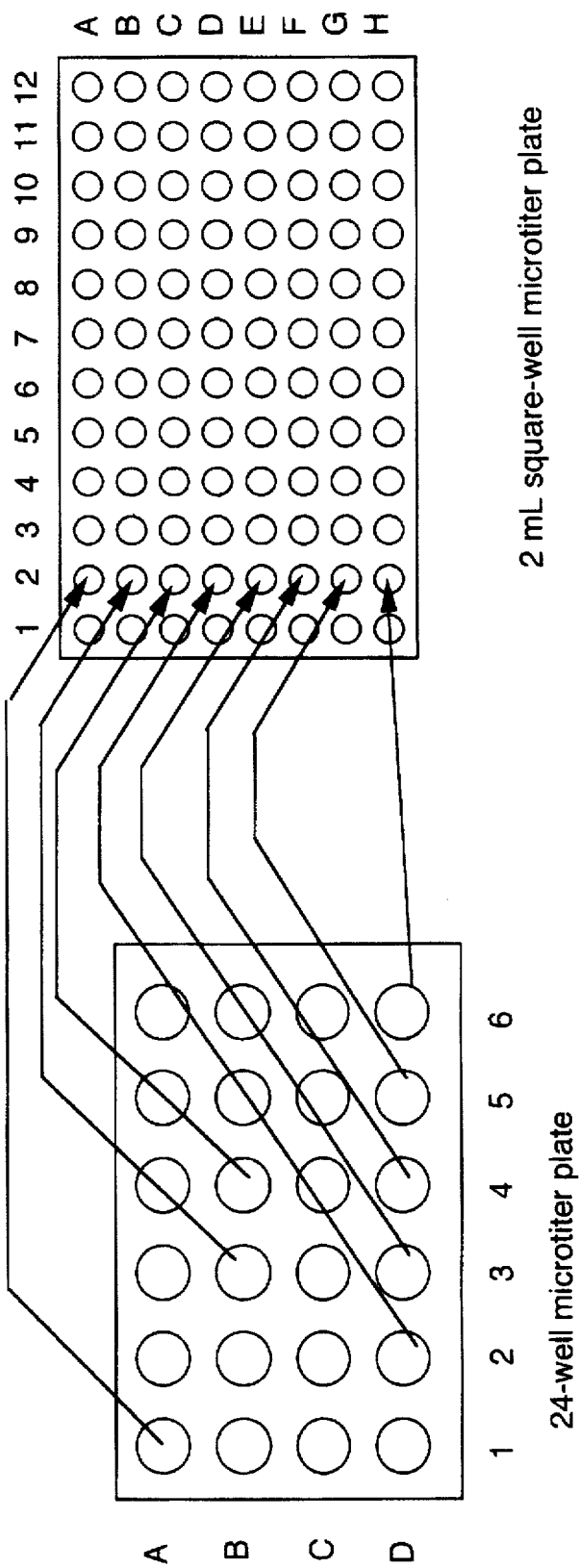

SCREENING OF MICROORGANISMS FOR BIOREMEDIATION

This invention was made with government support from Air Force grant FO8637 94 C6019. The government has certain rights in the invention.

FIELD OF THE INVENTION

The present invention is directed to the application of robotics to the screening of microorganisms for their bioremediation capabilities. In particular, the present invention provides methods to screen for the ability of microorganisms to metabolize, bind or biotransform particular compounds of interest in bioremediation applications. The present invention also provides methods for discovery of microorganisms useful for bioremediation and biomining, as well as other applications where microbial metabolism is useful for catalyzing biotransformations of chemicals.

BACKGROUND OF THE INVENTION

Over the past several decades, the impact of toxic materials released into the environment due to industrial and other activities has become increasingly recognized. Legislative action, resulting from public concern over these accumulating hazards, has mandated pollution control measures and environmental restoration of hazardous waste sites (e.g., "Super Fund" sites), as well as the prevention or reduction of pollution (see e.g., the Comprehensive Environmental Response, Compensation and Liability Act, PL-96-510 [CERCLA], and the Superfund Amendments and Reauthorization Act of 1986 [PL 99-499]; the Toxic Substances Control Act of 1976 [PL 94-469]; the Solid Waste Disposal Act of 1965 [PL 89-272], and Resource Conservation and Recovery Act of 1976 [PL 94-580] and the Hazardous and Solid Waste Amendments of 1984 [PL 98-616]; the Federal Water Pollution Control Act of 1972 [PL 92-500], Clean Water Act of 1977 [PL 95-217], and the Water Quality Act of 1977 [PL 100-4]; the Clean Air Act of 1970 [PL 91-604], CAA Amendments 217], and the Water Quality Act of 1977 [PL 100-4]; the Clean Air Act of 1970 [PL 91-604], CAA Amendments of 1977 [PL 95-95], and 1990 [PL 101-549]; and the National Environmental Policy Act of 1969 [PL-588]).

Not only is the release of toxic chemicals into the environment a significant safety concern, it represents a large economic impact. For example, the U.S. Government Accounting Office has estimated that the total remediation costs for the more than 3,000 inactive waste sites at eighteen Department of Energy (DOE) facilities has been estimated to be up to $90 billion (U.S. Government Accounting Office, "Nuclear waste problems associated with DOE's inactive waste sites," GAO/RCED-88-169 [1988]; U.S. Department of Energy, "Environment, safety and health needs of the U.S. Department of Energy, vol. I: Assessment of needs," DOE/EH-0079 [1988]). The Department of Defense needs are similarly staggering with an estimated clean-up cost of $24.5 billion for 7,313 sites (Environmental Protection Agency,"Cleaning up the nation's waste sites: Market and technology trends," [1993]). Private and industrial hazardous waste sites represent an additional burden on the environment and economics.

As the problems associated with hazardous waste sites are relatively recently recognized and many of the hazardous substances are not well-characterized, the technologies are also new and many are still in the developmental phase. Nonetheless, the national and world-wide commitment to restore damaged environments, minimize wastestreams, and more effectively manage hazardous wastes must involve new scientific technologies. However, the Office of Technology Assessment analysis of needed environmental restoration has concluded that the U.S. does not possess the technologies required for this specialized, yet multi-disciplinary field (U.S. Office of Technology Assessment, "Complex cleanup," OTA-O-485; see also, S. M. Day, Trends Biotechnol., 11:324-328 [1993]).

In general, contaminants in the environment are exposed to chemical and biological degradation. However, some contaminants are chemically stable. Therefore, intrinsic degradation is frequently dependent upon the biological activity of the indigenous microbial population. In most environments, a large variety of microorganisms is present at relatively high population densities. For example, in surface waters, microbial degradation of chemical contaminants is a major abatement mechanism, even when contaminants are present at very high concentrations. In subsurface ecosystems, microbial degradation rates of both natural and anthropogenic compounds are generally lower than comparable rates in soils or surface waters (T. W. Federle et al., Ground Water 24:365-374 [1986]). However, other researchers have concluded that naturally occurring biodegradation is still a major factor which influences the fate of organic contaminants in the subsurface (P. L. McCarty et al., Environ. Sci. Technol., 15:40 [1981]).

The various environmental conditions present in contaminated soils affect the microbial populations and the degradation rates. For example, subsurface microbes are typically present in an oligotrophic environment, with aeration conditions ranging from completely aerobic, to microaerophilic, to anoxic conditions. While aquifers are typically aerobic, anaerobic conditions can result from contamination with degradable organics. In addition, xenobiotic contaminants may not be substrates for the naturally occurring microorganisms present in a contaminated area, and may have extraordinarily long half-lives. Also, toxic metals cannot be degraded, but may undergo valence transformations that affect their toxicity and mobility. Toxic contaminants with long in situ half-lives, as well as metals, require active intervention before the contaminants harm the ecosystem. All of these factors present significant concerns in the restoration of hazardous waste sites to environmentally sound areas.

Hazardous Waste Site Restoration

Hazardous waste site restoration involves numerous stages including: preliminary assessment of environmental damage and response (i.e., "scoping"); remedial investigation, including site characterization and data gathering; development and analysis of alternative strategies; selection and approval of an appropriate remedial strategy; and application and support of the final remediation technology (40 Code of Federal Regulations 300.68(f)). Unfortunately, remediation efforts frequently face major barriers at the stage of "selection and approval Of an appropriate remedial strategy." Confounding factors include the presence of high contaminant concentrations, large volumes of contaminated areas, and localization problems resulting from subsurface heterogeneities and dynamics, and the lack of effective remediation technologies. Even in cases where remediation technologies are available, the associated length of time required to achieve safe conditions may be very long and the cost are frequently very high.

In the case of surface contamination, contaminants may be treated in situ with chemical, physical, or biological agents that convert them to innocuous forms. However, final contaminant levels must be reduced to legally acceptable and safe levels, and the resulting conversion products of these contaminants must be harmless. These multiple constraints have frequently precluded successful in situ remediation of surface contamination. Alternatively, the contaminated soil or water can be removed and treated ex situ in a decontamination facility with heat, chemicals, or biological systems. However, removal and treatment or disposal of such materials greatly increases the expense of remediation projects.

In addition to the difficulties encountered in surface remediation, the subsurface environment presents specialized challenges and potentially enormous volumes. Initially, as contaminants penetrate the vadose (i.e., unsaturated) zone by diffusion and transport, unsaturated soil may bind contaminants and retard their migration. Soil capillarity may cause lateral migration, while the preferred pathways facilitate the rapid solute transport of the contaminants to underlying aquifers (G. W. Gee et al., Rev. of Geophys. Supplement, pages 227-239 [1991]; U.S. Natl. Report to Intl. Union of Geodesy and Geophys.; and S. G. Huling, and J. W. Weaver, U.S. EPA/540/4-91-002 (Ground Water Issue), pp. 1-21 [March 1991]). Once in the aquifer, soluble leachates are transported with groundwater by advection to produce a plume with a possible increase in dispersion rate. The flow rate is governed by the hydraulic gradient and the permeability of the media.

Groundwater presents significant concerns. For example, groundwater retention times have been estimated to be from 200 to 10,000 years. Immiscible or slightly soluble contaminants present in groundwater may form free product either on the surface of the water table, or, for halogenated hydrocarbons, sink to form pools of dense nonaqueous phase liquid (DNAPL) (J. F. Tursman and D. J. Cork, Crit. Rev. Environ. Control 22:1-26. CRC Press [1992].). Chemical and biological processes of adsorption, volatilization, partitioning, phase separation, biodegradation or biotransformation, and soil structure complicate the situation, making it very difficult to predict the location and concentration of subsurface contaminants.

Currently, "pump-and-treat" methodologies are frequently applied to remediate subsurface groundwater contaminants with slow in situ chemical and biodegradative decay rates. Pump-and-treat can be effective in removing floating free product or in reducing high concentrations of soluble contaminants. For DNAPLs that pool in nonpermeable lenses, pump-and-treat must rely on the precise placement of extraction wells to remove the contaminant. In the case of contaminants that sorb to the subsurface matrix materials, after the initial removal of soluble contaminants in the groundwater, tailing can occur due to desorption, diffusion, or advection (C. D. Palmer and P. R. Wittbrodt, Environ. Health Perspect. 92:25-40 [1991]). Tailing can greatly increases the expense of pump-and-treat methods and greatly extends the time necessary (i.e., decades) to achieve legally acceptable concentrations of contaminants. According to an EPA study, "pump-and-treat technology alone is often insufficient to meet cleanup goals" (U.S. EPA, Office of Emergency and Remedial Response, "Evaluation of Ground Water Extraction Remedies: Phase II," Volume 1 [1991]). Rapid economical remediation of hazardous waste sites necessitates the development of more efficient ex situ treatment methodologies, improved in situ physical and chemical treatments, and enhanced in situ bioremediation processes.

Bioremediation

"Bioremediation," the use of microorganisms to detoxify hazardous contaminants, has been considered a promising method to provide economical and ecologically sound cleanup strategies (EPA/ORD, "Bioremediation of Hazardous Wastes," [1992]; see also, R. R. Colwell, Res. Microbiol., 145:40-41 [1994]; G. Hamer, Trends Biotechnol., 11:317-319 [1993], and J. A. Caplan, Trends Biotechnol., 11:320-323 [1993]). The U.S. Environmental Protection Agency (EPA) has classified bioremediation as one of the most promising and potentially economical innovative treatment technologies. Three major considerations in selection of the most appropriate strategy to implement bioremediation at a specific site include the amenability of the pollutant to biotransformation to less toxic products (i.e., biochemistry), the accessibility of the pollutant to microorganisms (i.e., bioavailability), and the optimization of biological activity (i.e., bioactivity) (see e.g., J. W. Blackburn and W. R. Hafker, Trends Biotechnol., 11:328-333 [1994]; and E. J. Bouwer and J. B. Zehnder, Trends Biotechnol., 11:360-367 [1993]).

The natural bioremediation catalytic processes minimize secondary waste and may significantly reduce restoration costs, particularly for the subsurface. As introduced above, bioremediation can be divided into ex situ and in situ procedures. Ex situ bioremediation can supply microbial catalysts for biodegradation or detoxification. For example, this method can be applied to supply the microorganisms and conditions for bioreactors for "pump-and-treat" operations, for soil farming, and for slurry phase reactors.

However, due to the associated removal, treatment, disposal, and transportation concerns, interest in in situ bioremediation has increased. This method represents one of the most cost effective, but still underdeveloped, new approaches to environmental restoration. In situ bioremediation is typically divided into two methods. The first method is termed "intrinsic bioremediation," "natural attenuation," "passive bioremediation," "bioattenuation," or "spontaneous bioremediation." In essence, this method involves monitoring the effectiveness of the natural microbial population in degrading or immobilizing contaminants at a site (Committee on in situ Bioremediation, "In situ Bioremediation. When does it work?," National Academy Press, Washington, D.C. [1993]).

The second approach is "enhanced bioremediation." In this method, the intrinsic microbial activities are increased through engineering. Some of the basic enhanced bioremediation approaches are comprised of: (1) physiologically augmenting the capabilities of indigenous microbial consortia ("augmentation"); (2) enhancing indigenous consortia by supplementing with more robust microorganisms with a higher avidity for the contaminant ("supplementation"); (3) use of biological products; (4) biotransforming or binding metals; (5) air sparging to maintain an aerobic environment; and (6) other means to increase the desired metabolic degradation of organics, or the immobilization, detoxification, or binding of metals.

Although bioremediation methods are relatively new and are still in development, microorganisms such as bacteria are increasingly being used to biodegrade gasoline and other organic contaminants. For metal contaminants which cannot be chemically degraded, microbial systems can biotransform toxic metal species to ones that are less toxic, immobilized, or are easier to recover. However, bioremediation accounts for only 21% of innovative technologies deployed at Superfund sites (EPA, "Cleaning Up the Nation's Waste Sites: Market and Technology Trends," [1993]). Bioremediation has been used 59 times on National Priority List (NPL) sites. In situ bioremediation has been used to treat 1.2 million cubic yards of soil at NPL sites, and ex situ bioremediation has treated an additional 700,000 cubic yards of the approximately 8 million cubic yards treated so far (EPA, "Cleaning Up the Nation's Waste Sites: Market and Technology Trends," EPA, Washington, D.C. [1993]). An additional 25.6 million yards of soil and sludge remains to be treated. Significant progress has been made in developing methods for bioremediation of certain specific contaminants, such as PCB's (poly-chlorinated biphenyls) (e.g., U.S. Pat. No. 5,227,069), petroleum (e.g., U.S. Pat. Nos. 5,160,525, and 5,059,252), heavy metals (e.g., U.S. Pat. Nos. 5,221,327, 5,248,329, 4,522,723, and 4,789,478; and S. Silver, Res. Microbiol., 145:61–67 [1994]), radioactive metals (e.g., U.S. Pat. Nos. 5,183,541, and 5,156,722), BTEX (e.g., R. H. Olsen et al., Res. Microbiol., 145:47–49 [1994]), nitrogen (see e.g., J. Cole, Trends Biotechnol., 11:368–372 [1993]), and chromium (e.g., U.S. Pat. Nos. 5,155,042, and 5,062,956).

Various techniques for bioremediation have been introduced, including methods for pumping (e.g., U.S. Pat. No. 5,080,782), slurry-based reactions (e.g., U.S. Pat. No. 5,232,596) injection (e.g., U.S. Pat. Nos. 5,133,625, 5,265,674, and 5,263,795), heating and vacuum (e.g., U.S. Pat. Nos. 4,984,594, and 5,265,978), improvements in soil compositions (e.g., U.S. Pat. Nos. 5,158,595, and 5,100,455), containment (e.g., U.S. Pat. Nos. 5,120,160, and 4,962,034), and mapping of contaminated sites (e.g., U.S. Pat. No. 4,973,970).

Unfortunately, effective bioremediation technologies are not currently available for most contaminants. Indeed, there are various barriers to widespread implementation of bioremediation, including the presence of complex mixtures of pollutants, concerns over the release of microorganisms into the environment, and issues related to large-scale methods (see e.g.,P. Broda, Trends Biotechnol., 10:303–304 [1992]). Thus, while the concept of bioremediation is attractive, the technology has only been applied in limited cases and must still be regarded as a emerging technology with great promise.

As bioremediation relies on microorganisms, microorganisms with suitable biochemical and physiological characteristics suitable for the task must be identified. Microorganisms are found in every ecological niche and are a major factor in geochemical cycles. The incredible diversity of microorganisms, and their role in geochemical cycling, has suggested that microorganisms may be found to remediate additional contaminants (see e.g., S. Liu and J. M. Suflita, Trends Biotechnol., 11:344–351 [1993]). Currently, microorganisms for bioremediation applications are typically identified by isolating strains or consortia from sites that have been heavily contaminated with a given pollutant. The microbial population isolated from the contaminated site can be enriched for degraders of the given pollutant in enrichment cultures, if the pollutant can be used as the sole source of a required nutrient (ie., a sole source of carbon, nitrogen, or sulfur, etc.).

Alternatively, strains or consortia isolated from contaminated sites or from laboratory culture collections can be screened for the desired bioremediation trait (i.e., degradation of an organic, or detoxification of a metal or radionuclide by binding, precipitation, or immobilization) (see e.g., G. M. Gadd and C. White, Trends Biotechnol., 11:353–359 [1993]). Various methods have been developed for screening such microorganisms. For pollutants where an isolated culture may contain all the metabolic machinery to transform the chemical, one method involves selection of the degrading organisms either on agar plates or in liquid enrichments containing the pollutant as the sole source of a nutrient, (i.e., carbon, nitrogen, sulfur etc.) (e.g., H. F. Ridgway et al., Appl. Environ. Microbiol., 56:3565–3575 [1990]). Other methods, using indicator plates or plate assays for either microbial growth, redox change, pH changes or other indicators signalling metabolism of the pollutant have been developed (e.g., M. Stiever et al., Appl. Microbiol. Technol., 40:753–755 [1994]). For consortia or isolated colonies (either from enrichments, selections, or screening plates), the effect of the microorganisms on the contaminants is typically quantified using liquid cultures and growth measured manually with a spectrophotometer or "Klett meter," and assaying for the concentration of pollutant either at intervals or at the end-point of the growth curve (e.g., R. Boopathy and C. F. Kulpa, Curr. Microbiol., 25:235–241 [1992]). This screening procedure is very labor intensive, and the number of strains that can be quantitatively analyzed is low. This screening is typically the first rate-limiting step in the discovery of the bioremediation capabilities of microorganisms. Thus, the efficiency of this method is less than optimal.

Following discovery of microorganisms that can biotransform a pollutant in laboratory conditions, the biotransformation rate can be optimized and a bioremediation process developed. This is accomplished by varying the physiological conditions and assaying for the effects on degradation or biotransformation of the pollutant. Again, this is a very labor intensive method and the number of strains that can be quantitatively analyzed is low. Following initial optimization and process development, the bioremediation process is tested in treatability experiments that more closely model actual site conditions. These can include column experiments or batch experiments, typically using either materials from the contaminated site or matrix materials and groundwater that model the site. This can also be very labor intensive and limit the number of conditions tested.

Overall, the methods currently available for selection of microorganisms suitable for use in bioremediation are very time-consuming, laborious, and not suitable to large-scale screening. To improve the rate of discovery and application of bioremediation technology, additional methods for the discovery of microorganisms with improved bioremediation characteristics for a wide range of contaminants must be developed and applied. In addition, a better approach to improve bioremediation rates at sites must be developed.

As mentioned above, effective bioremediation technologies are not currently available for most contaminants. More importantly, since toxic waste dumps, oils spills, landfills, etc. are so widespread, and current methods are so time consuming, there exists a great need for an expedited and reliable method in which to perform bioremediation. While there exist robotic systems which are able, under customized configuration by a user, to automate certain procedures, there currently exist none that are capable of screening microorganisms to develop bioremediation processes in a fast and reliable manner. Therefore, what is needed is an apparatus and method for providing a robotic system to automate a large scale screening for bioremediation processes.

SUMMARY OF THE INVENTION

This invention is an automated system and method to develop and optimize bioremediation processes. It includes a robot which is programmed to perform tasks which maximize effective measurements in bioremediation screening processes in a manner which generates reproducible results quickly and reliably.

The present invention comprises general methods for the use of robotics to systematically screen microorganisms for their bioremediation capabilities and to optimize those capabilities to develop processes for in situ bioremediation applications. It is contemplated that a wide range of microorganisms, both from culture collections and contaminated field sites (including subpopulations and consortia) will be screened for detoxification of one or more contaminants under multiple physiological conditions. It is then possible to investigate microorganisms with the best detoxification properties in more detail, in order to opitimize conditions and develop efficient bioremediation processes. The organisms screened and the data generated, can be used to create a library which includes the bioremediation capabilities of the strains (e.g., degradation rates, operating constraints, etc.), and their potential application to enhanced bioremediation. The use of robots facilitates rapid collection of data, as well as rapid deployment of the strains in the field for bioremediation and biomining applications.

There are three types of methods utilized by the robot in accordance with this invention. They include inoculation methods, utility methods, and assay methods. The inoculation methods are used on a growth media to transfer microorganisms to a test holder. The utility methods are used to transfer a chemical compound to the same test holder introducing the two elements. Finally, the assay methods are performed on the combined elements in the test holder. This invention provides these methods in a manner which provides a high throughput operation consistent with goals set forth above.

It is contemplated that microbial strains be isolated from contaminated sites and screened with the present invention. the overall approach is outlined in FIG. 20. The strains with the best characteristics are identified and compared with the strains in a library. Initial physiological conditions are then optimized, initially with the BioMek 1000 or other robotic systems, and adapted to site conditions or anticipated treatment conditions (i.e., in situ bioremediation, bioreactors or soil farming). After optimization, treatability studies modeling the site conditions are performed and the volumes scaled up. Finally, on-site pilot scale demonstration are used to test the applicability and economics of the developed system at the contaminated site.

Between process development and field application, laboratory treatability studies are contemplated. In the plan outlined in FIG. 20, the treatability experiments are combined with scale-up. These the treatability experiments follow the 96-well treatability experiments described above and use actual material from the field site (ie., contaminated soil and groundwater). Depending on the application, the treatability experiments may be conducted in various formats, including batch or flow-through experiments. For flow-through experiments, fractions are collected with a 96-well microtiter plate compatible fraction collector and the appropriate automated assay (ie., the Microscale Cr(VI) Assay™ for Cr(VI) detoxification or other 96-well assays for other contaminants), used to quantify and optimize the treatment process. The treatability experiments are used to verify that the bioremediation processes developed are applicable to the specific field sites, and to optimize the process.

One application of the robotic screening contemplated is to apply 96-well technology with a robot in order to develop 96-well treatability systems that model environmental conditions. The concept is to add slurries of different matrices, the contaminant of interest, and the strains being tested to 96-well microtiter plates in the presence or absence of growth media or other amendments. It is contemplated that the slurries be comprised of mixtures of ion exchange resins, fine-grained sand, silt, or clay, among other substances. Representative mixtures for different soil types are developed and then modified according to site characteristics. The representative mixtures are useful as a standard screening set that added to the bioremediation library for microbial strains screened in subsequent tests.

After these treatability studies are performed in the 96-well microtiter plate system, they are combined with physiological optimization systems. By combining these two systems, the impacts of physiological variables on site conditions can be modeled, optimized, and refined by the use of methods that are primarily automated. This helps insure that the solutions developed in the laboratory solve the problems presented by the particular site. Importantly, the information gathered may be customized to address the needs present in any field situation.

The approach of the present invention is generally applicable to many other contaminants, including organic compounds and semi-volatiles. For semi-volatiles, the use of aluminum sealing foil can prevent the evaporation of the compound(s), but at the expense of the growth rate data. Thus, use of the BioMek 1000 as a completely automated system, with no manual intervention, may limit applications of the technology to only colorimetric assays. However, other quantitative equipment, such as 96-well scintillation counters, fluorimeters, and phosphorimagers, are also available and are contemplated to be used in conjunction with the BioMek with 96-well microtiter plate technology, thereby extending the range of compound that can be assayed to any compound for which there is either a colorimetric, fluorimetric, or radioactive assay. The 96-well microtiter plate to be assayed is simply moved manually or by another robotic system to the 96-well scintillation counter, fluorimeters, or phosphorimager or other instrumentation.

In addition, through the use of different robotic systems, such as the Zymark series of robots with a three axis robotic arm, or other systems, many other types of growth containers can be used, such as anaerobic roll tubes or serum bottles, and almost any type of analysis can be interfaced and performed automatically, such as gas chromatography or high performance liquid chromatography, virtually extending capabilities to include a wide range of environment contaminants.

BRIEF DESCRIPTION OF THE FIGURES

FIG. 4 is a flow diagram of a basic inoculation procedure.

FIG. 23 is a pattern diagram of INOCSQV3.

GENERAL DESCRIPTION OF THE INVENTION

Figure 1:
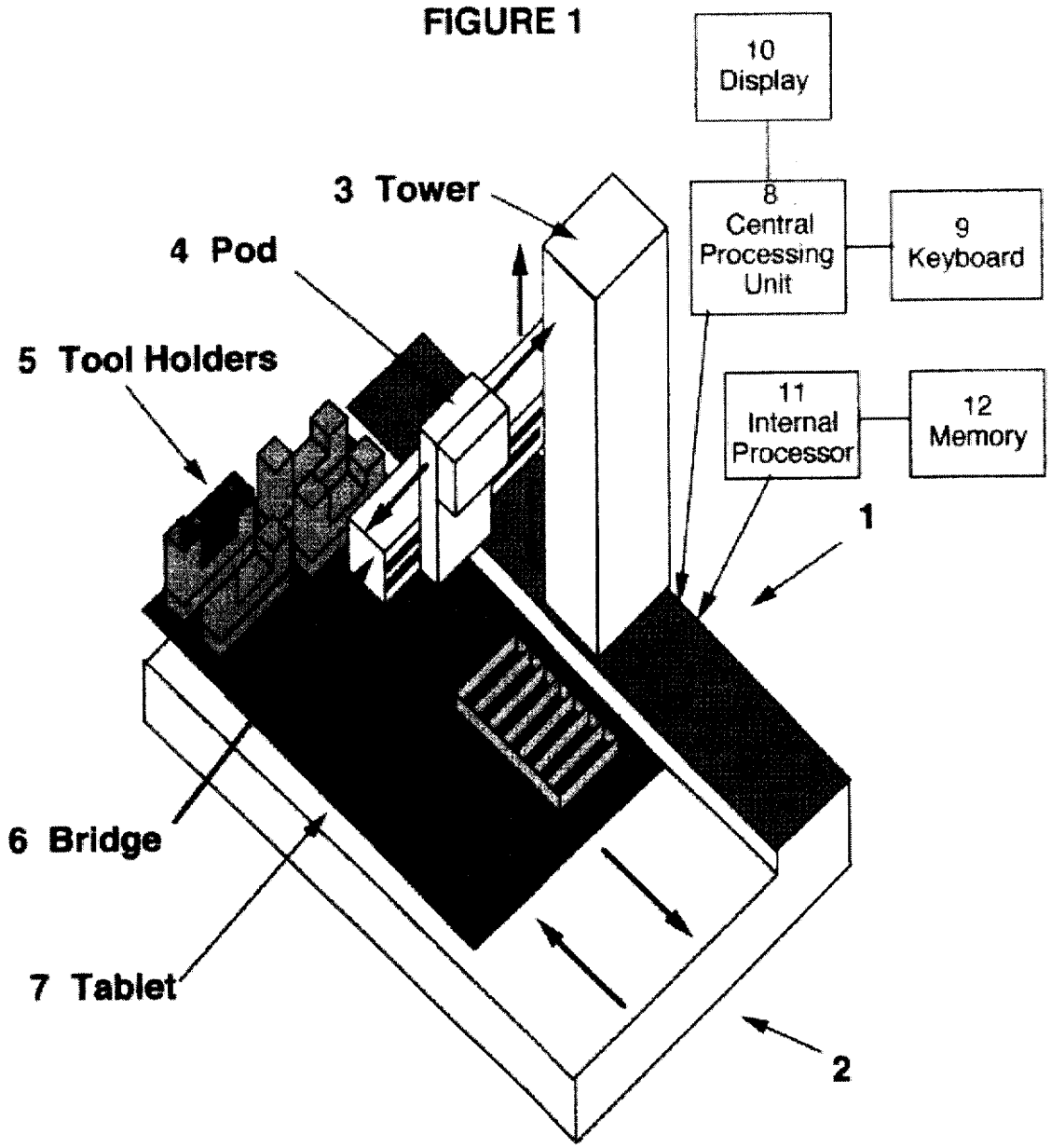
FIG. 1 is a perspective view of the Biomek 100 automated workstation

The present invention provides materials and methods needed to determine various microbial capabilities. The general approach is directly applicable to environment contaminants comprised of metals, radionuclides, volatile and non-volatile organics (comprised of hydrocarbons, halogenated hydrocarbons, polyaromatic hydrocarbons, and explosives), and mixed waste.

For example, the ability of microorganisms to act on metals may be assessed, including biotransformation from one valence state to another, binding, sequestering, or volatilizing metals and their derivatives, conversion to forms with altered mobilities, derivatization to form compounds and molecules with improved properties, such as reduced toxicity, metabolism into cellular material, and alteration of the properties of the contaminant or contaminant mixture to facilitate the application of other remediation technologies.

The ability of microorganisms to act on organics likewise may be assessed, including degradation (including mineralization of the organic compound), binding, sequestering, or volatilizing the compound and its derivatives, conversion to forms with altered mobilities, derivatization to form compounds and molecules with improved properties, such as reduced toxicity, metabolism into cellular material, and alteration of the properties of the contaminant or contaminant mixture to facilitate the application of other remediation technologies. Although the present invention is useful for situations involving single waste types (i.e., a metal or organic compound), the present invention is also useful with mixed wastes.

Organisms useful in the present invention include prokaryotes (e.g., eubacteria and archaebacteria), or eukaryotes (e.g., fungi). Various sources of organisms may be utilized, including natural isolates from contaminated or uncontaminated sites, organisms from culture collections, and organisms produced with technologies such as recombinant DNA manipulation, genetic manipulations, mutagenesis, or selection.

These organisms may be isolates grown in primary cultures or enriched for particular characteristics. The screening can include conditions that affect the organism, the contaminants or contaminant mixtures, or model environmental conditions. For example, such variables as growth media conditions and compositions, aeration state, mixtures of contaminants, matrix conditions (e.g., presence of soil and sediment types, sand, clays, groundwater composition, etc.), and concentrations and types of pollutants may be manipulated to optimize the screening procedures, or tailor them to certain conditions. Indeed, the screening for bioremediation abilities or traits can be comprised of any methods, such as those that measure the physiological state of the organism, including growth rate, health, viability, growth yields, spore formation, and other physiological parameters. In addition, factors related to the contaminant (e.g., phase, concentration, contaminant mixtures, valence state and location) may also be manipulated.

One contemplated embodiment of the screening strategy involves the use of three screens. The first screen uses target contaminants at a small number of concentrations to allow the maximal number of natural isolates to be screened. For $K_2Cr_2O_7$ in TSB, the use of 0, 50, 100, and 150 mg/l is contemplated. However, for other contaminants, other concentrations suitable for that contaminant, may be chosen. If single wells are used with a control and three concentrations of target contaminant, each 96-well microtiter plate will hold 24 strains and the BioMek 1000 could collect data in automatic mode, including growth curves, on 48 isolates per day. However, if growth curves are omitted from the initial screening, or other robotic systems are used, it is possible to screen a much larger number of isolates per day.

The second screen contemplated is used to confirm the first screen data and gather additional data, including higher concentration ranges of target contaminants. This screen also allows collection of growth curve information, in addition to the detoxification data. Natural isolates that pass the second screen may be identified by standard methods, including such methods as the Biolog™ system, fatty acid analysis, PCR-ribotyping, or other standard methods. This identification information is used to help define the range of conditions used in the physiological optimization.

The third screen contemplated is used to determine the rate constants for contaminants removal under both standard laboratory conditions and conditions that reflect the field site conditions. The third screening is used to lead into the optimization of the physiological conditions for field applications.

The screening can also be applied to intrinsic bioremediation by enumerating populations densities by most-probable number (MPN) methods both for total number of microorganisms and for microorganisms that degrade or affect a given pollutant, and by measuring the kinetic rates of effects on pollutants under in situ or other conditions.

For in situ applications, strains are isolated from contaminated sites and screened using the present invention, in order to identify the microorganisms responsible for biotransformations of contaminants. The optimal physiological conditions are then determined, and used to devise strategies to improve natural detoxification processes by nutritional amendment. In addition, the screening strategy can identify exogenous microorganisms with improved bioremediation traits. These strains can be added to contaminated sites to augment the natural population for in situ applications, or they may be used in bioreactors, treatment ponds, and other ex situ modes. Indeed, it is contemplated that the wide range of bioremediation processes that can be improved by the present invention will result in significant reductions in cleanup costs, and greatly extend the range of remediation problems that can solved by bioremediation. In addition, the approach can be used to monitor intrinsic bioremediation processes and optimize amendments to increase natural detoxification rates. A valuable result of the approach will be a greatly increased understanding of the microbial transformation of matter in the environment. It is also contemplated that the present invention will uncover novel detoxification systems that could directly applied or be subsequently improved with biotechnology.

The discovery of microorganisms with increased bioremediation capacities will have many direct applications. The application of the organisms may be in situ, ex situ, or in a controlled bioreactor environment. It is contemplated that various setting will be used, including ground, water, wastestreams, air, marine sediments, or in other environments. Because the robotic screening is a general approach to bioremediation, a number of application strategies are possible of the strains and conditions found by this approach are possible. Indeed, the flexibility of the present invention provides many advantages to bioremediation efforts, which have not been possible before.

For in situ subsurface applications, metals can be immobilized by several mechanisms, and/or organics can be degraded. For example, biological filters can be employed to capture or degrade contaminants during the advection of groundwater through the filter. For treatment of lagoons and waste streams, microorganisms that can bind or precipitate metals or degrade organics may be used and recovered by flocculation, settling, or other capture methods. As a process, in a treatment train, microbes can be used as the initial treatment stage, or after a pump-and-treat stage, in a biopolishing step, to achieve lower concentrations than are economically acceptable with chemical or physical methods and to continue to treat "tailing."

It is contemplated that bioreactors be used to treat waste streams from point sources before the toxic metals or organics spread in the environment. For municipal treatment facilities, wastewater may be polished with a final microbial treatment using microorganisms identified in the present invention. For ex situ applications, microorganisms can be grown in bioreactors with flowthrough of contaminated wastestream or groundwater in pump-and-treat operations, or used in soil farming, bioslurries, or other treatment modes. The concept also encompasses the use of the organisms to produce extracts that are in turn used for environmental remediation. The extracts may be directly used or encapsulated into various materials with selective permeability.

For metals, in situ bioremediation is a difficult challenge, since metals can only converted from one species to another, and cannot be degraded. While species conversion does not remove the contaminant, it can reduce the toxicity, solubility, or mobility to lessen the environmental damage. Microbes act as natural catalysts to alter local conditions by enzymatic redox reactions, cell surface absorption, or binding. Reduction can lead to precipitation and immobilization of toxic species. Absorption or binding also result in removal of contaminants from solution, their concentration, and immobilization. Coupled with subsurface recovery technologies, this facilitates recovery of the contaminants in a concentrated form.

It is contemplated that the further development and field implementation of the technological approach described in the present invention will increase the range of problems that can be solved by bioremediation processes, reduce environmental restorations costs, improve biomining processes, and lead to a widely applicable database of microbial capabilities for bioremediation applications. It is also contemplated that the present invention will be useful in settings other than bioremediation. For example, in other industrial applications, the microorganisms can be screened for enzymatic activity for transforming substrate chemicals to more valuable chemicals. In large-scale environmental engineering applications, even a relatively small increase in efficiency has significant economic benefit. Indeed, it is conceivable that the discovery process will identify microorganisms and conditions that result in order-of-magnitude increases.

DETAILED DESCRIPTION OF THE INVENTION

The present invention provides methods which utilize robotics to screen microorganisms for their bioremediation capabilities. Importantly, the present invention permits optimization of these capabilities for in situ or ex situ bioremediation. Of particular interest are such microbial capabilities as degradation of organics, resistance to pollutants, detoxification or removal by binding or bioabsorption of contaminants from solutions, and bioleaching of minerals.

The systematic screening can be performed either manually or with the assistance of technologies including multichannel pipettors, 96-well technologies, and robots. In one preferred embodiment, robots are used to screen microorganisms in order to discover new or more efficient microbial capabilities, as well as processes to bioremediate environmental contaminants. There are many advantages to use of robotic technology, including high-throughput, consistent and long-term performance, high reliability, cost effectiveness, and reduced errors. Thus, screening by robotics has an additional substantial advantage over existing manual methods, as they may be utilized under extreme or unusual physical and chemical conditions (ie., anaerobic, hyperbaric, reducing or oxidizing atmospheres, or when using toxic or hazardous chemicals, including radionuclides). In treating hazardous waste, such considerations are of great importance, as robotic systems are capable of working in extreme and hazardous conditions, where it is unsafe or impossible to use human workers.

The screening can utilize any appropriate analytical methods. These may be comprised of spectroscopic analyses (including colorimetric assays and measurements of biomass through optical density measurements), fluorimetry, electrophoretic methods, chromatography (including high-performance liquid chromatography (HPLC), FPLC, gas chromatography (GC), gas chromatography with mass spectroscopy (GC/MS)), atomic adsorption spectroscopy, induced coupled plasma, and assays using radioactive compounds and radionuclides.

In addition, the present invention provides for the rapid collection of data with robots, thereby facilitating rapid deployment of suitable microbial organisms in the field for bioremediation and biomining applications. The robotic screening provides a general solution to find the best sets of strains for actual site conditions. For in situ bioremediation, once the contaminant mixture and site conditions are characterized, a library can be created that can be indexed by the primary priority pollutant, and then cross-indexed by site environmental conditions and conditions tested. The best strains are then available for testing by the robot under conditions that simulate actual site conditions, including co-contaminant mixtures, to further identify the best organisms and conditions in the library for bioremediation applications at the particular site.

If site conditions, including chemistry and microbial ecology are known, the robot is useful for the identification of amendments needed to augment either the natural microbial flora or added strains for optimal efficiency. Environmental microbial isolates from a contaminated site may be screened and then related organisms looked up in the database. The knowledge of how related strains perform can be used to "leapfrog" to define initial operating parameters for environmental isolates. The robot can then be used to tune the operating parameters for specific site conditions and either the organism can be reintroduced or the site conditions can be amended to improve growth and detoxification.

The present invention utilizes a reverse screening method, in which a single target compound or panel of target compounds is screened against a wide variety of microorganisms, with the goal being the identification of microorganisms that degrade or detoxify the target compound(s) of interest. Thus, the reverse screening of the present invention screens for, rather than against, microorganisms. The reverse screening can also improve physiological conditions for enhanced bioremediation. Extensive screening is critical, as microorganisms with the best bioremediation activities for the specific application and site conditions should be used in the remediation process, in order to realize the full economic environmentally-effective potential of bioremediation. The application of microorganisms with higher efficiencies directly translates to lower remediation costs. In addition, the discovery of new or more efficient systems using the present invention will allow new bioremediation strategies to be applied to situations that are currently considered intractable to bioremediation.

Due to its importance as a common industrial pollutant and the availability of an EPA colorimetric method, hexavalent chromium (Cr(VI)) was used as a target contaminant in the development of the methods of the present invention. Chromium is an industrial metal that is widely used in the manufacture of alloys and refractories, leather tanning, electroplating, pigments, magnetic tape, and many other chemical products. An unfortunate consequence of its wide usage is that it is a common industrial pollutant. Chromium is the second most common metal pollutant at NPL sites and is found at 112 of the NPL sites without Records of Decisions ("Cleaning Up the Nation's Waste Sites: Market and Technology Trends," EPA, Washington, D.C.[1993]). It is also the second most common metal contaminant in groundwater and soils or sediments at DOE sites (R. G. Riley et al., "Chemical contamination on DOE lands and selection of contaminant mixtures for subsurface science research," U.S. DOE, Washington, D.C. [1992]).

Chromium is both carcinogenic and mutagenic with hexavalent chromium, Cr(VI), (e.g., chromate ion $[CrO_4]_2$), considered to be the active species. The oxidation states of chromium in the environment are Cr(III) and Cr(VI). Cr(VI) is a potent carcinogen, mutagenic, and highly mobile (e.g., C. D. Palmer and D. R. Wittbrodt, Environ. Health Perspect., 92:25–43 [1991]; and D. Rai et al., Sci. Total Environ., 86:15–23 [1989]). Indeed, Cr(VI) is toxic at levels of about 5 ppm (see, U.S. Pat. No. 5,155,042, herein incorporated by reference). Cr(VI) can be produced by dissolution of $K_2Cr_2O_7$. Cr(III) is the most stable species under reducing conditions, and is less soluble, mobile, and toxic compared to the Cr(VI) species (e.g., C. D. Palmer and D. R. Wittbrodt, Environ. Health Perspect., 92:25–43 [1991]; and D. Rai et al., Sci. Total Environ., 86:15–23 [1989]). Therefore, the reduction of Cr(VI) to Cr(III) can be environmentally beneficial. Cr(VI) is reduced to Cr(III) by a variety of natural chemical and biological processes (see e.g., R. H. Smillie et al., Water Res., 15:1351 [1981]; and DeLeo and H. L. Ehrlich, Appl. Microbiol. Biotechnol., 40:756–759 [1994]). Cr(VI) can be reduced to Cr(III) by Fe(II), which is found in hematite and biotite, and by sulfides, sulfite, and soil organic carbons. The oxidation of Cr(III) to Cr(VI) is limited in nature primarily to oxidation by manganese oxides and by oxygen. In addition to the soluble forms, Cr(III) is precipitated as $Cr(OH)_3$ by hydroxides in the environment (R. Sims and J. Bass, "Review of In-Place Treatment Techniques for Contaminated Surface Soils-Volume I. Technical Evaluation," EPA-540/2-84-003A, EPA, Cincinnati.[1984]) or with Fe(III), while Cr(VI) can form a variety of precipitates with lead, calcium, barium, and other cations, and adsorbs to soils (e.g., C. D. Palmer and D. R. Wittbrodt, Environ. Health Perspect., 92:25–43 [1991]; and D. Rai et al., Sci. Total Environ., 86:15–23 [1989]). The solid phases can be useful in immobilizing a chromium plume. However, for pump-and-treat, precipitates can create a recalcitrant situation due to leaching, as soluble chromium is removed. The combination of desorption and dissolution of solid phase reserves can cause tailing of pump-and-treat extractions with chromium levels still above legally required limits.

For studying bioremediation of hexavalent chrome by reduction to trivalent chrome, Cr(VI) concentrations can quantified by the EPA 7196 colorimetric assay adapted to the BioMek 1000 robot as described in the present invention. Binding assays for radionuclides using a 96-well liquid scintillation counter and a 96-well filtration device are also contemplated to supplement the colorimetric assays on the BioMek 1000. The approach was validated for the detoxification of Cr(VI) by screening and finding microorganisms with improved Cr(VI) bioremediation characteristics. Two assays were created and automated on the BioMek 1000, namely, a Microscale Cr(VI) Assay™, and a generally applicable microbial growth assay. BioMek software, microbial methods for 96-well microtiter plates, and data analysis methods were developed and applied to create a standardized set of screens that were used to screen 70 strains from the Biolog strain collection (Biolog, Inc., Hayward, Calif.), and strains from a chromium-contaminated site. Although the use of the BioMek 1000 has been described (see e.g., C. Mischiati et al., BioTechn., 15:146–151 [1993]), the present invention represents a novel application of the workstation.

Numerous robotic systems can be incorporated into the present invention, including track systems with a robot arm(s) such as the Tecan Robotic Assay Composer (Tecan, Research Triangle Park, N.C.), or a 3-axis robot arm, such as the Zymate Microplate Management System (Zymark Corp., Hopkinton, Mass.). The Tecan and Zymark systems have substantial advantages over the BioMek 1000, in terms of flexibility and the range of assays that can be implemented. However, the substantial cost of these systems presents an important consideration. Despite the limitations of the BioMek 1000, it provides a cost effective robotic system for the present invention. The limitations of the BioMek photometry systems can be addressed simply by manual intervention in moving plates to other quantitative devices, such as 96-well microtiter format fluorometers and liquid scintillation counters, multichannel capillary electrophoresis, and other equipment.

The preferred embodiment of the present invention incorporates the BioMek 1000 computer controlled robotic workstation as shown in FIG. 1. The computer is an IBM-compatible, such as a P/S2 Model 50 (IBM, Armonk, N.Y.) or more powerful IBM-compatible computers, running DOS 3.3 (Microsoft Corp., Redmond, Wash.) or a higher operating system. The BioMek 1000 is programmed on the IBM-compatible computer in Genesis operating software (Beckman Cat. No. 357503) software or other custom software that uses the BioMek 1000 Electronic Interface Unit (Beckman Instruments) to control the BioMek 1000 robot.

The Genesis operating software is a menu-driven system that can be programmed by the user to customize the operation of the BioMek 1000 robot. The basic unit of instruction that is used in the Genesis software is the function; examples of functions are transfer functions, such as Wel2Well, Aspirate, Mix, Generic, Copy; the photometry function, ODMEAS, and functions such as Loop, Next, Tip Change, Pause. Functions can be assembled into subroutines, that can be named and saved as separate modular units. Subroutines can in turn be assembled into methods; methods can be executed to perform a task. Methods can be named and saved as separate modular units. Utilities to edit subroutines and methods, manage files, create patterns, and change BioMek 1000 system parameters are also provided.

FIG. 1 illustrates a perspective view of the BioMek 1000 automated workstation which is utilized in the preferred embodiment of the present invention. The main body (1) of the workstation consists of a base unit (2) that has a tablet (7), an elevator tower (3), and can have an optional peristaltic pump (not shown). The elevator tower (3), which is centered on the back of the base unit (2), holds a bridge (6) that in turn holds a pod (4). The bridge (6) can move vertically on the elevator tower (3), and the pod (4) can move forward and back on the bridge (6). The pod (4) is used to grasp tools (not shown) from the tablet (7). The tablet (7) can move left and right, giving the workstation the ability to manipulate tools and liquids in three axes. The tools can be a photometry tool—(Beckman Instruments, Cat. No. 373421), which holds 4 bandpass filters at a time from a choice of 9 bandpass filters in the range of 340 to 690 nm.; the P20 tool (Beckman Instruments, Cat. No. 373090), a single-channel pipettor for volumes up to 20 µl; the MP20 tool (Beckman Instruments, Cat. No. 373249), an 8-channel pipettor for volumes up to 20 µl; the P200 tool (Beckman Instruments, Cat. No. 373092) a single-channel pipettor for volumes up to 200 µl; the MP200 tool (Beckman Instruments, Cat. No. 373096), an 8-channel pipettor for volumes up to 200 µl; the P1000 tool (Beckman Instruments, Cat. No. 373093), a single-channel pipettor for volumes up to 1000 µl; the single-tip bulk dispense tool (Beckman Instruments, Cat. No. 373094) that can dispense from a bulk reservoir and evacuate liquid from labware with a vacuum line; and the eight-tip bulk dispense tool (Beckman Instruments, Cat. No. 373095), an 8-channel tool that can dispense 8-channels at a time from a bulk reservoir and evacuate liquid from labware with a vacuum line. An internal processor (11) coupled to memory (12) operates the functions of the Biomek and can be programmed by a user via an external central processing unit (8) such as a personal computer. A display (10) and Keyboard (9) is further coupled to the external processing unit (8) for user interface.

The BioMek can dispense large quantities of liquid with a bulk dispense tool, or accurately transfer volumes down to 1.5 µl, using single- and multi-channel pipette tools. All operations can be done sterilely. The photometry tool can quantify colorimetric assays and microbial growth. The four position tablet (7) can be flexibly arranged with test tubes, 96-well microtiter plates, Eppendorfs, and other containers depending on application.

Figure 2:
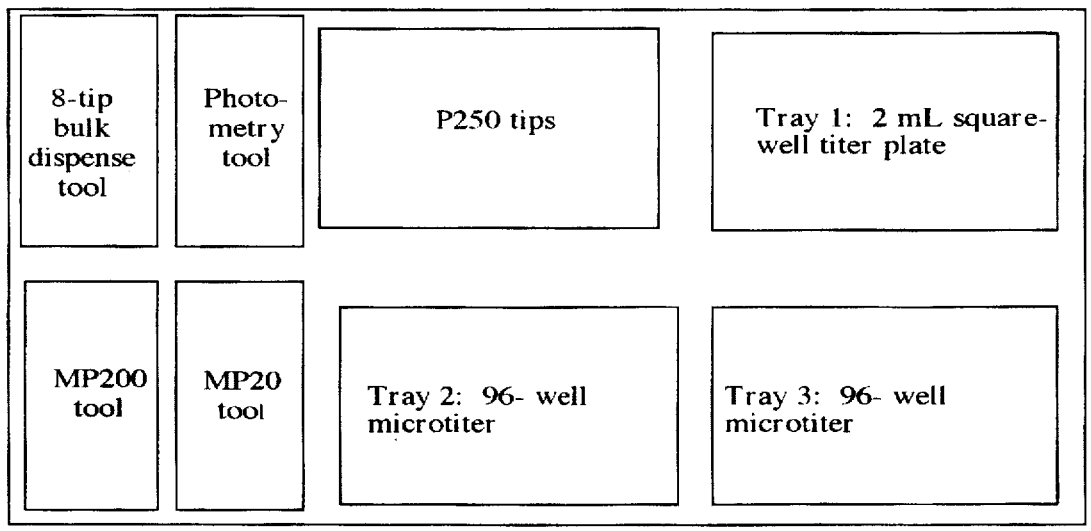
FIG. 2 is a standardized tablet layout for the BioMek 1000.

FIG. 2 shows one embodiment of a standardized tablet layout. In this embodiment, three 8-channel pipettors are used: the MP20, MP200, and 8-tip bulk dispense tools. The last tool position is occupied by the photometry tool. For the labware, there is one position for pipette tips and three trays. Trays 2 and 3 have 96-well microtiter plates (for example, Falcon 3075, Becton-Dickinson, Oxnard, Calif.) that are used to grow microorganisms and perform the Microscale Cr(VI) Assay™. Tray 1 contains a 2 ml square-well titer plate (Beckman Instruments, Cat. No. 140504) that is used for inoculation and to hold the Microscale Cr(VI) Assays™ reagents, and the tips used are the P250 tip rack assembly (Beckman Instruments, Cat. No. 372655) for the MP200 and MP20 tools.

The BioMek 1000 robot was used to develop a 96-well testing format in the present invention. One assay, the Microscale Cr(VI) Assay™, was used to determine the Cr(VI) bioremediation capabilities of numerous microorganisms. In addition, the Microscale Cr(VI) Assay™ can also be applied to monitor column fractions for treatability experiments and locate hot spots of Cr(VI) for site characterization. Due to the use of the robot, the Microscale Cr(VI) Assay™ represents a high-throughput method, capable of performing over 2,000 assays per day. The robot greatly enhances the testing capability of the system, providing an efficient, rapid, safe, and economical method for screening microorganisms for their ability to detoxify chromium.

Figure 3A:
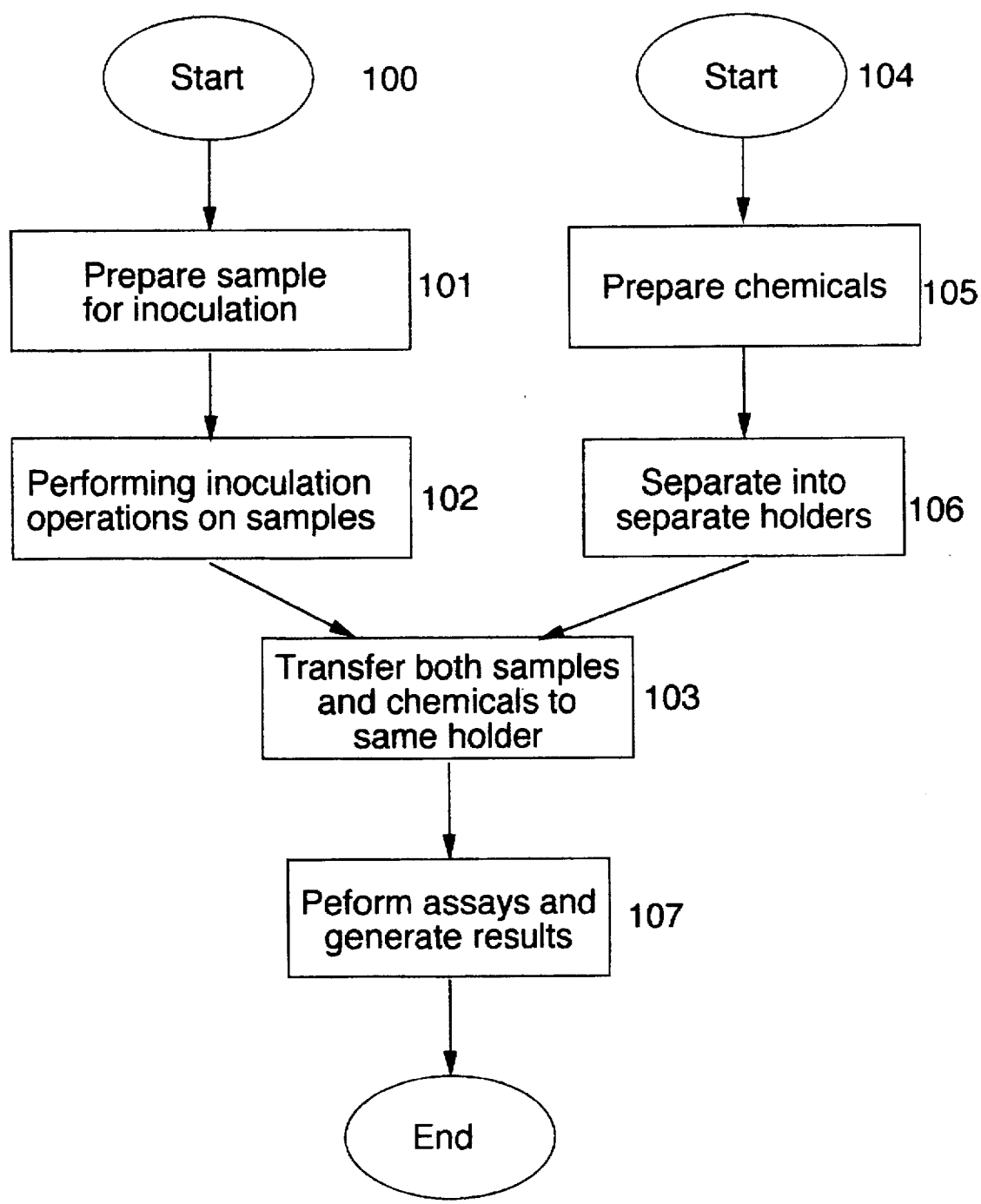
FIG. 3A is a general flow diagram of the methods of the present invention.

The operation of the BioMek 1000 is controlled by program methods. These methods fall into three categories, inoculation methods, utility methods, and assay methods. FIG. 3A illustrates a general flow diagram of the present invention. The process begins at start points 100 and 104. Samples containing microorganisms are first prepared and provided at block (101), then inoculation operations are performed on the microorganism samples at box (102) finally, the microorganism samples are transferred at block (103) to a final test holder. Following the start at point (104), samples containing chemicals are prepared and provided at box (105), then the samples are separated into different holders at box (106) before they are finally exposed to the microorganisms at box (103). Once the two are exposed to each other at box (107), assays are performed on the combination at box (107).

Figure 3B:
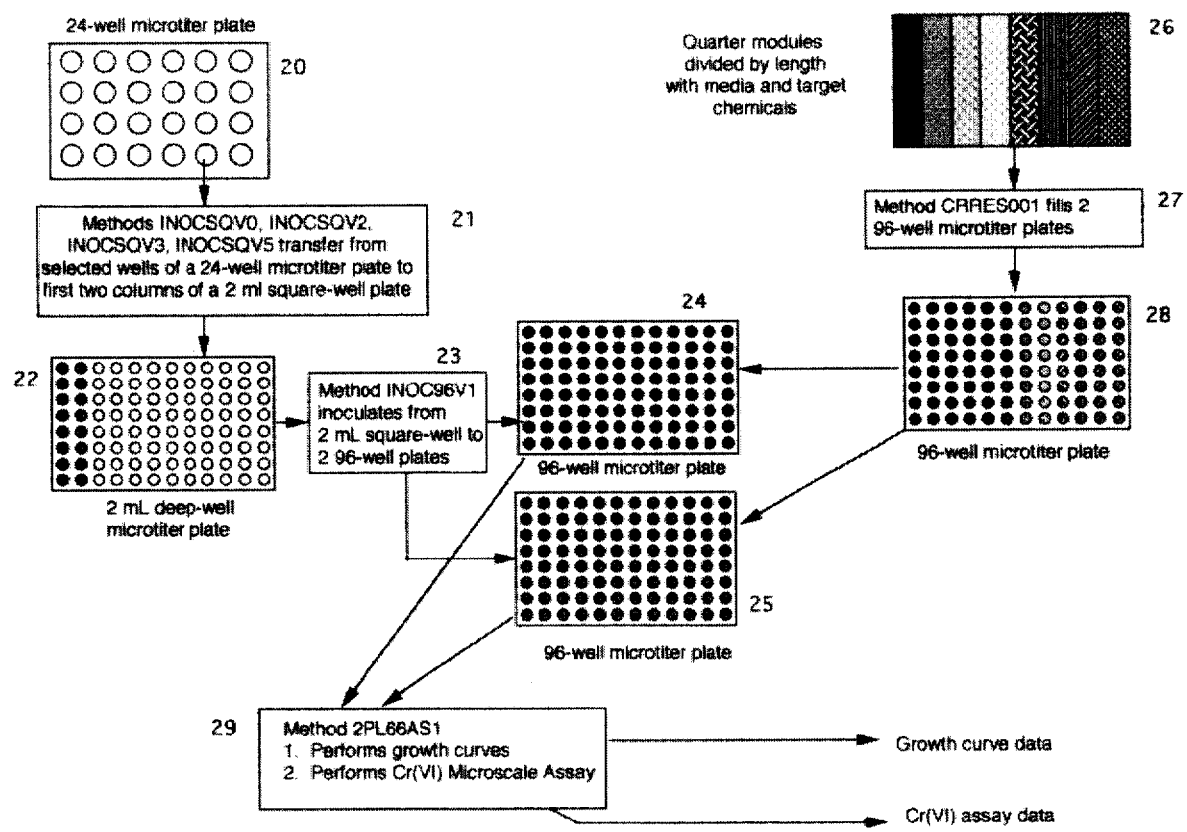
FIG. 3B is a specific flow diagram of a typical screening using the methods of the present invention.

FIG. 3B illustrates a more detailed flow diagram of a general screen incorporating the various methods. Samples inoculated from a source are transferred from a 24-well microtiter plate (20) to a 2 ml square-well microtiter plate (22) using one of the inoculation methods shown in box (21). (See the software section below for a more detailed description of the methods.) From plate (22), the samples are transferred to two 96-well microtiter plates (24) and (25) using the inoculation method INOC96V1. It is plates (24) and (25) which will serve as the testing site for the screening process. Quarter modules divided by length (26) are also provided which contain media and the target chemical, such as Cr(VI). The chemicals and media are transferred to final holders (24) and (25), which in the preferred embodiment are 96-well microtitre plates, using at least one of a plurality of utility methods (described below). The final holders (24) and (25) include vessels for holding the samples. In the preferred embodiment, the wells are square wells. Plate (28) and its shading, show the ordering of the samples as they are transferred from the modules (26) to the plates (24) and (25) according to utility method CRRES001. Once plates (24) and (25) have been exposed to the microorganisms and chemicals to form cultures, assay methods are performed to record the results. These assay methods perform such activities as recording growth curves, adding solutions and water to the cultures, and assaying Cr(VI) concentrations.

FIG. 4 illustrates a more detailed flow diagram of the inoculation methods discussed above. A source of microorganisms (50) such as a petri dish or test tube is used to manually inoculate a 24-well microtiter plate (51). The samples in plate (51) are then inoculated to a 2 ml square-well plate (53) according to one of the inoculation methods shown in block (52). (Again, further detail on all the methods is described in the software section below.) From the plate (53), the samples are inoculated to the two 96-well microtiter plates (24) and (25). Furthermore, a copy (58) of the plate (51) can be made by executing the inoculation method INOC24V1 shown in block (57). Still further, a copy (60) of a 96-well plate such as (24) or (25) can be made by executing inoculation method INCOPY96 as shown in block (59).

Figure 9:
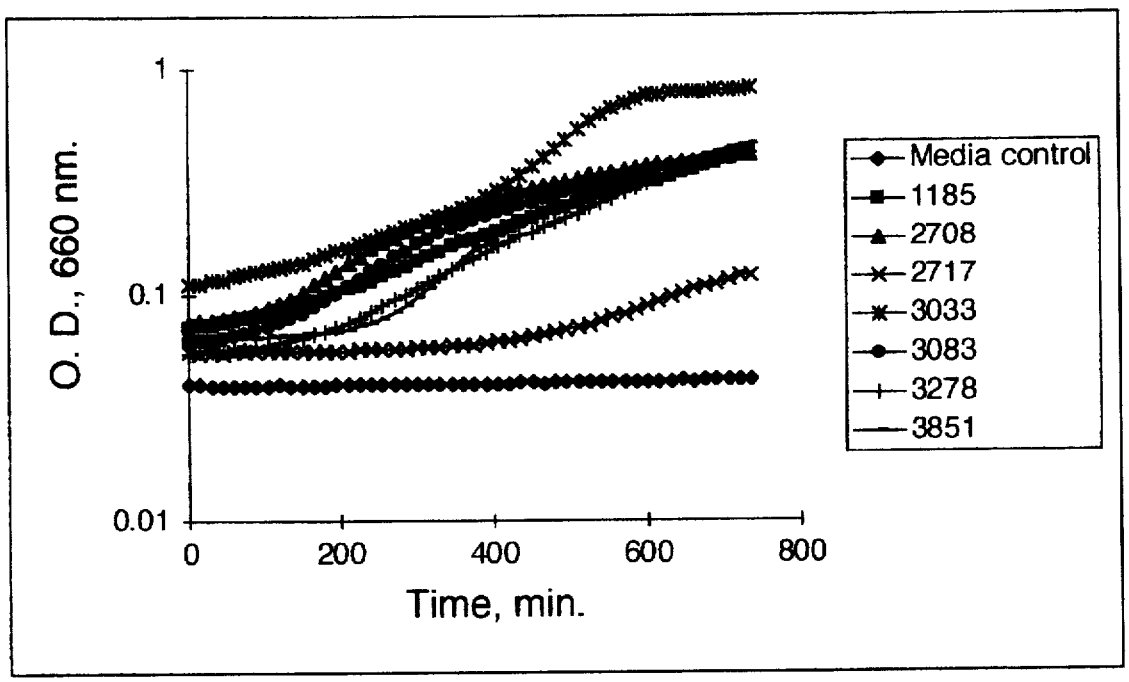
FIG. 9 shows growth curves for seven organisms.

A microbial growth assay was also developed, which uses a 96-well microtiter plate format and is automated on the BioMek (see e.g., the growth curves shown in FIG. 9.) The microbial growth assay performs a completely automated bacterial physiology growth curve of up to 192 strains or conditions at a time, while monitoring growth and controlling volumes. The microbial growth methods developed include automated strain transfer and inoculation methods, and semi-automated methods for data analysis, as described below. The microbial growth assay was combined with the Microscale Cr(VI) Assay™ to create a fully automated assay that determines the reduction or removal of Cr(VI) from solution and the effects on microbial growth. This combined assay was used either with an endpoint Cr(VI) assay as a screen or with multiple Cr(VI) assays to determine the kinetic rates of Cr(VI) reduction.

The applicability of the methods to potentially remediate field sites was demonstrated by screening 178 strains from a Cr(VI)-contaminated field site and isolating strains that remove Cr(VI). Initial physiological conditions were also defined for the removal of Cr(VI) from solution either by binding or reduction to Cr(III). In addition, semi-automated methods were developed to measure the kinetics of Cr(VI) removal. It is also contemplated that totally automated methods be used in the present invention. For example, the present invention may be used to measure the rate constants for Cr(VI) detoxification to optimize the bioremediation processes. In addition, a wide range of reaction volumes may be tested in the present invention, allowing successful for scale-up of the process.

SOFTWARE IMPLEMENTATION

As mentioned above, the robotics of the present invention provide specific program methods. These program methods, while directed toward the BioMek 1000 robot, are not intended to limit the scope of protection but rather are merely llustrative of a preferred embodiment of the present invention. A person skilled in the art will recognize that the present invention can be implemented with other types of robots systems. The methods described in detail below are adaptable to other robotic systems.

Here, as discussed above, the BioMek software methods are divided into three classifications: inoculation methods, assay methods, and utility methods. (See FIGS. 3A and 3B.) Different combinations of the methods listed below provides a high-throughput screening of the bioremediation capabilities of microorganisms for Cr(VI) detoxification using the BioMek robot. The examples provided below describe under what conditions the different combinations of methods are used. An appendix has been included with this application and includes a detailed, step by step description of the methods to assist in clarifying the different methods.

Again, methods that accomplish the same tasks can be similarly implemented on other robot systems. In addition, by replacing the Microscale Cr(VI) Assay™, with another assay for another contaminant, the methods can be directly extended to screen for detoxification of other contaminants.

Inoculation Methods

Inoculation of 96-well microtiter plates can be handled by a number of different automated methods, depending on the experiment or screening that is desired. (See elements 101–103 in FIG. 3A and elements 21 and 23 in FIG. 3B. It was rapidly determined that using the BioMek 1000 to handle strains and inoculation greatly decreased the manual workload and improved the reproducibility of the experiments. The figure "Overview of Inoculation Methods" (FIG. 4) shows some of the inoculation methods used. The individual methods are described in detail in the next sections. The methods are numbered in a manner which is recognized by the BioMek 1000 but can be identified in any other sufficient manner.

In general, it was found to be convenient to keep working stocks in 24-well microtiter plates (such as Falcon 3047 Multiwell tissue culture plates, Becton-Dickinson). The 24-well microtiter plates containing growth media, such as Tryptic Soy Broth without Dextrose (TSB-D) (Difco, Detroit, Mich., Cat. No. 48232-7058) or Tryptic Soy Broth (TSB) (Difco, Cat. No. 0370-07-5) were initially inoculated manually using sterile technique from either liquid stock cultures or directly from agar plates, such as Tryptic Soy Agar (Difco, Cat. No. 0370-07-5) (Figure left side). The 24-well microtiter plates could then be grown and stored as working stock cultures either in the refrigerator or with cryoprotectants, e.g., 10% glycerol, at −40° C. or lower. The 24-well microtiter plates were then used to inoculate either other 24-well microtiter plates as copies (see method INOC24V1 below) or 96-well microtiter plates typically for screening.

When 96-well microtiter plates were inoculated in one embodiment, typically only eight cultures were used per plate, with each culture being tested using a row of 12 wells. In one embodiment, a 2 ml deep-well microtiter plate is used as an intermediary for dilution and mixing to ensure that each row in the 96-well microtiter plate received the same inoculum. Methods such as INOCSQV0, INOCSQV2, INOCSQV3, and INOCSQV5 were developed to transfer strains to the 2 ml deep-well microtiter plate and mix them. The diluted strains were then transferred to 96-well microtiter plates and further diluted using the method INOC96V1. Finally, the method INCOPY96, can make a copy of strains in one 96-well microtiter plate to a second 96-well microtiter plate.

Following are descriptions of specific inoculation methods developed for implementation on a robotic system. Examples of these methods in use can be found in the "Examples" section which follows.

INOC24V1

This method copies the cultures from a 24-well plate containing stock microbial strains into an uninoculated 24-well plate that contains growth media. The P200 tool is used to add 40 µl of culture from the 24-well plate containing the stock strains to the uninoculated 24-well plate. Tips are changed for each strain.

INOCSQV0

Figure 21:
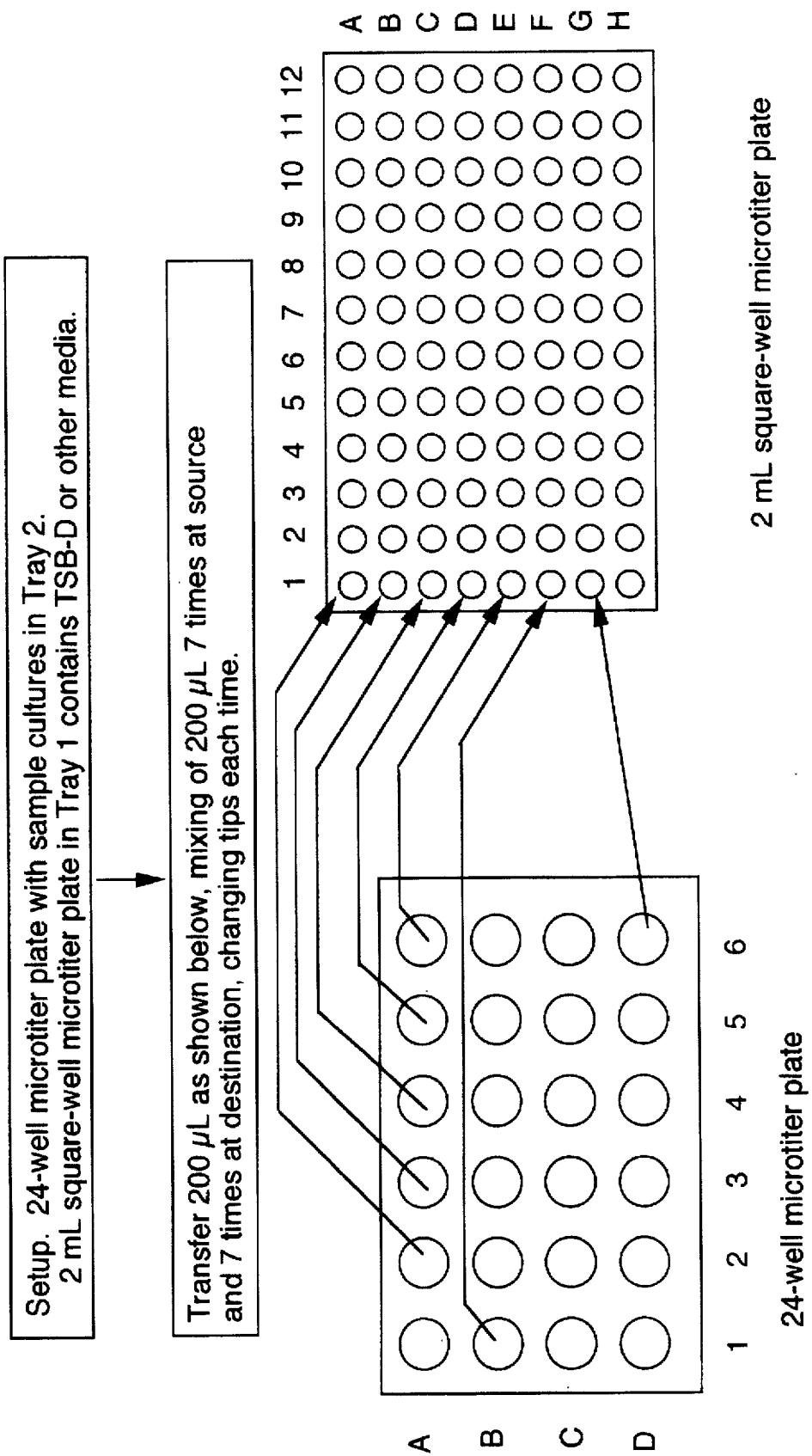
FIG. 21 is a pattern diagram of INOCSQV0.

This method inoculates the wells A1, B1, C1, D1, E1, F1, and G1 of a 2 ml square-well microtiter plate respectively from wells A2, A3, A4, A5, A6, B2, and D6 of a 24-well plate. Well H1 of the 2 ml square-well microtiter plate is an uninoculated control. 1.5 ml of TSB-D is typically used as media in column 1 of the 2 ml square-well microtiter plate, and is inoculated with 200'µL of cells in media from the 24-well plate. Mixing of 200 μL seven times is performed at the source and destination. Tips are changed for each strain. FIG. 21 is a pattern diagram of this method. INOCSQV2

Figure 22:
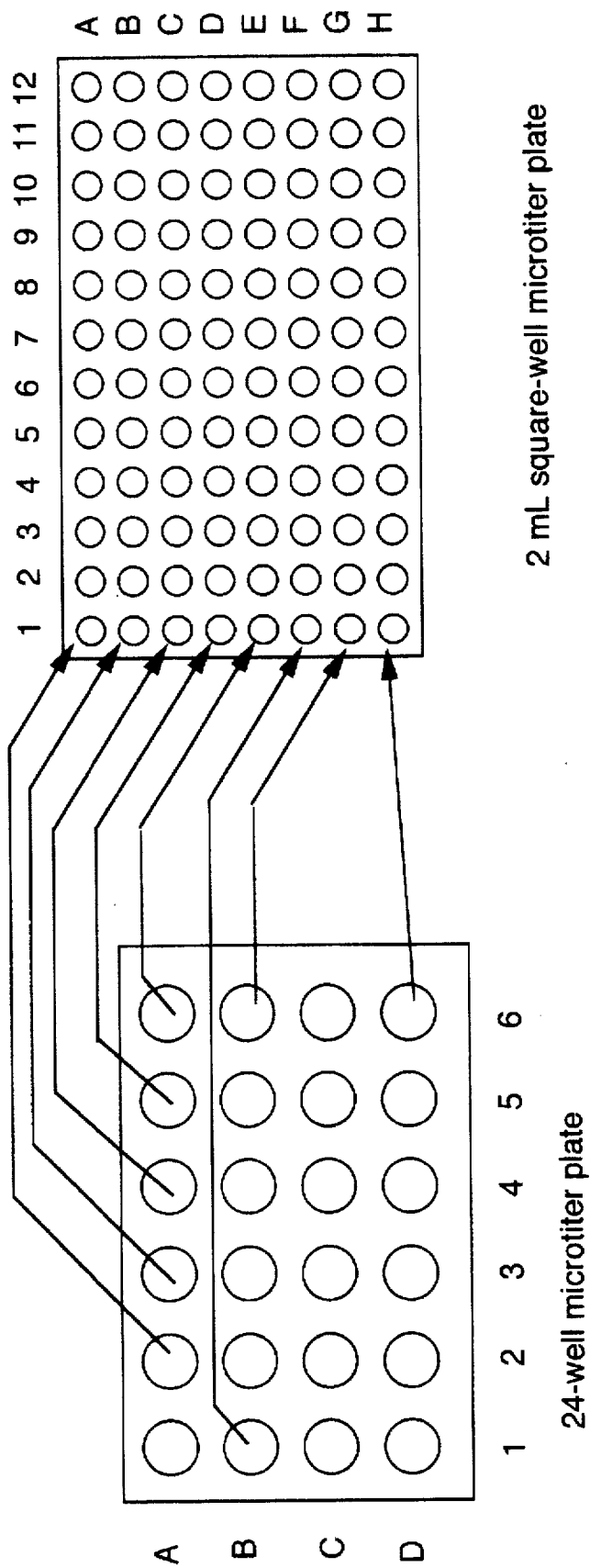
FIG. 22 is a pattern diagram of INOCSQV2.

This method inoculates the first column (column 1, 7 wells) of a 2 ml square-well microtiter plate respectively from wells A2, A3, A4, A5, A6, B2, and B6 of a 24-well plate. The last well of the 2 ml square-well microtiter plate, H1, is an uninoculated control. 1.5 ml of TSB-D is typically used as media in column 1 of the 2 ml square-well microtiter plate, and is inoculated with 200 μl of cells in media from the 24-well plate. Mixing of 200 μL seven times is performed at the source and destination. Tips are changed for each strain. FIG. 22 is a pattern diagram of this method.

INOCSQV3

This method inoculates the second column (column 2, 8 wells) of a 2 ml square-well microtiter plate respectively from wells A1, B3, B4, D2, D3, D4, D5, and D6 of a 24-well plate. 1.5 ml of TSB-D is typically used as media in column 1 of the 2 ml square-well microtiter plate, and is inoculated with 200 μl of cells in media from the 24-well plate. Mixing of 200 μL seven times is performed at the source and destination. Tips are changed for each strain. FIG. 23 is a pattern diagram of this method.

INOCSQV5

This method inoculates the first two column (columns 1 and 2, 16 wells) of a 2 ml square-well microtiter plate at Tray 1 from wells A1 to C4 by rows of a 24-well plate at Tray 2. 1.5 ml of TSB-D is typically used as media in columns 1 and 2 of the 2 ml square-well microtiter plate, and is inoculated with 200 μl of cells in media from the 24-well plate using the P200 tool. Mixing of 200 μL seven times is performed at the source and destination. Tips are changed for each strain.

INOC96V1

This method inoculates two 96-well plates prefilled with media (typically 200 μl of TSB-D) at Trays 2 and 3 from columns 1 and 2 of a 2 ml square-well microtiter plate. The method is typically run after one of the INOCSQV0 to INOCSQV5 series, or similar method was used to dilute and inoculate the 2 ml square-well microtiter plate.

The method uses a MP20 tool to transfer 20 μl of diluted cells from column 1 of the 2 ml square-well microtiter plate repeatedly to each column of the 96-well microtiter plate in tray 2. Column 2 of the 2 ml square-well microtiter plate is then used to inoculate repeatedly each column of the 96-well microtiter plate in tray 3.

INCOPY96

This method is typically used for copying cultures from a 96-well microtiter plate containing microbial strains to a second 96-well microtiter plate containing growth media. In effect a replicate of the first plate is created but with a lower cell density.

The method uses the MP20 tool to transfer 10 μl from a 96-well microtiter plate at Tray 2 into a second 96-well microtiter plate at Tray 3 with mixing seven times of 20 μl at both the source and destination plates. Typically the 96-well microtiter plate at Tray 3 contains 190 μl of growth media.

Utility Methods

The BioMek utility methods are used to assist in the manipulation of liquids and to set-up microtiter plates for experiments. (See elements 105, 106 and 103 in FIG. 3A and element 27 in FIG. 3B).

Following are descriptions of specific utility methods developed for implementation on a robotic system. Examples of these methods in use can be found in the "Examples" section which follows.

CRRES001

This method is used to manufacture 96-well microtiter plates with a range of concentrations of a target compound. This method loads each well of two 96-well microtiter plates at Trays 2 and 3 with 200 μL of liquid from Tray 1. Tray 1 contains four two-column quarter modules with liquid.

The source of the target compound is four quarter module split by length in Tray 1. For the two 96-well microtiter plates that are being created, the first five columns of the 96-well microtiter plates in Tray 2 are loaded with 200 μL from the left side of module A1 using the MP200 tool and then the first five columns of the 96-well microtiter plate in Tray 3 are loaded with 200 μL from the left side of module A1 using the MP200 tool.

The MP200 tool is then used to fill tray 2 in the following order: the sixth column is filled from the right side of module A1, the seventh column from the left side of module B1, the eighth column from the right side of module B1, the ninth column from the left side of module C1, the tenth column from the right side of module C1, the eleventh column from the left side of module D1, the twelfth column from the right side of module D1.

Following a tip change, the MP200 tool is used to fill Tray 3 in the following order: the sixth column is filled from the right side of module A1, the seventh column from the left side of module B1, the eighth column from the right side of module B1, the ninth column from the left side of module C1, the tenth column from the right side of module C1, the eleventh column from the left side of module D1, the twelfth column from the right side of module D1.

In one embodiment, Tray 1A contains TSB-D media in the left column and the other seven columns of the Tray 1 quarter modules contain TSB-D media with increasing concentrations of $K_2CR_2O_7$. The effect of this embodiment is to load two 96-well microtiter plates with 5 columns (1 through 5) of controls and 7 columns (6 through 12) with different concentrations of the target compound. The 96-well microtiter plates are then ready for inoculation.

190Bulk2

This method first primes the 8-channel bulk dispense tool with 2 ml from the reservoir and then dispenses 190 μL from the bulk dispense reservoir to a 96-well microtiter plate in Tray 3.

20P2TO31

This method copies 20 μL from a 96-well microtiter plate in Tray 2 to a 96-well microtiter plate in Tray 3. The destination 96-well microtiter plate is mixed two times with a volume of 20 μL.

10P2TO32

This method copies 10 μL from each well of a 96-well microtiter plate in Tray 2 to the same wells of a 96-well microtiter plate in Tray 3. The destination 96-well microtiter plate is mixed two times with a volume of 20 μL.

200MP200

This method uses an MP200 tool to dispense 200 μl from a single-well half module at Tray 1C into each well of a 96-well microtiter plate at Tray 2. Tray 1 contains modules. Tray 1A has an empty two column quarter module. Tray 1B has a two-column quarter module. Tray 1C has a single-well half module containing the liquid to be transferred.

Assay Methods

The assay methods are used to measure cell density and assay for biotransformations of target chemicals. (See elements 107 in FIG. 3A and 29 in FIG. 3B.) The methods require no human intervention after initial setup of the experiment. For measuring growth curves, two methods are described below, 2PL660V8 and 2PL66V10. 2PL660V8 adds water to counterbalance evaporation from columns 11 and 12 of the 2 ml square-well microtiter plate, while 2PL66V10 adds water from the 8-channel bulk dispense tool.

For performing the Microscale Cr(VI) Assay™, three methods are described, CRASS2P1, CRAS2PL1, and CRAS2DIL. CRASS2P1 uses single well and two column quarter modules in Tray 1 as a reservoir for Microscale Cr(VI) Assay™ reagents, while CRAS2PL1 uses a 2 ml square-well microtiter plate. The 2 ml square-well microtiter plate covered with aluminum foil seal is a significant improvement since it prevents the evaporation of the diphenylcarbazide (DPC) in acetone and allows the Microscale Cr(VI) Assay(tm) to be run at any time without manual intervention to add reagents. CRAS2DIL is used to dilute samples for assay and then perform the Microscale Cr(VI) Assay(tm) on both the diluted and undiluted samples. It also uses 2 ml square-well microtiter plates to hold the assay reagents.

Finally, a method, 2PL66AS1, that combines the Growth Assay and the Microscale Cr(VI) Assay™ is shown. As described above, the 2PL66AS1 method measures the growth curves of two 96-well microtiter plates and then automatically performs the Microscale Cr(VI) Assay™ without manual intervention after setup. This method allows completely automated collection of growth curve and Cr(VI) assay data for 192 wells.

2PL660V8 (Growth assay method)

This method uses the photometry tool at 30 min intervals to measure the growth of microorganisms in 96-well microtiter plates in trays 2 and 3. The elapsed time is approximately 20 hours. The data is stored in files PL2660 (for tray 2) and PL3660 (for tray 3), and unique file identifiers are added by the Genesis operating system. Following completion of the experiment, the data is transferred to a floppy disk and analyzed in a spreadsheet (for example, Excel by Microsoft Inc., Redmond, Wash.) to generate growth curves for all 192 wells. A 2 ml square-well microtiter plate is placed in tray 1. Columns 11 and 12 of the 2 ml square-well microtiter plate contain purified water, such as deionized water (VWR Scientific, West Chester, Pa. 19380, Cat. No. 3234-4). 30 µl of water is added to each 96-well microtiter plate at Trays 2 and 3 approximately every 3 hours. Two 96-well microtiter plates containing microorganisms inoculated into growth media are placed in Trays 2 and 3; the 96-well microtiter plates were usually inoculated by the BioMek using a method described above.

The method contains two nested loops. The outer loop will be executed six times, and in each execution will add 30 µl of sterile water using an MP200 tool and sterile pipette tips to each 96-well microtiter plate at trays 2 and 3 approximately every 3 hr. Column 11 of the 2 ml square-well microtiter plate at Tray 1 is used as the source of the sterile water for the 96-well microtiter plate at Tray 2 and column 12 of the 2 ml square-well microtiter plate at Tray 1 is used as the source of the sterile water for the 96-well microtiter plate at Tray 3.

The inner loop will be executed six times for each execution of the outer loop. The inner loop contains two functions. The first function reads the optical density at 660 nm. of the 96-well microtiter plate at Tray 2 and stores the data in the file PL2660 with a unique trailer. The second function reads the optical density at 660 nm. of the 96-well microtiter plate at Tray 3 and stores the data in the file PL3660 with a unique trailer. After reading the optical density of both plates, the loop pauses for 30 minutes.

2PL66V10 (Growth assay method)

This method uses the photometry tool to measure at 30 min intervals the growth of microorganisms in 96-well microtiter plates in trays 2 and 3. The elapsed time is approximately 20 hours. The data is stored in files PL2660 (for tray 2) and PL3660 (for tray 3), and unique file identifiers are added by the Genesis operating system. Following completion of the experiment, the data is transferred to a floppy disk and analyzed in a spreadsheet (for example, Excel by Microsoft Inc., Redmond, Wash.) to generate growth curves for all 192 wells. Two 96-well microtiter plates containing microorganisms inoculated into growth media are placed in Trays 2 and 3; the 96-well microtiter plates were usually inoculated by the BioMek using a method described above.

The method contains two nested loops. The outer loop will be executed four times, and in each execution will add 50 µl of sterile water using the 8-channel bulk dispense tool to each 96-well microtiter plate at trays 2 and 3 approximately every 3 hr. The inner loop will be executed six times for each execution of the outer loop. The inner loop contains two functions. The first function reads the optical density at 660 nm. of the 96-well microtiter plate at Tray 2 and stores the data in the file PL2660 with a unique trailer. The second function reads the optical density at 660 nm. of the 96-well microtiter plate at Tray 3 and stores the data in the file PL3660 with a unique trailer. After reading the optical density of both plates, the loop pauses for 45 minutes.

CRASS2P1 (Microscale Cr(VI) Assay™ Method)

This method performs the Microscale Cr(VI) Assay(tm) on two 96-well microtiter plates in Trays 2 and 3. Tray 1 contains the reagents for the assay. Tray 1A has an empty two column quarter module. Tray 1B has a two-column quarter module (Beckman, Cat. No. 372788) containing 5 mg/ml of diphenylcarbazide (DPC) (commercially supplied by Sigma Chemicals) dissolved in acetone (such as HPLC reagent acetone, Baker, Phillipsburg, N.J. 08865, Cat. No. 9002-02) in the left column, A3, and 10% vol./vol. $H_2SO_4$ (made from $H_2SO_4$, EM Science, Gibbstown, N.J. 08027, Cat. No. UN1830) in the right column, A4. Tray 1C has a single-well quarter module (Beckman, Cat. No. 372790), and Tray 1D has a single-well quarter module.

The method first uses the photometry tool to measure the optical density of the 96-well microtiter plate at Tray 2 at 660 nm. to quantify cell density; the data is stored in data file CR2660 with a unique identifier and printed. The method then uses the photometry tool to measure the optical density of the 96-well microtiter plate at Tray 3 at 660 nm. to quantify cell density; the data is stored in data file CR3660 with a unique identifier and printed. The photometry tool then measures the optical density of the 96-well microtiter plate at Tray 2 at 540 nm. referenced to 660 nm. to use as a blank for the subsequent Cr(VI) assay; the data is stored in data file CR2REF with a unique identifier and printed.

The photometry tool then measures the optical density of the 96-well microtiter plate at Tray 3 at 540 nm. referenced to 660 nm. to use as a blank for the subsequent Cr(VI) assay; the data is stored in data file CR3REF with a unique identifier and printed.

The MP20 tool next adds 20 µl of DPC from Tray 1A, well A3, to each well of the 96-well microtiter plate in Tray 2, changes tips, and adds 20 µl of DPC from Tray 1A, well A3, to each well of the 96-well microtiter plate in Tray 3. The MP200 tool next adds 60 µl of 10% $H_2SO_4$ from Tray 1A, well A4, to each well of the 96-well microtiter plate in Tray 2, changes tips, and adds 60 µl of 10% $H_2SO_4$ from Tray 1A, well A4, to each well of the 96-well microtiter plate in Tray 3. The method then pauses for four minutes to allow the complexation color development caused by the DPC complexing with Cr(VI) to develop.

The photometry tool then measures the optical density of the 96-well microtiter plate at Tray 2 at 540 nm. referenced to 660 nm. to quantify the Cr(VI) assay; the data is stored in data file CR2ASS with a unique identifier and printed. The photometry tool then measures the optical density of the 96-well microtiter plate at Tray 3 at 540 nm. referenced to 660 nm. to quantify the Cr(VI) assay; the data is stored in data file CR3ASS with a unique identifier and printed.

CRAS2PL1 (Microscale Cr(VI) Assay™ Method)

This method performs the Microscale Cr(VI) Assay™ on two 96-well microtiter plates in Trays 2 and 3. The method is modification of the CRASS2P1 to use a 2 ml square-well microtiter plate to contain the assay reagents. Tray 1 contains a 2 ml square-well microtiter plate with reagents for the Microscale Cr(VI) Assay(tm) with column five containing 5 mg/ml of diphenylcarbazide dissolved in acetone, and column 7 containing 10% $H_2SO_4$ to be used with the 96-well microtiter plate in Tray 2 and column 8 containing 10% $H_2SO_4$ to be used with 96-well microtiter plate in Tray 3. The method first uses the photometry tool to measure the optical density of the 96-well microtiter plate at Tray 2 at 660 nm. to quantify cell density; the data is stored in data file CR2660 with a unique identifier and printed.

The method then uses the photometry tool to measure the optical density of the 96-well microtiter plate at Tray 3 at 660 nm. to quantify cell density; the data is stored in data file CR3660 with a unique identifier and printed.

The photometry tool then measures the optical density of the 96-well microtiter plate at Tray 2 at 540 nm. referenced to 660 nm. to use as a blank for the subsequent Cr(VI) assay; the data is stored in data file CR2REF with a unique identifier and printed. The photometry tool then measures the optical density of the 96-well microtiter plate at Tray 3 at 540 nm. referenced to 660 nm. to use as a blank for the subsequent Cr(VI) assay; the data is stored in data file CR3REF with a unique identifier and printed.

The MP20 tool next adds 20 µl of DPC from column 5 of the 2 ml square-well microtiter plate at Tray 1 to each well of the 96-well microtiter plate in Tray 2, changes tips, and adds 20 µl of DPC from column 5 of the 2 ml square-well microtiter plate at Tray 1 to each well of the 96-well microtiter plate in Tray 3.

The MP200 tool next adds 60 µl of 10% $H_2SO_4$ from column 7 of the 2 ml square-well microtiter plate at Tray 1 to each well of the 96-well microtiter plate in Tray 2, changes tips, and adds 60 µl of 10% $H_2SO_4$ from column 8 of the 2 ml square-well microtiter plate at Tray 1 to each well of the 96-well microtiter plate in Tray 3.

The method then pauses for four minutes to allow the complexation color development caused by the DPC complexing with Cr(VI) to develop. The photometry tool then measures the optical density of the 96-well microtiter plate at Tray 2 at 540 nm. referenced to 660 nm. to quantify the Cr(VI) assay; the data is stored in data file CR2ASS with a unique identifier and printed. The photometry tool then measures the optical density of the 96-well microtiter plate at Tray 3 at 540 nm. referenced to 660 nm. to quantify the Cr(VI) assay; the data is stored in data file CR3ASS with a unique identifier and printed.

CRAS2DIL (Microscale Cr(VI) Assay™ Method)

This method is used to dilute samples for assay and then perform the Microscale Cr(VI) Assay™ on both the diluted and undiluted samples. The source 96-well microtiter plate containing the samples to be diluted is placed in Tray 2 and an empty 96-well microtiter plate is placed in Tray 3. Tray 1 contains a 2 ml square-well microtiter plate with reagents for the Microscale Cr(VI) Assay™ with column five containing 5 mg/ml of diphenylcarbazide dissolved in acetone, and column 7 containing 10% $H_2SO_4$ to be used with the 96-well microtiter plate in Tray 2 and column 8 containing 10% $H_2SO_4$ to be used with 96-well microtiter plate in Tray 3.

The first subroutine, 190Bulk1, uses the 8-channel bulk dispense tool to add 190 µl of high purity water from the reservoir into an empty 96-well microtiter plate in Tray 3. The second subroutine, 10P2TO31, next uses the MP20 tool to transfer 10 µl from a 96-well microtiter plate in Tray 2 containing the undiluted samples into the 96-well microtiter plate containing 190 µl of water in Tray 3.

The third subroutine, CRAS2DIL, then performs a version of the Microscale Cr(VI) Assay™ on both 96-well microtiter plates. The CRAS2DIL subroutine first uses the MP20 tool to add 20 µl of DPC from column 5 of the 2 ml square-well microtiter plate at Tray 1 to each well of the 96-well microtiter plate in Tray 2, changes tips, and adds 20 µl of DPC from column 5 of the 2 ml square-well microtiter plate at Tray 1 to each well of the 96-well microtiter plate in Tray 3.

The MP200 tool next adds 60 µl of 10% $H_2SO_4$ from column 7 of the 2 ml square-well microtiter plate at Tray 1 to each well of the 96-well microtiter plate in Tray 2, changes tips, and adds 60 µl of 10% $H_2SO_4$ from column 8 of the 2 ml square-well microtiter plate at Tray 1 to each well of the 96-well microtiter plate in Tray 3. The method then pauses for four minutes to allow the complexation color development caused by the DPC complexing with Cr(VI) to develop. The photometry tool then measures the optical density of the 96-well microtiter plate at Tray 2 at 540 nm. referenced to 660 nm. to quantify the Cr(VI) assay of the diluted samples; the data is stored in data file CRCONASS with a unique identifier and printed.

The photometry tool then measures the optical density of the 96-well microtiter plate at Tray 3 at 540 nm. referenced to 660 nm. to quantify the Cr(VI) assay of the diluted samples; the data is stored in data file CR1TO10 with a unique identifier and printed.

2PL66AS1 (Combined Growth Assay and Microscale Cr(VI) Assay™ Method)

This method quantifies the growth of microorganisms in two 96-well microtiter plates, and then performs the Microscale Cr(VI) Assay™ without operator intervention. The two 96-well microtiter plates are placed in Trays 2 and 3, and contain microorganisms in growth media which in one embodiment have a range of concentrations of the target chemical. The plates were typically filled with media containing a range of target chemical concentrations by the utility routine CRRES001 and then inoculated with microorganisms by one of the inoculation methods described above.

The first subroutine, 2PL660V9, measures the growth curves of the two 96-well microtiter plates using the photometry tool. At 45 min intervals for approximately 20 hours of elapsed time, the optical density of microorganisms at 660 nm. is measured for the 96-well microtiter plates at trays 2 and 3. The data is stored in files PL2660 (for tray 2) and PL3660 (for tray 3), and unique file identifiers are added by the Genesis operating system. Following completion of the experiment, the data is transferred to a floppy disk and analyzed in a spreadsheet (for example, Excel by Microsoft Inc., Redmond, Wash.) to generate growth curves for all 192 wells.

The 2PL660V9 subroutine contains two nested loops. The outer loop will be executed four times, and in each execution will add 45 µl of sterile water using the 8-channel bulk dispense tool to each 96-well microtiter plate at trays 2 and 3 approximately every 3 hr. The inner loop will be executed six times for each execution of the outer loop. The inner loop contains two functions. The first function reads the optical density at 660 nm. of the 96-well microtiter plate at Tray 2 and stores the data in the file PL2660 with a unique trailer. The second function reads the optical density at 660 nm. of the 96-well microtiter plate at Tray 3 and stores the data in the file PL3660 with a unique trailer. After reading the optical density of both plates, the loop pauses for 45 minutes.

The Microscale Cr(VI) Assay™ portion of the method is performed by the CRAS2PL1 subroutine. This CRAS2PL1 subroutine performs the Microscale Cr(VI) Assay™ on the two 96-well microtiter plates in Trays 2 and 3. Tray 1 contains a 2 ml square-well microtiter plate with reagents for the Microscale Cr(VI) Assays™ with column five containing 5 mg/ml of diphenylcarbazide dissolved in acetone, and column 7 containing 10% $H_2SO_4$ to be used with the 96-well microtiter plate in Tray 2 and column 8 containing 10% $H_2SO_4$ to be used with 96-well microtiter plate in Tray 3 .

The CRAS2PL1 subroutine first uses the photometry tool to measure the optical density of the 96-well microtiter plate at Tray 2 at 660 nm. to quantify cell density; the data is stored in data file CR2660 with a unique identifier and printed.

The CRAS2PL1subroutine then uses the photometry tool to measure the optical density of the 96-well microtiter plate at Tray 3 at 660 nm. to quantify cell density; the data is stored in data file CR3660 with a unique identifier and printed.

The CRAS2PL1 subroutine then uses the photometry tool to measure the optical density of the 96-well microtiter plate at Tray 2 at 540 nm. referenced to 660 nm. to use as a blank for the subsequent Cr(VI) assay; the data is stored in data file CR2REF with a unique identifier and printed.

The CRAS2PL1 subroutine then uses the photometry tool to measure the optical density of the 96-well microtiter plate at Tray 3 at 540 nm. referenced to 660 nm. to use as a blank for the subsequent Cr(VI) assay; the data is stored in data file CR3REF with a unique identifier and printed.

The CRAS2PL1 subroutine then uses the MP20 tool to add 20 µl of DPC from column 5 of the 2 ml square-well microtiter plate at Tray 1 to each well of the 96-well microtiter plate in Tray 2, changes tips, and adds 20 µl of DPC from column 5 of the 2 ml square-well microtiter plate at Tray 1 to each well of the 96-well microtiter plate in Tray 3.

The CRAS2PL1 subroutine then uses the MP200 tool to add 60 µl of 10% $H_2SO_4$ from column 7 of the 2 ml square-well microtiter plate at Tray 1 to each well of the 96-well microtiter plate in Tray 2, changes tips, and adds 60 µl of 10% $H_2SO_4$ from column 8 of the 2 ml square-well microtiter plate at Tray 1 to each well of the 96-well microtiter plate in Tray 3. The method then pauses for four minutes to allow the complexation color development caused by the DPC complexing with Cr(VI) to develop.

The photometry tool then measures the optical density of the 96-well microtiter plate at Tray 2 at 540 nm. referenced to 660 nm. to quantify the Cr(VI) assay; the data is stored in data file CR2ASS with a unique identifier and printed. The photometry tool then measures the optical density of the 96-well microtiter plate at Tray 3 at 540 nm. referenced to 660 nm. to quantify the Cr(VI) assay; the data is stored in data file CR3ASS with a unique identifier and printed.

Experimental

The following examples and definitions are provided in order to demonstrate and further illustrate certain preferred embodiments and aspects of the present invention and are not to be construed as limiting the scope thereof.

Definitions

The terms "sample" and "specimen" in the present specification and claims are used in their broadest sense. On the one hand, they are meant to include both biological and environmental samples. On the other hand, they are meant to include a specimen or culture. (e.g., stock cultures of microorganisms).

Environmental samples include environmental material such as hazardous waste material, surface matter, soil, water, sludge, wastewater, and industrial samples, as well as samples obtained from food and dairy processing instruments, apparatus, equipment, disposable and non-disposable items. Biological samples may be animal, including human, fluid or tissue, food products and ingredients such as dairy items, vegetables, meat and meat by-products, cultures, organisms, and waste. However, it is not intended that the sample type applicable to the present invention be limited.

Whether biological or environmental, a sample suspected of containing microorganisms may or may not first be subjected to an enrichment means to create a "pure culture" of microorganisms. By "enrichment means" or "enrichment treatment," the present invention contemplates (i) conventional techniques for isolating a particular microorganism of interest away from other microorganisms by means of liquid, solid, semi-solid or any other culture medium and/or technique, and (ii) novel techniques for isolating particular microorganisms away from other microorganisms. It is not intended that the present invention be limited only to one enrichment step or type of enrichment means. For example, it is within the scope of the present invention to, following subjecting a sample to a conventional enrichment means, subjecting the resultant preparation to further purification such that pure or substantially pure cultures of a strain of a species of interest are produced. This pure culture may then be analyzed by the present invention.

As used herein, the term "culture" refers to any sample or specimen which is suspected of containing one or more microorganisms. "Pure cultures" are cultures in which the organisms present are only of one strain of a particular genus and species. This is in contrast to "mixed cultures," which are cultures in which more than one genus and/or species of microorganism are present.

As used herein, the term "organism" is used to refer to any species or type of microorganism, including but not limited to eubacteria, archaebacteria, yeasts and other fungi. As used herein, the term fungi, is used in reference to eukaryotic organisms such as the molds and yeasts, including dimorphic fungi.

As used herein, the terms "microbiological media" and "culture media," and "media" refer to any substrate for the growth and reproduction of microorganisms. "Media" may be used in reference to solid plated media which support the growth of microorganisms. Also included within this definition are semi-solid and liquid microbial growth systems including those incorporate living host organisms, as well as any type of media.

As used herein, the term "selective media" refers to media which support the growth of particular organisms of interest but inhibit other organisms. Such inhibition may result due to medium constituents such as compounds which are selectively toxic, as well as the end-products of microbial metabolism produced by organisms which utilize the medium constituents.

As used herein, the term "differential media" refers to media which support the growth of various organisms, but permit visual differentiation between the different genera or species. While some media are either selective or differential, some media are both selective and differential.

As used herein, the term "carbon source" is used in reference to any compound which may be utilized as a source of carbon for bacterial growth and/or metabolism. Carbon sources may be in various forms, including, but not limited to polymers, carbohydrates, acids, alcohols, aldehydes, ketones, amino acids, and peptides.

As used herein, the term "nitrogen source" is used in reference to any compound which may be utilized as a source of nitrogen for bacterial growth and/or metabolism. As with carbon sources, nitrogen sources may be in various forms, such as free nitrogen, as well as compounds which contain nitrogen, including but not limited to amino acids, peptones, vitamins, and nitrogenous salts.

As used herein, the term "primary isolation" refers to the process of culturing organisms directly from the sample. Primary isolation may also be done in liquid or semi-solid media.

As used herein, the term "testing substrate" is used in reference to any compound, carbon and/or nitrogen source that may be utilized to identify the detoxification or growth characteristics of bacteria based on their biochemical capabilities. For example, one bacterial species may utilize one testing substrate that is not utilized by another species. This utilization may then be used to differentiate between these two species and identify the species of interest in bioremediation applications. It is contemplated that numerous testing substrates be utilized in combination. Testing substrates may be tested individually (e.g., one substrate per testing well or compartment, or testing area) or in combination (e.g., multiple testing substrates mixed together and provided as a "cocktail").

Following exposure to a testing substrate the response of an organism may be detected. This detection may be visual (ie., by eye) or accomplished with the assistance of machine (s) . For example, the response of organisms to carbon sources may be detected as turbidity in the suspension due to the utilization of a testing substrate by the organisms. Likewise, growth can be used as an indicator that an organism is not inhibited by certain compounds (e.g., chromium). In one embodiment, color is used to indicate the presence or absence of organism growth/metabolism, and/or the ability of an organism to detoxify a compound.

As used herein, the terms "chromogenic compound" and "chromogenic substrate," refer to any compound useful in detection systems by their light absorption or emission characteristics. The term is intended to encompass any enzymatic cleavage products, soluble, as well as insoluble, which are detectable either visually or with optical machinery. Included within the designation "chromogenic" are all enzymatic substrates which produce an end product which is detectable as a color change. This includes, but is not limited to any color, as used in the traditional sense of "colors," such as indigo, blue, red, yellow, green, orange, brown, etc., as well as fluorochromic or fluorogenic compounds, which produce colors detectable with fluorescence (e.g., the yellow-green of fluorescein, the red of rhodamine, etc.). It is intended that such other indicators as dyes (e.g., pH) and luminogenic compounds be encompassed within this definition.

As used herein, the commonly used meaning of the terms "pH indicator," "redox indicator," and "oxidation-reduction indicator," are intended. Thus, "pH indicator" encompasses all compounds commonly used for detection of pH changes, including, but not limited to phenol red, neutral red, bromthymol blue, bromcresol purple, bromcresol green, bromchlorophenol blue, m-cresol purple, thymol blue, bromcresol purple, xylenol blue, methyl red, methyl orange, and cresol red. The terms "redox indicator" and "oxidation-reduction indicator" encompasses all compounds commonly used for detection of oxidation/reduction potentials (ie., "eH") including, but not limited to various types or forms of tetrazolium, resazurin, and methylene blue.

As used herein, the term "testing device" is used in reference to testing systems in which at least one organism is tested for more than one test characteristic, such as detoxification of a compound and/or susceptibility to an antimicrobial agent. It is also intended that other compounds such as carbon sources or antimicrobials will be included within compartments (e.g., wells) within the device. It is not intended that the present invention be limited to a particular size or configuration of testing device. For example, it is contemplated that various formats will be used with the present invention, including, but not limited to microtiter plates, petri plates with internal dividers used to separate different media formulations placed within the plate, test tubes, beakers, as well as many other formats.

As used herein, the terms "microtiter plate," and "microplate," are used in reference to standard microtiter plates commonly used in the art and commercially available from numerous scientific supply sources (e.g., Biolog, Fisher, etc.). However, it is not intended that the present invention be limited to any particular type of format. For example, plates with 96, 24, and 12 wells are useful in the present invention, although plates with different numbers of wells may be used.

As used herein, the term "screen" refers to procedures in which the characteristics of multiple organisms or compounds are tested.

As used herein, the term "automated" refers to the situation in which robots or other machines are used to perform manipulations. It is intended that a range of automation be encompassed within this definition, including "semiautomatic" or "partially automated" procedures in which machines are used to perform some steps of a method, while humans perform other steps.

As used herein, the term "BioMek" is used in reference to any of the BioMek automated workstations. It is not intended that the invention be limited to the BioMek 1000, rather, it is intended that the term encompass other models, such as the BioMek 2000, or any other system which is suitable for use in the present invention.

As used herein, the term "inoculating suspension" or "inoculant" is used in reference to a suspension which may be inoculated with organisms to be tested. It is not intended that the term "inoculating suspension" be limited to a particular fluid or liquid substance. For example, inoculating suspensions may be comprised of water, saline, or an aqueous solution which includes at least one gelling agent. It is also contemplated that an inoculating suspension may include a component to which water, saline or any aqueous material is added. It is contemplated in one embodiment, that the component comprises at least one component useful for the intended microorganism. It is not intended that the present invention be limited to a particular component.

As used herein, the term "kit" is used in reference to a combination of reagents and other materials. It is contemplated that the kit may include reagents such as carbon sources, nitrogen sources, chromogenic substrates, antimicrobials, diluents and other aqueous solutions, as well as microplates, as well as other components. It is not intended that the term "kit" be limited to a particular combination of reagents and/or other materials. Further, in contrast to methods and kits which involve inoculating organisms on or into a preformed matrix such as an agar surface or broth, the present invention involves inoculation of a testing plate in which the organisms are suspended within a gel-forming matrix.

As used herein, the term "detoxify" is used in its broadest sense. It is intended to encompass the alteration of toxic compounds to states that are either less toxic or non-toxic. For example, with metals, detoxification includes, but is not limited to biotransformation from one valence state to another; binding, sequestering, or volatilizing metals and their derivatives; conversion to forms with altered mobilities; derivatization to form compounds and molecules with improved properties, such as reduced toxicity; metabolism into cellular material; and alteration of the properties of the contaminant or contaminant mixture to facilitate the application of other remediation technologies. In addition, for organics, detoxification includes, but is not limited to degradation of the organic; binding, sequestering, or volatilizing the compound and derivatives; conversion to forms with altered mobilities; derivatization to form compounds and molecules with improved properties, such as reduced toxicity; metabolism into cellular material; and alteration of the properties of the contaminant or contaminant mixture to facilitate the application of other remediation technologies. It is not contemplated that the chemical compounds be in any particular concentration or state. It is also intended that the chemical compounds be present either alone or in a mixture with other toxic and/or non-toxic compounds.

In the present application, including the experimental disclosure which follows, the following abbreviations apply: eq (equivalents); M (Molar); µM (micromolar); N (Normal); mol (moles); mmol (millimoles); µmol (micromoles); nmol (nanomoles); g (grams); mg (milligrams); µg (micrograms); ng (nanograms); 1 or L (liters); ml (milliliters); µl (microliters); cm (centimeters); mm (millimeters); µm (micrometers); nm (nanometers); MRAD (megarad); °C. (degrees Centigrade); CFU (colony forming units); EPA (U.S. Environmental Protection Agency); DOD (U.S. Department of Defense); DOE (U.S. Department of Energy); IBM (International Business Machines, Armonk, N.Y.); Beckman (Beckman Instruments, Fullerton, Calif.); Microsoft (Microsoft Corp., Redmond, Wash.); BioMek (BioMek 1000, Beckman); ELISA (Enzyme-Linked Immunosorbent Assay); TSA (trypticase soy agar or tryptic soy agar); TSB (trypticase soy broth or tryptic soy broth); TSB-D (TSB without dextrose included; i.e., Bacto Tryptic Soy Broth without Dextrose, Difco); DPC (diphenylcarbazide); Oxoid (Oxoid, Basingstoke, England); BBL (Becton Dickinson Microbiology Systems, Cockeysville, Md.); DIFCO or Difco (Difco Laboratories, Detroit, Mich.); U.S. Biochemical (U.S. Biochemical Corp., Cleveland, Ohio); Scientific Products (McGraw Park, Ill.); Sigma (Sigma Chemical Co., St. Louis, Mo.); Millipore (Millipore, Corp., Marlborough, Mass.); Baker (Baker, Phillipsburg, N.J.); EM (EM Science, Gibbstown, N.J.); VWR (VWR Scientific, San Francisco, Calif.); and Costar (Costar Corp., Cambridge, Mass.).

Unless otherwise indicated, the $K_2Cr_2O_7$, and DPC were obtained from Sigma, while the TSA, TSB and TSB-D were obtained from Difco.

Various organisms were utilized in the following examples, including those listed in Table 1 below. All of these organisms were obtained from Biolog (Biolog, Inc., Hayward, Calif.). An additional organism, $B.$ $subtilis$ $met^-$ $lys^-$ 168 (hereinafter "$B.$ $subtilis$ 168"), kindly provided by T. Leighton, of the University of California, Berkeley, was also tested.

TABLE 1

| Gram-Negative Organisms and Their Biolog Strain Numbers | | Gram-Positive Organisms and Their Biolog Strain Numbers | |
|---|---|---|---|
| *Acidovorax facilis* (#7563) | *Klebsiella terrigena* (#8045) | *Arthobacter histidinolovorans* (#9721) | *B. pasteurii* (#9258) |
| *Acinetobacter calcoaceticus baumannii* (#11026) | *Ochrobacterium anthropi* (#1185) | *Bacillus alcalophilus ss halodurans* (#9675) | *B. polymyxa* (#9702) |
| *A. genospecies 10* (#11076) | *Pragia fontium* (#7302) | *B. amyloliquefaciens* (#9676) | *B. pumilus* (#9259) |
| *A. lwoffii/ genospecies 8* (#9466) | *Psueodomonas aeruginosa* (#997) | *B. azotoformans* (#9235) | *B. racemilacticus* (#9705) |
| *Aeromonas hydrophila DNA group 1* (#6836) | *P. agarici* | *B. badius* (#9237) | *B. sphaericus* (#9263) |
| *A. salmonicida ss achromogenes* (#9470) | *P. cissicola* (#9544) | *B. brevis* (#9238) | *B. stearothermophilus* (#9601) |
| *Agrobacterium radiobacter* (#2717) | *P. diminuta* (#8528) | *B. cereus/thuringiensis* (#9239; 9267) | *B. subtilis* (#9264) |
| *Budvicia aquatica* (#3278) | *P. putida* type A2 (#3851) | *B. circulans* (#9242) | *B. subtilis* var. *globigii* (#12319) |
| *Burkholderia cepacia* (#8522) | *P. stutzeri* (#8569) | *B. coagulans* (#9243) | CDC group A-5 Subgroup b (#9722) |
| *Chromobacterium violaceum* (#2865) | *Psychrobacter immobilis* (#3083) | *B. fastidiosus* (#9678) | *Cellulomonas flavigena* (#10353) |

TABLE 1-continued

| Gram-Negative Organisms and Their Biolog Strain Numbers | | Gram-Positive Organisms and Their Biolog Strain Numbers | |
|---|---|---|---|
| Chryseomonas luteola (#8542) | Rhizobium meliloti a (#12170) | B. firmus (#9244; 9750) | Corynebacterium vitarumen (#9619) |
| Comamonas testosteroni (#8571) | Shewanella putrefaciens a (#3836) | B. gordonae (#9246) | Deinococcus (#9657) |
| Enterobacter agglomerans biogroup 2b (#11511) | Sphingomonas paucimobilis a (#8551) | B. insolitus (#9247) | Enterococcus saccharolyticus (#11137) |
| E. cloacae a (#9980) | Vibrio damsela (#3033) | B. laevolacticus (#9679) | Gordona terrae (#11147) |
| Erwinia amylovora (#8006) | V. fluvialis i (#7257) | B. larvae (#9680) | Micrococcus diversus (#9271) |
| Flavobacterium breve (#2708) | Xanthomonas maltophila (#946) | B. lichenformis (#9251) | M. luteus (#9272) |
| Hydrogenophaga flava (#8534) | Xenorhabdus luminescens (#9932) | B. macerans (#9252) | M. naucinus (# |
| | | B. macquariensis (#9681) | R. equi (#11152) |
| | | B. maroccanus (#9253) | Staphylococcus aureus (#11169) |
| | | B. megaterium (#9255) | S. chromogenes (#11215) |
| | | B. mycoides (#9257) | S. lentus (#9634) |
| | | B. pabuli (#9757) | Streptococcus alactolyticus (#11108) |
| | | B. pantothenticus (#9258) | S. intermedius (#11124) |

In the following experiments, the feasibility of screening microorganisms for bioremediation traits was demonstrated with the BioMek 1000 workstation. A general, scaleable technology using a 96-well microtiter plate formats was developed and then automated on a BioMek 1000 robot.

Microorganisms were grown primarily in microtiter plates on the BioMek 1000 workstation, with growth monitored by the photometry tool. Contaminants of interest, such as chromate, were added to the culture media before inoculation, or during or after growth. Initial studies were conducted to determine the range of contaminant tolerated by each strain, and to determine the upper range of Cr(VI) that could be reduced to Cr(III), or removed from the system. Following contact, when necessary, microorganisms can be separated from the media by filtration, such as with a Millipore MultiScreen filtration system.

EXAMPLE 1

In this experiment, the EPA Method 7196 colorimetric assay for Cr(VI) was modified for use on the robot and the Microscale Cr(VI) Assay™ created. EPA Method 7196 is a standard method for determination of Cr(VI), based upon the reaction of Cr(VI) with diphenylcarbazide (DPC) to form a colored complex that absorbs at 540 nm. Sulfuric acid is added to reduce the pH to 2±0.5, and the absorbance at 540 nm. is measured.

In this experiment, Method 7196 was scaled down from 100 ml to 200 µl, and implemented in a 96-well microtiter plate format. The resultant Microscale Cr(VI) Assay™ was then automated on the BioMek robot and the two compounds in the assay optimized to function in the presence of growth media and microorganisms. Thus, the implementation of EPA Method 7196 as an automated Microscale Cr(VI) Assay™ on the BioMek required a scale-down in volume and the BioMek had to be programmed to add the DPC reagent, $H_2SO_4$, and read the optical density. The volumes and concentrations of DPC and $H_2SO_4$ needed were determined in preliminary experiments.

A BioMek software method was written to perform a dilution series equally distributed in 12 steps, between two points (in this case, 0 mg/l and 5 mg/l of $K_2Cr_2O_7$) using a whole 96-well microtiter plate and eight replicates per concentration. A second BioMek software method was written to perform the diphenylcarbazide assay by adding 50 µl per well of freshly made 2% $H_2SO_4$ and 0.5 mg/l DPC in water, in order to acidify the reaction and start the reaction, then paused for 5 minutes to allow the reaction to develop. The optical density was then read at 490 nm.

Figure 5:
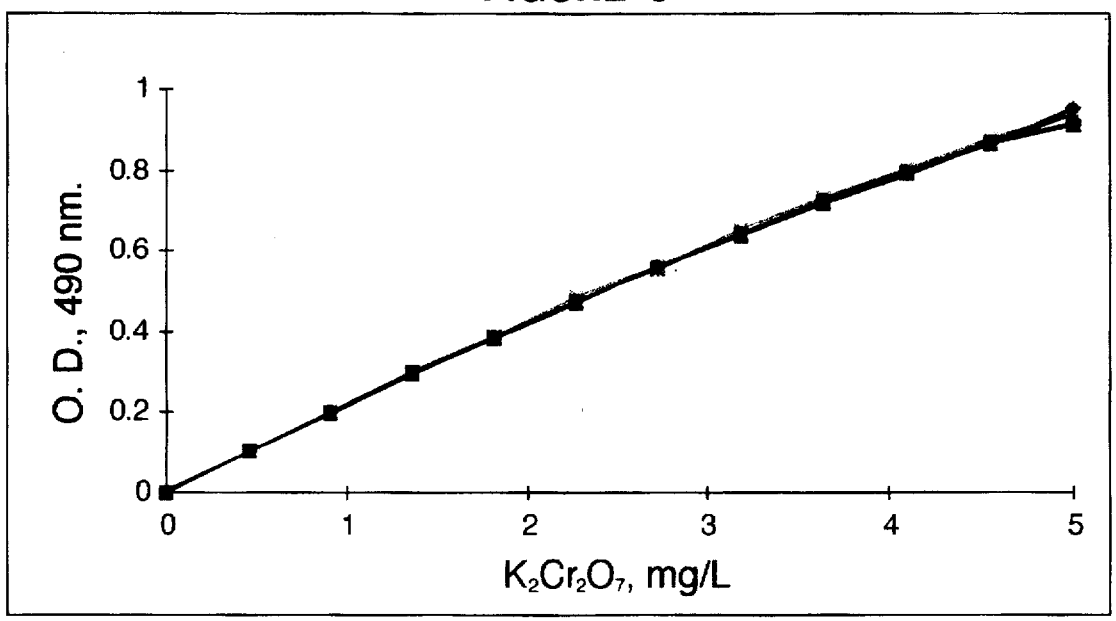
FIG. 5 is a Cr(VI) standard curve, implemented in 96-well microtiter plates on the Biomek 1000.

In FIG. 5, a Cr(VI) standard curve prepared and read by the BioMek is shown. The values shown along the ordinate represent the optical density at 490 nm; the values shown along the abscissa represent the concentration of $K_2Cr_2O_7$ in mg/L. The standard curve shown in FIG. 5 represents the average curve generated from the 8 replicate samples. As indicated, a linear response was produced, with very little scatter between the eight points at each concentration. The overall precision, as defined by percent relative standard deviation, was 0.82%. All of the manipulations were performed entirely by the BioMek. FIG. 5 clearly demonstrates the automation on the BioMek of the EPA Method 7196 in the Microscale Cr(VI) Assays™.

EXAMPLE 2

In this experiment, methods to overcome the problems identified in initial experiments relating to buffering of the 7196 reaction due to the presence of TSB-D were investigated. This was a significant problem, as the buffering of the reaction by TSB-D resulted in an elimination of purple indicator color at 540 nm.

This experiment involved determination of the method performance in the presence of TSB-D growth media. A standard curve was created, with 11 equal intervals between 0 and 5 mg/l of $K_2Cr_2O_7$ in TSB-D. For each concentration, one column (8 wells) was used. To each well, 8.5 µl of 10% $H_2SO_4$ was added and mixed. Next, 5 µl of 5 mg/ml DPC was added. After 5 min., the optical density was measured at 540 nm by the BioMek.

Figure 6:
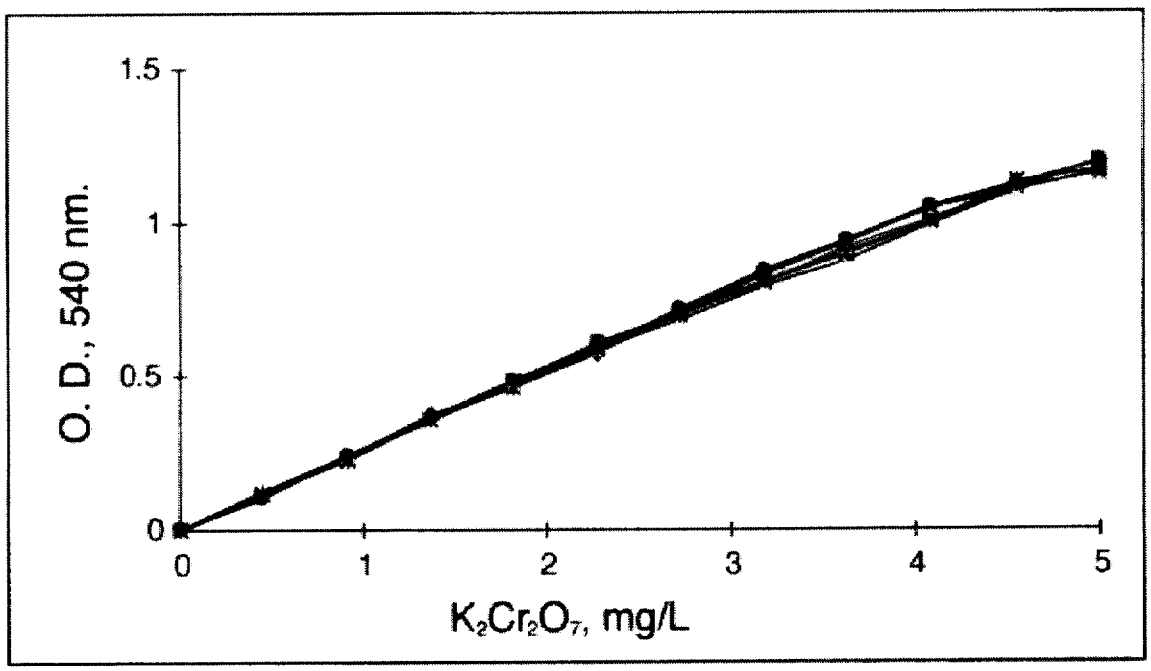
FIG. 6 is a plot for a Cr(VI) assay in TSB-D.

The results of the Cr(VI) assay in TSB-D growth medium are shown in FIG. 6 For the results shown in FIG. 6, eight replicates were measured for each concentration of $K_2Cr_2O_7$ shown. The values shown along the ordinate represent the optical density at 540 nm; the values shown along the abscissa represent the concentration of $K_2Cr_2O_7$ in mg/L. The standard curve shown in FIG. 6 represents the average curve generated from the 8 replicate samples. As indicated in this figure, a linear dose response of the assay to increasing $K_2Cr_2O_7$ is seen.

Thus, a major adaptation of the EPA Method 1796 to the Microscale Cr(VI) Assay™ described in the present invention involved an approximately 6-fold increase the amount of acid needed to counteract the buffering by the media. The assay also displays a small increase in scatter. Additionally, TSB-D and other media was also found to slowly reduce Cr(VI) to Cr(III).

EXAMPLE 3

A series of experiments were run to measure the time course of Cr(VI) reduction by water and TSB-D at various temperatures and concentrations. In one experiment, $K_2Cr_2O_7$ was diluted in water to produce 50 ml stocks at 0.05, 1, 0.5, 5, 10, and 50 mg/l. These stocks were incubated at room temperature. At 0, 120', 258', 16 h 10', 42 h, 66 h, 140 h, and 210 h, 200 µl samples were withdrawn and 20 µl of 5 mg/ml DPC and 60 µl of 10% $H_2SO_4$ were added. After 5 min, the optical density at 540 nm., was measured by the BioMek. By 140 h, a significant decrease in Cr(VI) content was evident.

In another experiment, 0.5, 1, 10, and 100 mg/l stocks of $K_2Cr_2O_7$ in TSB-D were made and placed at 40° C., 32° C., room temperature, 4° C., −20° C., and −40° C. At various times over the course of several weeks, aliquots were removed and assayed for Cr(VI) by adding 20 µl of 5 mg/ml DPC and 60 µl of 10% $H_2SO_4$. After 5 min, the optical density at 540 nm., was measured by the BioMek. The results of the experiments resulted in stock solutions of Cr(VI) in TSB-D being made fresh, or stored for less than 3 days at 4° C., or stored for longer periods at −40° C.

EXAMPLE 4

In order for the present invention to work as a screen for microorganisms useful for detoxification of Cr(VI), it was necessary to determine the conditions under which the Microscale Cr(VI) Assay™ would function without interference from microorganisms, since cell density or the growth phase might impact the Microscale Cr(VI) Assay™.

In one experiment, the impact of microbial cell density on the Microscale Cr(VI) Assay™ was determined. *Bacillus subtilis* 168 (obtained from T. Leighton, University of California, Berkeley, Calif.) was grown in TSB-D to stationary phase and then diluted with TSB-D into 12 cell densities, ranging from undiluted to diluted by 12-fold. $K_2Cr_2O_7$ was then added by method CRCAL541 to form a standard curve and the Microscale Cr(VI) Assay™ immediately initiated (incubation with $K_2Cr_2O_7$ could have resulted in a reduction of Cr(VI) to Cr(III) by the microbes).

Figure 7:
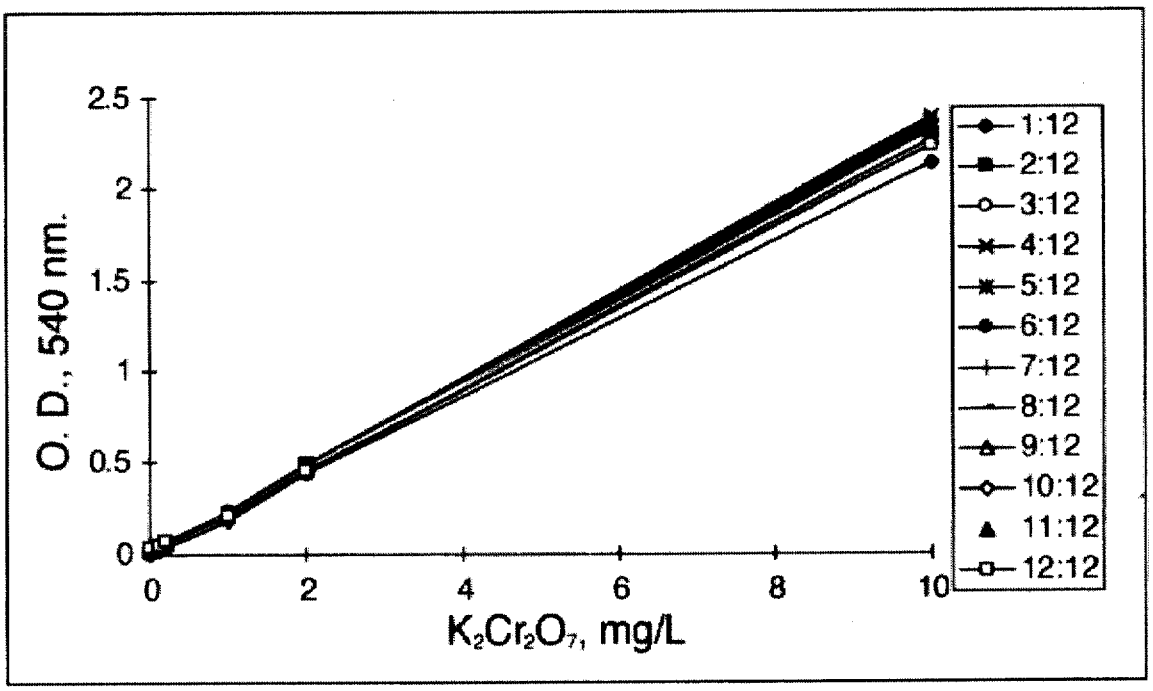
FIG. 7 is a plot showing the effect of cell density on the Microscale Cr(VI) Assay™.

The results of this experiment are shown in FIG. 7. In this figure, the values shown along the ordinate represent the optical density at 540 nm; the values shown along the abscissa represent the concentration of $K_2Cr_2O_7$ in mg/L. The insert contained within FIG. 12 indicates which symbols correspond to the curves generated by samples corresponding to the undiluted (12:12) to diluted by 12 fold (1:12) cell densities used in the Microscale Cr(VI) Assay™. This figure demonstrates that there is essentially no effect of cell density on the Microscale Cr(VI) Assay™ over a 12-fold range of cell densities.

To minimize absorbance effects of cells, when the Microscale Cr(VI) Assay™ was performed in the presence of microbial cells, typically, the optical density at 540 nm. that quantifies the Cr(VI) concentration was referenced against optical density readings at 660 nm. that quantifies cell density. This wavelength (660 nm.) was chosen as the reference in supporting experiments.

In methods such as OD540V1, CRASS2P1, and CRAS2PL1, the OD at 660 nm of the 96-well microtiter plates were first read, in order to record the final cell density of the microorganisms immediately before the Cr(VI) assay. The OD at 540 nm. referenced to 660 nm. was then read. This provided the assay blank. The Microscale Cr(VI) Assay™ reagents were added and, after a four min incubation, the OD at 540 nm., referenced to 660 nm. was read for the assay values. In the data analysis, the assay blank is subtracted from the assay values to correct for absorbance at 540 nm. by the cells.

EXAMPLE 5

The impact of growth phase was another possible problem in performance of the Microscale Cr(VI) Assay™ in the presence of microbial cells. While FIG. 7 showed that cell density for stationary phase *B. subtilis* cells has no significant impact on the Microscale Cr(VI) Assay™, it was necessary to determine whether the phase of cell growth significantly affects the assay.

Figure 8:
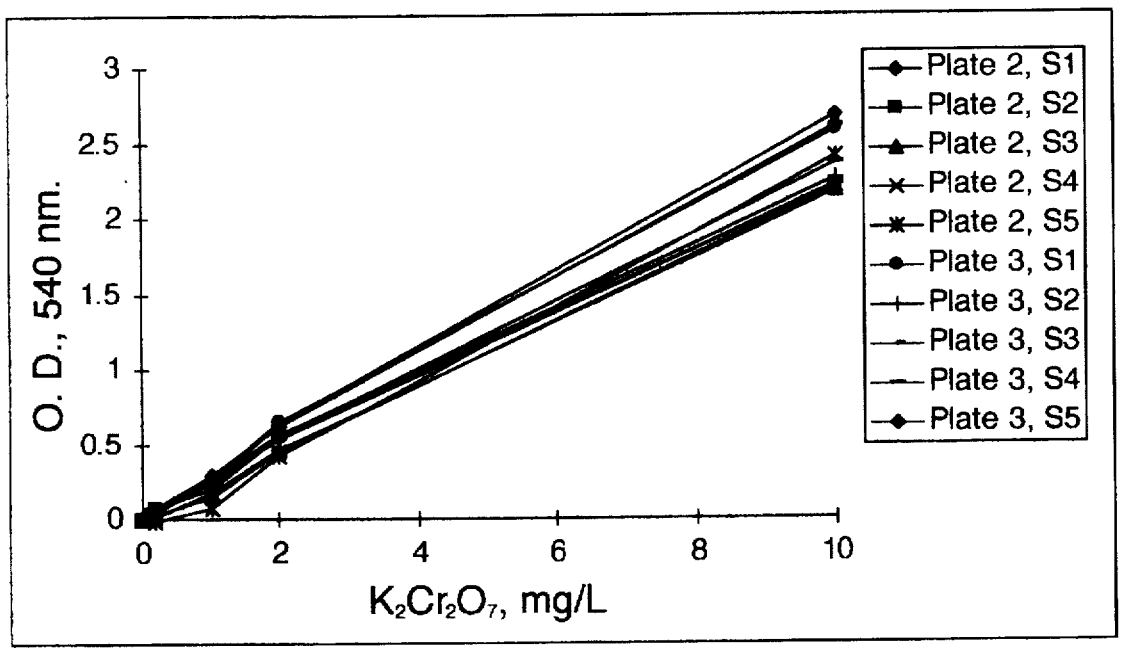
FIG. 8 shows the effect of B. subtilis growth phase and cell density on the Microscale Cr(VI) Assays™.

In this experiment, an overnight culture of *B. subtilis* 168 grown in TSB-D was diluted 1:100 with TSB-D. Two hundred microliters of this dilution were placed in two 96-well microtiter plates. At five time points through the growth curve (40, 225, 352, 452 and 1282 minutes after inoculation), as shown in FIG. 8, a Cr(VI) standard curve was performed in a column of the microtiter plate with the growing *B. subtilis* cells. In this assay 20 µl of 5 mg/ml DPC and 60 µl of 10% $H_2SO_4$ were added to each well, incubated for 5 minutes at 32° C., and then read at 540 nm. referenced to 660 nm. The time points in the figure span from early log phase until stationary phase were measured, with the OD at 660 nm. changing over a 100-fold. In FIG. 8, the values shown along the ordinate represent the optical density at 540 nm; the values shown along the abscissa represent the concentration of $K_2Cr_2O_7$ in mg/L. The insert contained within FIG. 8 indicates which samples correspond the ten symbols used. The terms S1–5 refer to samples 1–5, respectively. Samples 1, 2, 3 , 4 and 5 refer to time points of 40, 225, 352, 452 and 1282 minutes after inoculation, respectively.

The two 96-well microtiter plates were treated as follows. For Plate 3, the assay was started immediately after addition of the $K_2Cr_2O_7$, while for Plate 2, the assay was started after a 30 min. incubation with the $K_2Cr_2O_7$. Significantly, no effect of the 30° C. incubation of *B. subtilis* with the $K_2Cr_2O_7$ was observed on the Cr(VI) content.

FIG. 8 shows that growth phase has little effect on the Cr(VI) microassay. Thus, neither the cell density nor the growth phase were found to significantly interfere with the assay system.

EXAMPLE 6

In this example, the Microscale Cr(VI) Assay™ was performed on two 96-well microtiter plates in Trays 2 and 3, using the method CRASS2P1. Tray 1 contains the reagents for the assay. Tray 1A has an empty two column quarter module. Tray 1B has a two-column quarter module (Beckman, Cat. No. 372788) containing 5 mg/ml of diphernylcarbazide (DPC) (Sigma) dissolved in acetone (such as HPLC reagent acetone, Baker, N.J.) in the left column, A3, and 10% vol./vol. $H_2SO_4$ in the right column, A4. Trays 1C and 1D have empty single-well quarter modules (Beckman, Cat. No. 372790).

The method first used the photometry tool to measure the optical density of the 96-well microtiter plate at Tray 2 at 660 nm. to quantify cell density. These data were stored in data file CR2660 with a unique identifier and printed. The photometry tool was then used to measure the optical density of the 96-well microtiter plate at Tray 3 at 660 nm. to quantify cell density. These data were stored in data file CR3660 with a unique identifier and printed. The photometry tool then measured the optical density of the 96-well microtiter plate at Tray 2 at 540 nm., referenced to 660 nm., to use as a blank for the subsequent Cr(VI) assay. These data were stored in data file CR2REF with a unique identifier and printed. The photometry tool was then used to measure the optical density of the 96-well microtiter plate at Tray 3 at 540 nm., referenced to 660 nm., to use as a blank for the subsequent Cr(VI) assay. These data were stored in data file CR3REF with a unique identifier and printed.

Next, the MP20 tool added 20 μl of DPC from Tray 1A, well A3, to each well of the 96-well microtiter plate in Tray 2, changed tips, and added 20 μl of DPC from Tray 1A, well A3, to each well of the 96-well microtiter plate in Tray 3. The MP200 tool next added 60 μl of 10% $H_2SO_4$ from Tray 1A, well A4, to each well of the 96-well microtiter plate in Tray 2, changed tips, and added 60 μl of 10% $H_2SO_4$ from Tray 1A, well A4, to each well of the 96-well microtiter plate in Tray 3. The method then paused for four minutes to allow the complexation color development caused by the DPC complexing with Cr(VI) to develop.

The photometry tool measured the optical density of the 96-well microtiter plate at Tray 2 at 540 nm., referenced to 660 nm., to quantify the Cr.(VI) assay. These data were stored in data file CR2ASS with a unique identifier and printed. The photometry tool finally measured the optical density of the 96-well microtiter plate at Tray 3 at 540 nm. referenced to 660 nm., to quantify the Cr(VI) assay. These data were stored in data file CR3ASS with a unique identifier and printed.

EXAMPLE 7

In this example, the Microscale Cr(VI) Assay™, was performed on two 96-well microtiter plates containing samples suspected of containing Cr(VI) in Trays 2 and 3. The method, designated as "CRAS2PL1," a modification of the CRASS2P1 method, was used to facilitate use of a square-well titer plate to contain the assay reagents. The square-well plate is resistant to acetone (the solvent for DPC), and can also be sealed to prevent evaporative losses. Tray 1 contained a 2 ml square-well microtiter plate, with reagents for the Microscale Cr(VI) Assays™. Column 5 in this tray contained 5 mg/ml of DPC dissolved in acetone; column 7 contained 10% $H_2SO_4$, which was used with the 96-well microtiter plate in Tray 2; and column 8 contained 10% $H_2SO_4$, which was used with 96-well microtiter plate in Tray 3.

The method first used the photometry tool to measure the optical density at 660 nm. of the 96-well microtiter plate at Tray 2 to quantify cell density. These data were stored in data file CR2660 with a unique identifier and printed. The photometry tool was then used to measure the optical density at 660 nm. of the 96-well microtiter plate at Tray 3 to quantify cell density. These data were stored in data file CR3660 with a unique identifier and printed. Next, the photometry tool was used to produce a blank for Tray 2 in the subsequent Cr(VI) assay, by measuring the optical density at 540 nm., referenced to 660 nm., of the 96-well microtiter plate at Tray 2. These data were stored in data file CR2REF with a unique identifier and printed. A blank was also produced for Tray 3 in the subsequent Cr(VI) assay, by measuring the optical density at 540 nm., referenced to 660 nm., of the 96-well microtiter plate at Tray 3. These data were stored in data file CR3REF with a unique identifier and printed.

The MP20 tool added 20 μl of DPC from column 5 of the square-well titer plate at Tray 1 to each well of the 96-well microtiter plate in Tray 2, changed tips, and added 20 μl of DPC from column 5 of the square-well titer plate at Tray 1 to each well of the 96-well microtiter plate in Tray 3.

Then, the MP200 tool added 60 μl of 10% $H_2SO_4$ from column 7 of the square-well titer plate at Tray 1 to each well of the 96-well microtiter plate in Tray 2, changed tips, and added 60 μl of 10% $H_2SO_4$ from column 8 of the square-well titer plate at Tray 1 to each well of the 96-well microtiter plate in Tray 3.

The method then paused for four minutes to allow the complexation color development caused by the DPC complexing with Cr(VI) to develop. The photometry tool then measured the optical density of the 96-well microtiter plate at Tray 2 at 540 nm. referenced to 660 nm. to quantify the Cr(VI) assay. The data were stored in data file CR2ASS with a unique identifier and printed.

The photometry tool then measured the optical density of the 96-well microtiter plate at Tray 3 at 540 nm. referenced to 660 nm. to quantify the Cr(VI) assay. The data were stored in data file CR3ASS with a unique identifier and printed.

EXAMPLE 8

In this example, the BioMek method CRAS2DIL is described for testing diluted and undiluted samples for Cr(VI) content with the Microscale Cr(VI) Assay™. The source 96-well microtiter plate containing the samples to be diluted was placed in Tray 2 and an empty 96-well microtiter plate was placed in Tray 3. Tray 1 contained a 2 ml square-well titer plate with reagents for the Microscale Cr(VI) Assay™, with column five containing 5 mg/ml of DPC dissolved in acetone, and column 7 containing 10% $H_2SO_4$ used with the 96-well microtiter plate in Tray 2 and column 8 containing 10% $H_2SO_4$ used with 96-well microtiter plate in Tray 3.

The first subroutine, 190Bulk1, used the 8-channel bulk dispense tool to add 190 μl of high purity water from the bulk dispense reservoir into the wells of the empty 96-well microtiter plate in Tray 3.

The second subroutine, 10P2TO31, used the MP20 tool to transfer 10 μl from a 96-well microtiter plate in Tray 2 containing the undiluted sample into the 96-well microtiter plate containing 190 μl of water in Tray 3, and mixed in Tray 3. Tray 3 now holds the diluted samples.

The third subroutine, CRAS2DIL, performed a version of the Microscale Cr(VI) Assay™ on both 96-well microtiter plates. The CRAS2DIL subroutine used the MP20 tool to add 20 μl of DPC from column 5 of the square-well titer plate at Tray 1 to each well of the 96-well microtiter plate in Tray 2, changed tips, and added 20 μl of DPC from column 5 of the square-well titer plate at Tray 1 to each well of the 96-well microtiter plate in Tray 3.

The MP200 tool next added 60 μl of 10% $H_2SO_4$ from column 7 of the square-well titer plate at Tray 1 to each well of the 96-well microtiter plate in Tray 2, changed tips, and added 60 μl of 10% $H_2SO_4$ from column 8 of the square-well titer plate at Tray 1 to each well of the 96-well microtiter plate in Tray 3. The method then paused for four minutes to allow the complexation color development caused by the DPC complexing with Cr(VI) to develop.

The photometry tool then measured the optical density of the 96-well microtiter plate at Tray 2 at 540 nm. referenced to 660 nm. to quantify the Cr(VI) assay. These data were stored in data file CRCONASS with a unique identifier and printed. The photometry tool then measured the optical density of the 96-well microtiter plate at Tray 3 at 540 nm. referenced to 660 nm. to quantify the Cr(VI) assay. These data were stored in data file CR1TO10 with a unique identifier and printed.

EXAMPLE 9

This example demonstrates the automation of growth curve determinations on the BioMek. In an initial experiment, stationary phase cultures grown in TSB-D were manually diluted 1:100 into 5 ml of TSB-D in a test tube and vortexed. The diluted cultures were then carefully transferred to individual troughs of a sterile 8-channel reservoir liner (Costar, Cat. No. 4878). Two hundred microliters of the diluted strains were then inoculated manually into two 96-well microtiter plates using a multichannel pipettor (Rainin, M8, Emeryville, Calif.), with one strain per row (after first transferring into the first 8 wells in a row of 12, the 8-channel pipettor was used with only 4 tips to complete the row of 12). The inoculated 96-well microtiter plates were placed in Trays 2 and 3 and the BioMek method 2PLOD660 was run. This method measured the optical density at 660 nm. of each well in the two plates every 15 min for 20 hours of elapsed time.

FIG. 9 shows part of the growth curves for seven microorganisms in TSB-D. In FIG. 9, the values shown along the ordinate represent the optical density at 660 nm; the values shown along the abscissa represent time in minutes. The insert contained within FIG. 9 indicates the symbols used to represent the results obtained with the media control and the following seven microorganisms: Biolog strains 1185, 2708, 2717, 3033, 3083, 3278 and 3851. The strains were all grown in 96-well microtiter plates and the optical density monitored by the BioMek. Each strain shows characteristic differences in lag times and growth rates, while the media control shows no growth. The data for each curve shown in FIG. 9 are from single wells.

One drawback of in this experiment was noted. Because the 96-well microtiter plates were incubated without their lids, the volumes per well decreased from an initial volume of 200 μl to around 90 μl.

This example shows the successful implementation of a microbial growth assay on the BioMek 1000 using 96-well microtiter plates and the automatic measurement of 192 growth curves. In addition, by using a robotic system, additions of media, additional chemicals, such as contaminants, dilutions to model fed-batch reactors, or other manipulations are possible. The microbial growth assay developed permits the application of microbial physiology tools to discover and optimize bioremediation processes.

EXAMPLE 10

The development of the microbial growth assay entailed developing, improving, and automating inoculation methods; controlling physiological conditions, including temperature, moisture, and volume; tuning and standardizing the experimental setup; and improving and standardizing the data analysis system. In order to improve the temperature control and the isolation of the cultures, a temperature controlled, HEPA-filtered chamber was designed as described in this example. While a commercial laminar flow hood in a temperature regulated room could be used, a custom, inexpensive chamber was designed to contain the BioMek. The chamber was built of wood with plexiglas sides and doors. A HEPA filter unit (Honeywell Environmental Air Control, Inc., Hagerstown, Md., Enviracaire Model No. 13531) was used in the chamber to filter and circulate air through a plenum. Temperature control was provided by a thermostat that controlled a low wattage incandescent light and provided a chamber temperature of 32° C. The chamber was also humidified to reduce evaporative losses. The chamber significantly reduced noise from the robot and shielded the operator from both microbial aerosols and chemical exposure.

However, the increased temperature of the chamber and the air flow resulted in an unwanted side effect of increased evaporation rates and decreased uniformity. This was critical because 96-well microtiter plates were typically used without covers in the microbial growth experiments and because the media would completely evaporate in about 10 hours in the chamber. In addition to limiting the portion of the growth curve that could be measured, the evaporation also meant that the concentration of growth media and, more importantly, Cr(VI) would be increasing as the experiment progressed. Finally, the pattern of evaporation was not uniform.

To counteract the evaporative losses, three measures were taken to tune the system. First, the fan speed of the HEPA unit was reduced by a speed controller; this greatly decreased the overall evaporation rate. Second, the plenum was modified to move most of the air flow away from where plates are incubated in Tray 2 and 3. This improved uniformity. Finally, sterile water was periodically added by the BioMek to balance the evaporative losses. The combined results of the three measures which took several months of effort, is that volume changes for 96-well microtiter plates are controlled and minimized, with variations of less than 15%.

BioMek growth curve methods for both single and dual growth plates were written that measured the growth period over a 20 hour period and that were optimized for evaporation control. Several different versions of the growth assay software (e.g., 2PL660V8, 2PL660V10, and 2PL66AS1) exist to handle the different requirements of experiments, with varying intervals between O.D. measurements, sources of water for evaporation control (i.e., bulk dispensing container, 2 ml square-well titer plate, and quarter plate reservoirs) and varying end actions, such as performing the Microscale Cr(VI) Assay™. These methods were described in the section software implementation.

EXAMPLE 11

The impact of contaminants on the growth of microorganisms has important implications on any bioremediation process. For Cr(VI), information about the effect of $K_2Cr_2O_7$ on growth and the level of Cr(VI) resistance was gathered either as stand-alone growth experiments or in experiments where the impact of the microorganisms on Cr(VI) levels was also measured.

In one example, the format of the 96-well microtiter plates was standardized by filling 96-well microtiter plates on the BioMek in batches using the BioMek method CRRES001. For each row, wells 1 to 5 are controls for growth in growth medium, such as TSB-D, without Cr(VI) addition, and wells 6 to 12 are used for the Cr(VI) resistance and detoxification curves. The Cr(VI) concentrations used initially were 0, 0.5, 0.1, 0.5, 1, 5, 10, and 50 mg/l of $K_2Cr_2O_7$ in media, while other experiments used other ranges such as 10, 50, 100, 150, 200, 250, and 500 mg/l of $K_2Cr_2O_7$.

In many of the experiments, eight cultures were grown in each 96-well microtiter plate, with one culture per row. Using two 96-well microtiter plates per experiment, 16 strains can be screened in each experiment and the impact of a range of target contaminant. In some initial experiments, one row in each 96-well microtiter plate was used as an internal control and contained B. subtilis 168, while in other experiments, one row was left uninoculated to test cross-well contamination.

Figure 10:
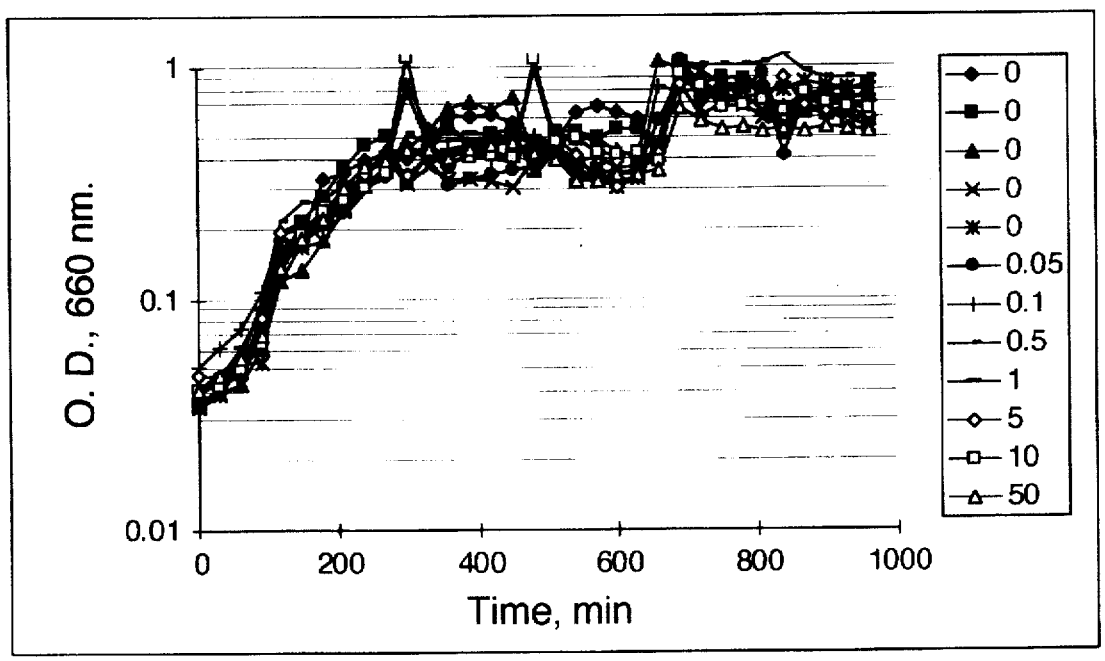
FIG. 10 shows the effect of $K_2Cr_2O_7$ on the growth of O. anthropi.
Figure 11:
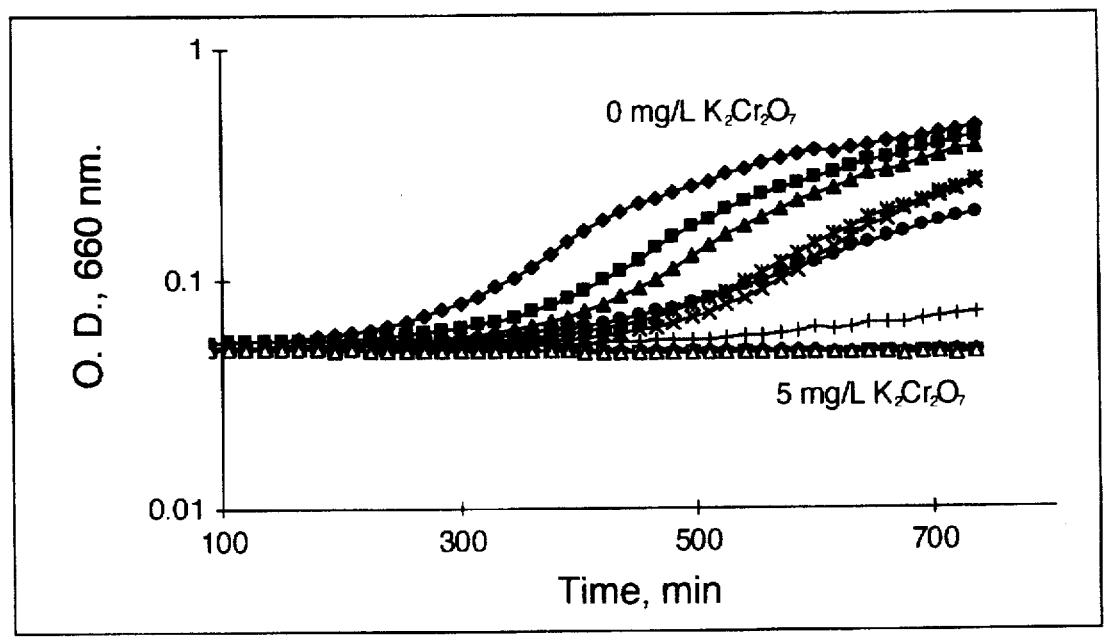
FIG. 11 shows the effect of $K_2Cr_2O_7$ on the growth of B. subtilis.

Most microorganisms grew well in TSB-D at $K_2Cr_2O_7$ concentrations of 10 mg/l $K_2Cr_2O_7$ or less. For example, FIG. 10 shows the minimal effect of $K_2Cr_2O_7$ on the growth curves of B. subtilis 168. No $K_2Cr_2O$-dependent inhibition of logarithmic growth was observed with this organism. The minimal impact of $K_2Cr_2O_7$ on B. subtilis 168 was typical of the results found with the 70 Biolog strains screened. In FIG. 10, the values shown along the ordinate represent the optical density at 660 nm; the values shown along the abscissa represent time in minutes. The insert contained within FIG. 10 indicates the symbols used to represent the results obtained when B. subtilis 168 was grown in the presence of either 0 (five replicates shown), 0.05, 0.1, 0.5, 1.0, 5, 10 or 50 mg/l $K_2Cr_2O_7$. Each curve in this figure is from single wells of the 96-well microtiter plate. An exception was O. anthropi as in this experiment, its growth was impacted by 0.5 mg/l $K_2Cr_2O_7$, and inhibited by 5 mg/l $K_2Cr_2O_7$ (see e.g., FIG. 11) In FIG. 11, the growth curves generated by the growth of O. anthropi in 0 and approximately 0.45, 0.9, 1.35, 1.8, 2.25, 2.7, 3.15, 3.6, 4.05, 4.5 or 5.0 mg//l $K_2Cr_2O_7$ are show by lines containing solid diamonds, solid squares, solid triangles, "x's," "x's" with vertical slashes, circles, vertical slashes, rectangles, long, small rectangles, small diamonds, small squares, and boxes.

EXAMPLE 12

As manual inoculation procedures were found to be time-consuming and a major source of variation in well-to well results in 96-well microtiter plates, an automated inoculation system was developed as described, in this example. In addition, the number of manipulations made tracking the strains a significant issue. To solve these problems, a set of standardized inoculation procedures was devised using the BioMek 1000. An overview of these procedures are shown in FIG. 4.

In these experiments, frozen stocks of organisms (listed in Table 1) were manually inoculated into the wells of 24-well plates containing approximately 2 ml TSB-D. All of these strains had been streaked for isolation on TSA plates, and incubated at 32° C. overnight, with the exception that B. stearothermophilus was incubated at 55° C. Single colonies of these organisms were then aseptically transferred to TSB, and grown under the same time and temperature conditions as the TSA plates. Two frozen stock cultures were made for each strain by adding glycerol to the broth cultures, at a final concentration of 10% vol./vol, or adding 15 µl dimethylsulfoxide per 750 µl of culture, and freezing the cultures at –40° C.

After inoculation into the 24-well plates, the cultures were incubated overnight (i.e., 12–24 hours). Using one of many inoculation methods (e.g., INOCSQV0, INOCSQV5), the overnight cultures were then mixed by the BioMek 1000 seven times in 24-well plates, and 200 µl were added to 1.5 ml of TSB-D into the wells of a 2 ml square-well titer plate. The diluted culture was then mixed seven times by the BioMek and further diluted 1:10 into 200 µl of TSB-D per well (with the inclusion of target contaminant as desired), in a 96-well microtiter plate, with each strain using one row.

BioMek inoculation methods were developed to inoculate from various formats, including 24-well plates to 24-well plates, and 16 wells of a 24-well to 2 columns of a 96-well 2 ml square-well plate, using a variety of standardized patterns for the 24-well source, and from the 2 columns of a 96-well Beckman square well to two 96-well microtiter plates (e.g., INOC96V1).

These sets of inoculation methods permitted the complete automation of the process of strain manipulation after the initial manual inoculation of 24-well plates from frozen stocks. In addition, inoculation by the BioMek decreased the variability found with manual inoculation.

EXAMPLE 13

To increase throughput and minimize manual intervention, a standardized BioMek 1000 screening of microbial strains was devised that combined the microbial growth assay with the Microscale Cr(VI) Assay™ as described.

This was accomplished in either of two ways. First, by running a microbial growth curve method (e.g., 2PL660V8), or 2PL66V10), and then running a Microscale Cr(VI) Assay™ method (e.g., CRASS2P1 or CRASDIL2). An alternative combined method was developed (2PL66AS1) as described in the next Example.

The standardized screen measured the growth rates of strains in growth media, their sensitivity to $K_2Cr_2O_7$, and their detoxification of Cr(VI). The microbial growth assay was usually performed with a range of seven $K_2Cr_2O_7$ concentrations in TSB-D. Both the growth rates of the strains and the effects of Cr(VI) on their growth were determined. At the end of the 20 h microbial growth assay, the microtiter plates were assayed by the Microscale Cr(VI) Assay™ as an end-point assay; this assay measures the Cr(VI) concentration and, therefore, any changes in Cr(VI) concentration caused by the reduction, binding, or other removal of Cr(VI) by the microorganisms.

The setup for the experiment included, for the labware, one position for pipette tips (typically for the MP20 and MP200 pipettors) and three trays. In the embodiment shown in FIG. 2, Trays 2 and 3 had 96-well microtiter plates that were used to grow the microorganisms and perform the Microscale Cr(VI) Assays™. Tray 1 contained a 2 ml square-well titer plate that is used for inoculation and to hold the Microscale Cr(VI) Assay™ reagents. Two columns (columns 1 and 2) of the 2 ml square-well titer plate were used for inoculation, in some experiments, two columns were used for sterile water to control evaporation (columns 11 and 12), and three columns were used for Microscale Cr(VI) Assay™ reagents (columns 5, 7, and 8). Because the DPC reagent was prepared in acetone, the square-well titer plate was sealed with a seal and sample aluminum foil lid (Beckman, Cat. No. 538619) after addition of reagents. The aluminum foil seal was punctured by the pipetting tool at the start of the Microscale Cr(VI) Assay™.

Standardization of the BioMek layout allowed the BioMek routines for the microbial growth assay and the Microscale Cr(VI) Assay™ to be linked together to create the BioMek method 2PL66AS1. Running 2PL66AS1 resulted in a completely automated, standardized screening experiment that measured growth and Cr(VI) resistance curves of 192 wells of microorganisms in two 96-well microtiter plates for 20 hours and then ends with 192 Microscale Cr(VI) assays.

The format of the 96-well microtiter plates was also standardized by manufacturing the plates on the BioMek in batches using the BioMek method CRRES001. For each row, 5 wells are controls for growth in growth medium (e.g., TSB-D) without Cr(VI) addition, and 7 wells are used for the Cr(VI) resistance and detoxification curves. The Cr(VI) concentrations used initially were 0.05, 0.1, 0.5, 1, 5, 10, and 50 mg/l of $K_2Cr_2O_7$ in media, while other experiments used other ranges of such as 10, 50, 100, 150, 200, 250, and 500 mg/l of $K_2Cr_2O_7$.

Figure 12:
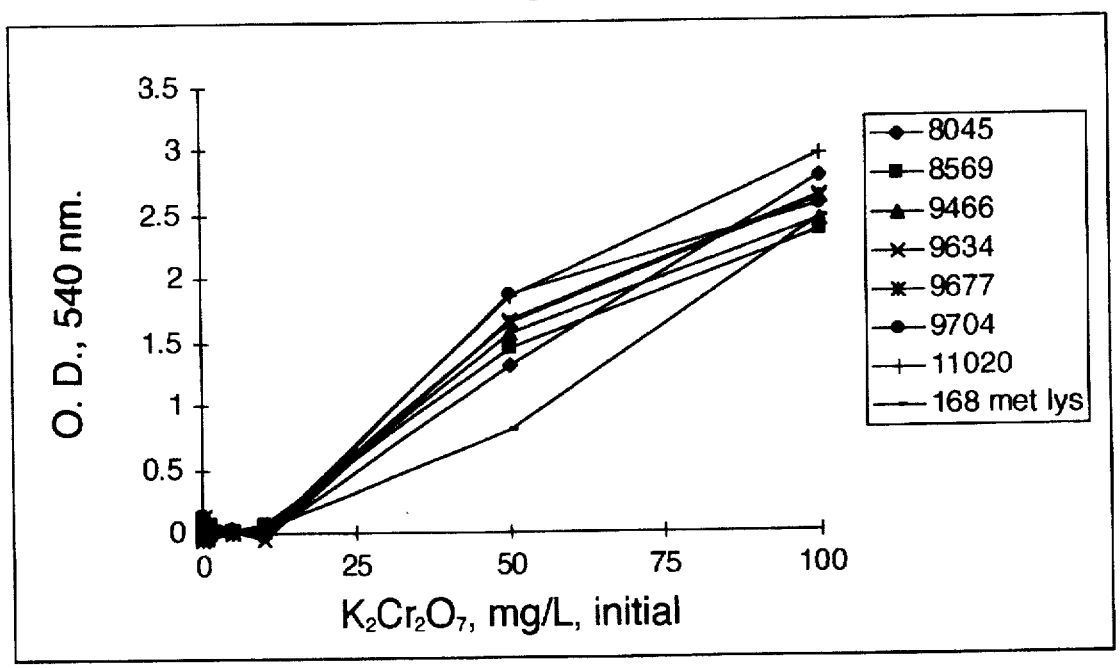
FIG. 12 shows Cr(VI) detoxification by eight organisms.

The result from screening one 96-well plate with eight strains is shown in FIG. 12. In FIG. 12, the values shown along the ordinate represent the optical density at 540 nm; the values shown along the abscissa represent the concentration of $K_2Cr_2O_7$ in mg/L. The insert contained within FIG. 12 indicates the symbols used to represent the results generated using Biolog strains 8045, 8569, 9466, 9634, 9677, 9704, 11020 and *B. subtilis* 168.

The development of a standardized automated screen and plate format allowed the development of a standard data analysis procedure and data storage templates. This was critical because robots, such as the BioMek, produce large amounts of data. The growth curves generated by the BioMek typically contain 3,456 optical density measurements (36 measurements @ for 96-wells) for each plate or 6,912 per two plate experiment. Without a standardized data analysis system, assisted by macros and data analysis templates, the rate limiting step becomes data analysis.

For each screening experiment, four sets of data were gathered for each plate in a run of 2PL66AS1:

1. O.D. at 660 nm. for the growth curves
2. O.D. at 660 nm. immediately before the Cr(VI) assay (for the combined assay this data is redundant with the last OD reading.)
3. O.D. at 540 nm. (referenced to 660 nm.) immediately before the Cr(VI) assay
4. O.D. at 540 nm. (referenced to 660 nm.) after the Cr(VI) assay and development of the color.

The growth curve data for each plate was first appended into one file on the IBM PC that controls the BioMek 1000, saved onto a floppy disk, and then moved to another computer where it was parsed in Excel (Microsoft) from the ASCII strings generated in the BioMek files. The parsed data was then moved into a data analysis template spreadsheet that was setup to regroup the data, with data from each row of the 96-well microtiter plate gathered together in order of the elapsed time. The regrouped data were then ready to be analyzed as desired by Excel (Microsoft) statistical functions, such as least-squares fit or ANOVA, and plotted on a chart template.

For the Microscale Cr(VI) Assay™ data, data analysis templates were designed to hold the data for each plate in an Excel workbook. The workbook had a summary spreadsheet that automatically subtracts the blank data (i.e., "3" in the above list) from the assay data (i.e., "4" in the above list) and generates a plot. Thus, the main manual task involved pasting the data into the workbook in the appropriate data sheets, and entering strain names and concentrations of Cr(VI) used in the experiment. The analysis, plotting, and printing of the 192 Cr(VI) assays from an experiment was typically finished in less than one hour.

EXAMPLE 14

In this example, the growth of microorganisms in two 96-well microtiter plates was quantitated, and the Microscale Cr(VI) Assay™ performed, using the method 2PL66AS1. The two 96-well microtiter plates were placed in Trays 2 and 3, and contained microorganisms in growth media that has a range of concentration of the target chemical. The plates were typically filled with TSB-D, by the utility routine CRRES001, containing a range of target chemical concentrations, and then inoculated with microorganisms listed in Table 1 below, by one of the inoculation methods described above. Some experiments used $K_2Cr_2O_7$ at 0.05, 0.1, 0.5, 1, 5, 10, and 50 mg/l concentrations, while other used 0.5, 1, 5, 10, 50, 100, and 500 mg/l of $K_2Cr_2O_7$, or other ranges.

The first subroutine, 2PL660V9, measured the growth curves of the two 96-well microtiter plates using the photometry tool. At 45 min intervals, the optical density of microorganisms at 660 nm. was measured for the 96-well microtiter plates at Trays 2 and 3. The elapsed time was approximately 20 hours. Following completion of the experiment, the data were transferred to a floppy disk and analyzed in a spreadsheet (for example, Excel by Microsoft) to generate growth curves for all 192 wells.

The 2PL660V9 subroutine contained two nested loops. The outer loop was executed four times, and in each execution added 45 μl of sterile water using the 8-channel bulk dispense tool to each 96-well microtiter plate at trays 2 and 3, approximately every 3 hr. The inner loop was executed six times for each execution of the outer loop. The inner loop contained two functions. The first function read the optical density at 660 nm. of the 96-well microtiter plate at Tray 2 and stored the data in the file PL2660 with a unique trailer. The second function read the optical density at 660 nm. of the 96-well microtiter plate at Tray 3 and stored the data in the file PL3660 with a unique trailer. After reading the optical density of both plates, the loop paused for 45 minutes.

The Microscale Cr(VI) Assay™ portion of the method was performed by the CRAS2PL1 subroutine on the two 96-well microtiter plates in Trays 2 and 3, as described in previous examples.

The 2PL66AS1 is a totally automated method for performing growth curves on 192 wells, and then performing 192 Microscale Cr(VI) assays. Thus, it demonstrates the feasibility of automating the screening of microorganisms for detoxification of environmental pollutants.

EXAMPLE 15

In addition, for use as a screening method, the results must be reproducible. Thus, experiments were conducted to determine whether the methods were indeed reproducible.

Figure 13:
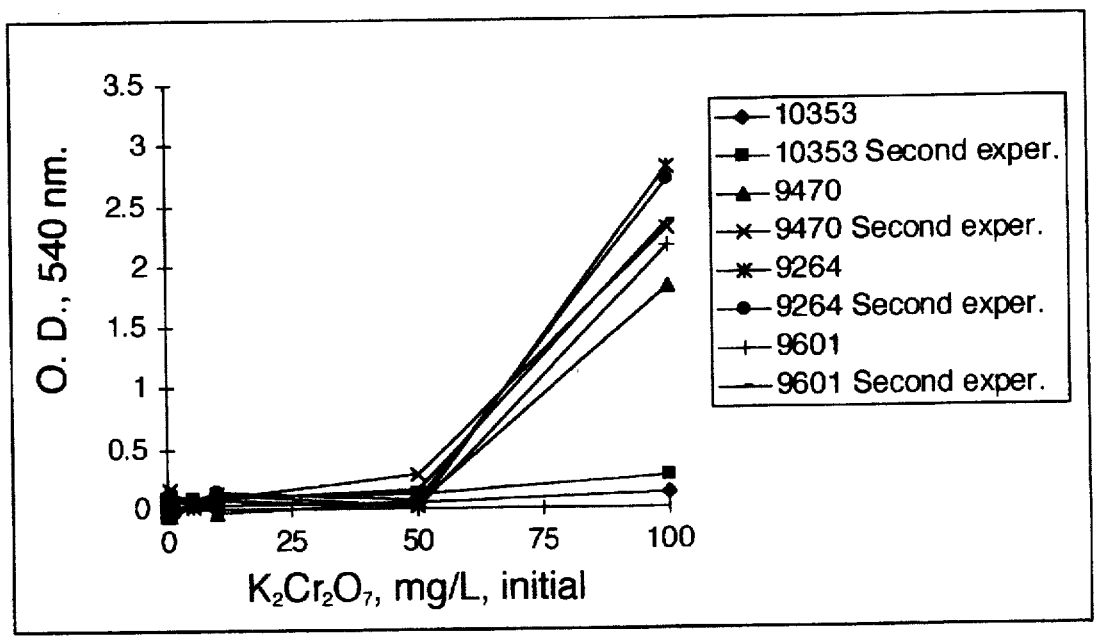
FIG. 13 shows the reproducibility of the method.

In one pair of experiments, identical tests were repeated six days apart to test reproducibility. Fresh overnight cultures were grown in TSB-D in 24-well microtiter plates. The BioMek method INOCSQV4 was used to transfer strains from the 24-well microtiter plate to columns 1 and 2 of a 2 ml square-well microtiter plate containing 1.5 ml TSB-D, with mixing at the source and destination. Method INOC96V1 was then used to inoculate two 96-well microtiter plates that had been made using CRRES001 and various concentrations of $K_2Cr_2O_7$ (0.0, 0.01, 0.5, 1, 5, 10, 50 and 100 mg/l) in TSB. The growth curve method 2PL660V8 was then run in order to perform the microbial growth curves. After completion of the growth curves, the Microscale Cr(VI) Assay™ method, CRAS2P1, was run. The results are shown in FIG. 13. In FIG. 13, the values shown along the ordinate represent the optical density at 540 nm; the values shown along the abscissa represent the initial concentration of $K_2Cr_2O_7$ in mg/l. The insert contained within FIG. 13 indicates the symbols used to represent the results generated using Biolog strains 10353, 9470, 9264 and 9601; the results from two separate experiments are shown for each of the listed strains.

FIG. 13 demonstrates that very similar results are obtained when two identical experiments were performed. Even though the results were repeatable, when strains gave good reductions in Cr(VI) concentration, they were routinely rescreened to eliminate any false positives.

EXAMPLE 16

In this set of experiments, a high-throughput, automated system to screen microorganisms for Cr(VI) detoxification was applied to screen 70 stains from the Biolog culture collection. The screening used the automated inoculation methods with a standardized BioMek method, such as 2PL66AS1, to determine the growth rate, Cr(VI) resistance, and Cr(VI) detoxification of 16 strains.

The resulting high-throughput screening system using the BioMek 1000 was applied to screen 70 phylogenetically diverse strains from the Biolog culture collection (see Table 1 for a list of the strains). The strains with the best Cr(VI) detoxification characteristics were then further screened and the physiology studied as detailed in Examples 18 and 19. An additional 178 strains isolated from the intertidal region of a marine site that is contaminated with chromium were also screened is also included in Example 17.

The screening typically used either the growth curve methods, 2PL660V8 or 2PL66V10, with the CRASS2P1 Microscale Cr(VI) Assay™ method, or the integrated method 2PL66AS1 was used. As described in previous examples, automated inoculation methods were used, including INOCSQV0, INOCSQV2, INOCSQV3, and INOCSQV5, as well as other equivalent methods that used different sets of 24-well microtiter plate wells as sources of inocula.

The inoculation methods were as described in previous examples and in the section describing implementation of software (i.e., inoculation sources of 200 μl of a TSB-D overnight culture in a 24-well microtiter plate to 1.5 ml of TSB-D in a 2 ml square-well microtiter plate in Tray 1. INOC96V1 was then used to inoculate two 96-well microtiter plates that had been prepared with a range of $K_2Cr_2O_7$ concentrations in TSB-D, using the CRRES001 method. Typically, the concentration of $K_2Cr_2O_7$ was 0.05, 0.1, 0.5, 1, 5, 10 and 50 mg/l in initial screening experiments, but this was increased to 0.1, 0.5, 1, 5, 10, 50, and 100 mg/l of $K_2Cr_2O_7$ in TSB-D in later experiments, as strains that detoxified higher levels of Cr(VI) were discovered.

The results of this screening validated the screening system by finding microorganisms previously reported in the literature to reduce Cr(VI) to Cr(III). In addition, the screening of the Biolog collection identified microorganisms that have previously undescribed Cr(VI) detoxification capabilities. Finally, the data from this screening provides a library of the capabilities of microorganisms to detoxify Cr(VI).

The Biolog strains (Table 1) were selected to be as phylogenetically diverse as possible, except that the bacilli were intentionally over-represented.

Figure 14:
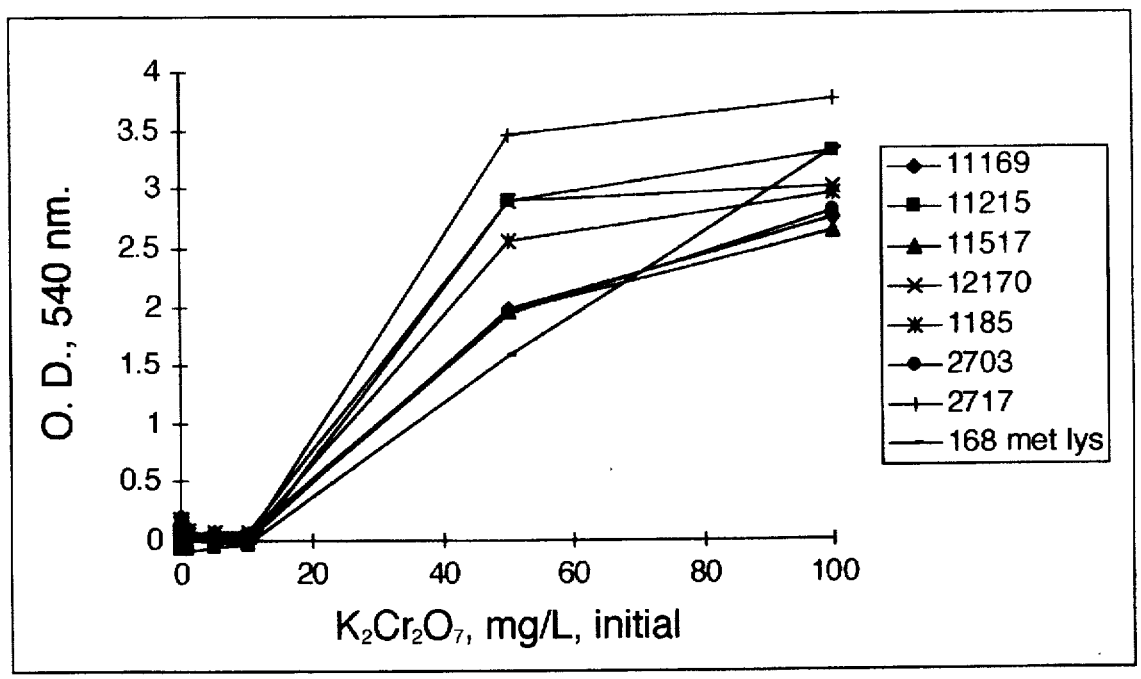
FIG. 14 shows a 96-well microtiter plate where the microorganisms had very little effect on detoxifing $K_2Cr_2O_7$ present in an initial concentration of 50 mg/l.
Figure 15:
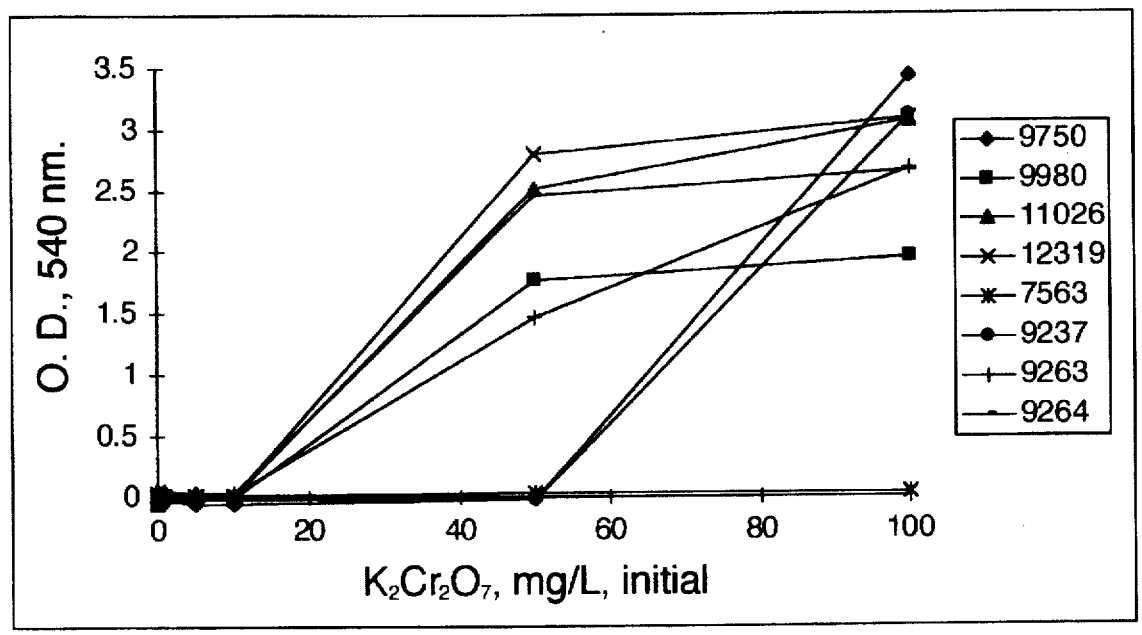
FIG. 15 shows the kinetics of the removal of 10 mg/l of $K_2Cr_2O_7$ by various organisms.

FIGS. 14 and 15 show the Microscale Cr(VI) Assay™ results for two plates in this screening experiment. FIG. 14 shows a 96-well microtiter plate where the microorganisms had very little effect on decreasing Cr(VI) concentrations at the 50 mg/l level, while FIG. 15 shows a plate that has two strains that completely reduce Cr(VI) at 50 mg/l of $K_2Cr_2O_7$, probably by reducing it to Cr(III). In FIGS. 14 and 15, the values shown along the ordinate represent the optical density at 540 nm; the values shown along the abscissa represent the initial concentration of $K_2Cr_2O_7$ in mg/L. The insert contained within FIG. 14 indicates the symbols used to represent the results generated using Biolog strains 11169, 11215, 11517, 12170, 1185, 2703, 2717 and *B. subtilis* 168. The insert contained within FIG. 15 indicates the symbols used to represent the results generated using Biolog strains 9750, 9980, 11026, 12319, 7563, 9237, 9263 and 9264.

All of the strains screened in this example were able to completely reduce 10 mg/l of Cr(VI) during the 20 hour incubation period. Interestingly, at 50 and 100 mg/l in this incubation time the strains start to show considerable heterogeneity. Thus, it is contemplated that the screening method of the present invention will include an initial screen with two wells per strain screened, in which one well contains TSB without added $K_2Cr_2O_7$, and the second with 50 mg/l of $K_2Cr_2O_7$ in TSB.

Of the 70 Biolog strains tested, strains were found that completely removed 100 mg/l of $K_2Cr_2O_7$ using the standardized screening experiment. Sixteen strains, including ones that completely reduced 100 mg/l of $K_2Cr_2O_7$ were identified as "passing" the screen. The "passing" organisms were: *Acidovorax facilis, Bacillus circulans, Aeromonas hydrophila* DNA group 1, *Bacillus firmus* (2 strains), *Aeromonas salmonicida ss achromogenes, Bacillus laevolacticus, Hydrogenophaga flava, Bacillus mycoides, Pseudomonas aeruginosa, Bacillus subtilis* (2 strains), *Pseudomonas diminuta, Cellulomonas flavigena,* and *Enterococcus saccharolyticus*. These organisms were further studied and screened at higher concentrations of $K_2Cr_2O_7$ under different physiological conditions, as described in Example 18 below.

Interestingly, this screen identified two Aeromonas species, two *B. subtilis* strains, and two Pseudomonas species as reducing Cr(VI). In addition, as well as seven bacilli were identified as having excellent Cr(VI) reduction capabilities, and several other bacilli were ranked just under the cutoff for passing this screen.

The confirmation of strains previously reported to detoxify Cr(VI) validated the screening system and demonstrates that the robotic approach can confirm and extend data gathered manually. In addition, the screening gave similar results for two pairs of strains that are of the same genus (*B. subtilis* and *Bacillus firmus*). When coupled with the facts that both species of Aeromonas and Pseudomonas were found to detoxify Cr(VI) in this system, this suggests that the robotic screening system is reproducible, and well-suited to large-scale screening efforts.

Of particular interest, the screening also identified four genera that have not been reported to reduce Cr(VI), namely, *Acidovorax facilis, Hydrogenophaga flava, Cellulomonas flavigena,* and *Enterococcus saccharolyticus.* It is contemplated that these organisms will be useful for bioremediation field application.

Based on this Example, it is apparent that the ability to identify strains with novel Cr(VI) detoxification abilities can be extended by screening a much larger collection of known strains and by screening isolates from Cr(VI) contaminated sites.

EXAMPLE 17

In this example, isolates from a Cr(VI)-contaminated site were tested in the screening method and equipment of the present invention. It was hypothesized that isolates from contaminated sites may be resistant to the contaminants at the site and may have favorable bioremediation traits useful in remediating the site. The ability to reduce or remove Cr(VI) from solution was directly compared for isolates from a Cr(VI) contaminated site and the "passing" strains identified in the previous Example.

Samples of the sandy beach area were collected from the intertidal region of a chromium contaminated site bordering San Francisco Bay. Analysis for total chromium showed 199 mg/l in the samples. Bacteria were isolated from the samples by washing them with a solution of 200 mM NaCl in water and then various dilutions ($10^0$, $10^{-2}$, $10^{-4}$, and $10^{-6}$) were plated onto TSA (Difco) with 200 mM NaCl added. The plates were incubated for 8 days at room temperature.

After growth, 175 single colonies were picked from the $10^{-2}$ plate, and placed directly into wells of two 96-well microtiter plates containing TSB with 200 mM NaCl. The 16 "passing" strains from the previous example were also placed into wells (G9–G12 and H1–H12) of one of the 96-well microtiter plates. In addition, 200 µl of an unpurified sample from the wash buffer were added to the remaining well. The two 96-well microtiter plates were incubated at 32° C. overnight, and the method INCOPY96 was used to inoculate two fresh 96-well microtiter plates that contained 200 µl TSB containing 200 mM NaCl and 50 mg/l of $K_2Cr_2O_7$.

The plates were grown on the BioMek with the optical density monitored over the approximately 20-hour incubation period using the method 2PL660V10, and assayed by the Microscale Cr(VI) Assay™ with CRAS2DL1.

Figure 16:
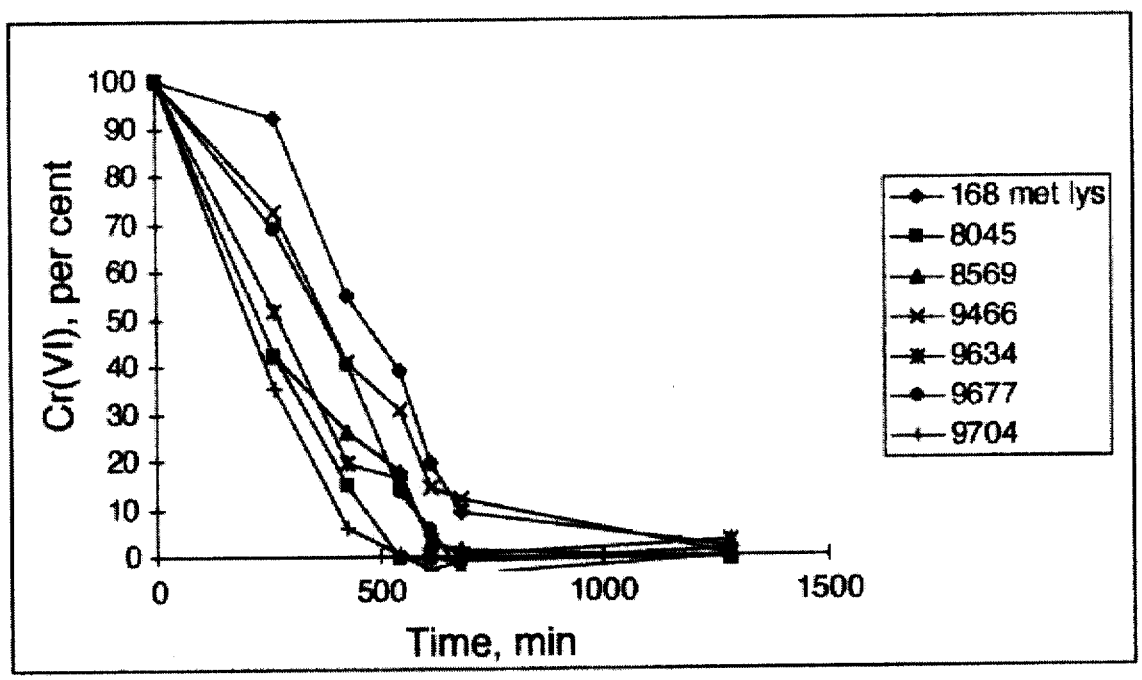
FIG. 16 shows a plate that has two strains that completely reduce Cr(VI) present at an initial concentration of 50 mg/l of $K_2Cr_2O_7$.

FIG. 16 shows the results for the 196-wells. In FIG. 16, the values shown along the ordinate represent per cent Cr(VI); the values shown along the abscissa represent time in minutes. The insert contained within FIG. 16 indicates the symbols used to represent the results generated using *B. subtilis* 168 (168 met lys) and Biolog strains 8045, 8569, 9466, 9634, 9677, and 9704.

Figure 17:
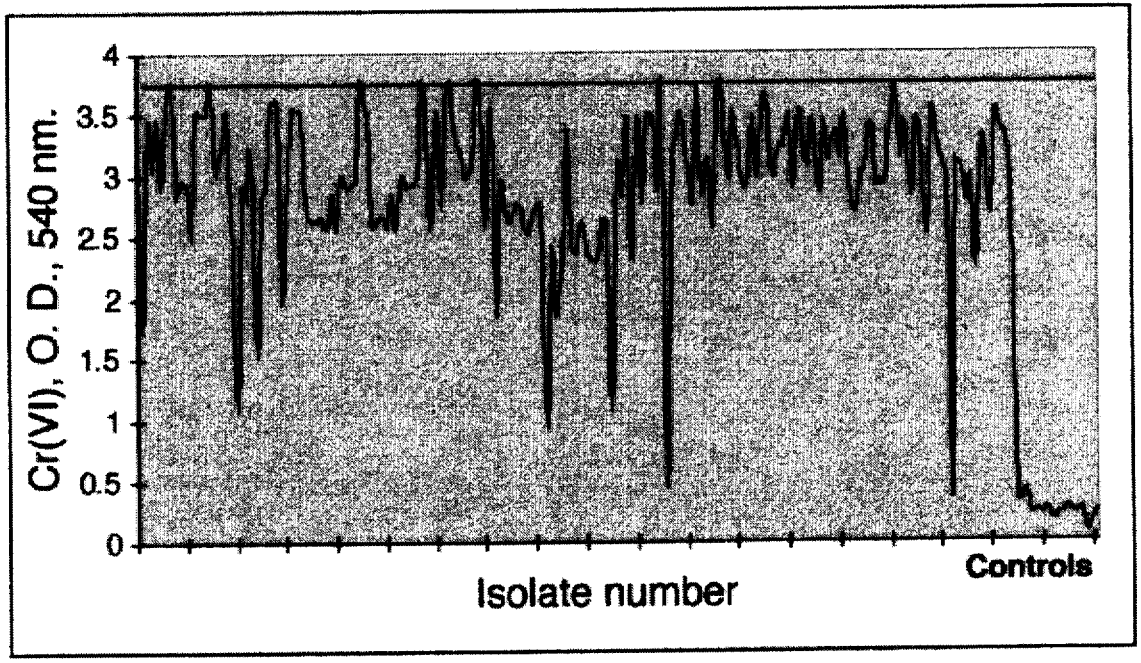
FIG. 17 shows the results obtained with 178 environmental isolates and 16 stock cultures.

The control for the TSB-D at 50 mg/l of $K_2Cr_2O_7$ after incubation and the Microscale Cr(VI) Assay™ was determined to be 3.75 $OD_{540}$ units. Surprisingly, only 2 of the 178 isolates from the site reduced the $K_2Cr_2O_7$ to less than 0.5 OD units, but all of the 16 Biolog strains used in Example 16 (shown as the last strains in the right of FIG. 17) exceeded this result. The results demonstrate that the approach can be applied to screen strains from contaminated sites.

EXAMPLE 18

In this example, some of the physiological conditions for Cr(VI) detoxification were investigated, in order to determine the optimal conditions for the screening process. This was important, as the robotic system can also be applied to optimize bioremediation processes before scale-up, treatability studies, and field application.

A major physiological variable is the source of carbon and energy source. However, the initial screening of the Biolog strains was done in TSB-D, which does not contain added dextrose.

For this example, a series of experiments was performed to compare Cr(VI) detoxification in TSB with detoxification in TSB, to test whether dextrose affected Cr(VI) detoxification. The only difference between these commercially available media is the inclusion of 2.5 g Bacto-Dextrose in TSB, per liter of media. The 16 Biolog strains that passed the initial screening were tested. In these experiments, two and three day old stock cultures grown in TSB-D were inoculated manually from 24-well microtiter plates by adding 200 µl of culture into 1.5 ml of TSB-D in a 2 ml square well microtiter plate. The INOC96V1 method was then run to inoculate two 96-well microtiter plate that had been filled by CRRES001 with 200 µl of 0, 10, 50, 100, 150, 200, 250, and 500 mg/l of $K_2Cr_2O_7$ in TSB or TSB-D. For one experiment, the method 2PL66AS1 was then run to perform the growth assays and Microscale Cr(VI) Assays™. Because the level of Cr(VI) remaining was outside of the linear range for Cr(VI), the next experiment used the 2PL66V10 growth method and the CRAS2DIL Microscale Cr(VI) Assay™ method, which assays undiluted as well as 1:20 dilutions, was used.

Figure 18:
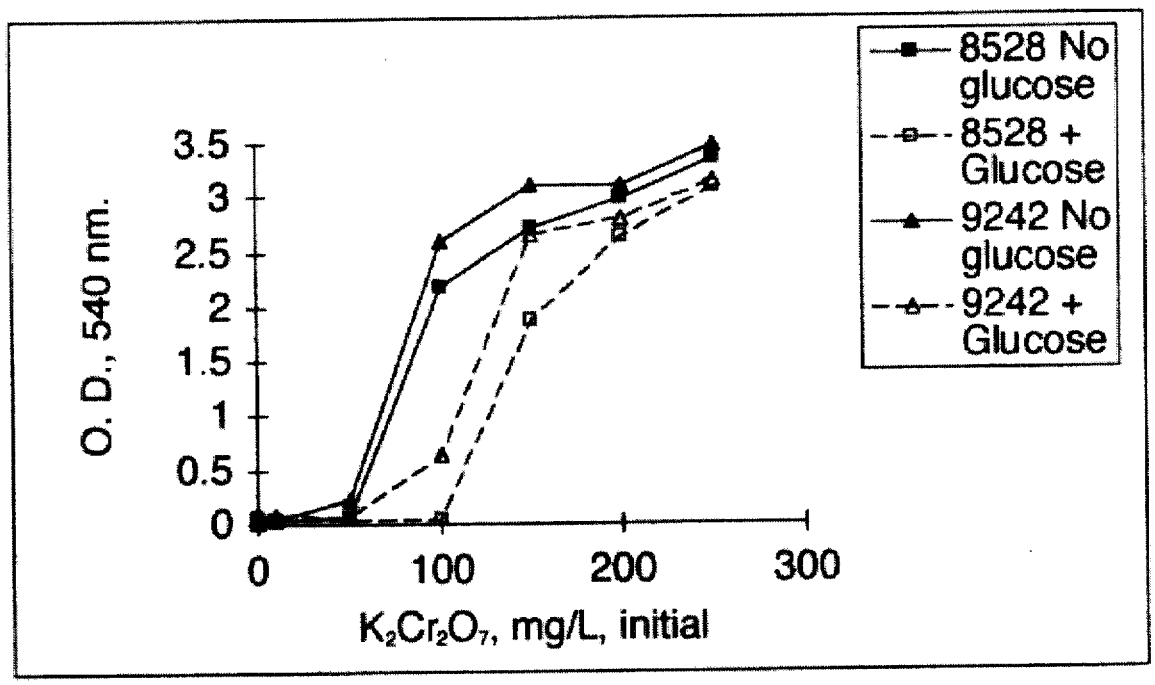
FIG. 18 shows the effect of glucose addition on Cr(VI) detoxification.

The results of this experiment indicated that glucose addition generally improved the range of $K_2Cr_2O_7$ concentrations that could be detoxified by the microorganisms. FIG. 18 shows two strains where the range of $K_2Cr_2O_7$ concentrations where Cr(VI) was completely removed by the microbial activity increased from about 50 mg/l to around 100 mg/l. For Biolog strain 8528, the improved detoxification is still evident at concentrations exceeding 150 mg/l (FIG. 18). In FIG. 18, the values shown along the ordinate represent the optical density at 540 nm; the values shown along the abscissa represent the initial concentration of $K_2Cr_2O_7$ in mg/L. The insert contained within FIG. 18 indicates the symbols used to represent the results obtained using Biolog strain 8528 without glucose, strain 8528 with glucose, strain 9242 without glucose and strain 9242 with glucose. These results are typical of the effects of glucose on the strains tested. Thus, the results suggest that glucose addition may improve the reduction of Cr(VI) to Cr(III), and further suggest that a more extensive study of the impact of energy source would be fruitful.

One approach that is contemplated is to use plates with a variety of different conditions, such as energy source, carbon source, nitrogen source, sulfur source, electron acceptor, etc. By adding $K_2Cr_2O_7$ screening strains with a robotic system, the impact of different conditions on a bioremediation capability for a target chemical, such as the removal of Cr(VI) from the media, could be determined. This would provide considerable insight into what the optimal condition for bioremediation of the target chemical and might also provide insight into the metabolic switches that regulate its detoxification.

EXAMPLE 19

In this experiment, the kinetics of Cr(VI) reduction were investigated. To optimize the rates of a bioremediation process, it was important to measure the kinetic rate constants of the process, as this measurement is important in the application of microbial physiology and biochemistry to the bioremediation field.

It was hypothesized that the high-throughput, speed, and accuracy of a robotic system offered an ideal system to measure rates of reaction and ultimately to determine $V_{max}$ and $K_M$ values. In this experiment, the growth rates and time course of Cr(VI) reduction were measured for eight bacterial strains (*B. subtilis* 168, #8045, #8569, #9466, #9634, #9677, and #9704), at eight concentrations of $K_2Cr_2O_7$ (0.0, 0.05, 0.5, 1, 5, 10, and 50 mg/l). The experiment was performed in a semi-automatic mode, with the BioMek 1000 filling and inoculating twelve 96-well microtiter plates, measuring all of the microbial growth assay data, and performing the Microscale Cr(VI) Assay™, but in this case the BioMek was "fed" manually. This semi-automatic mode of operation resulted in an approximately ten-fold increase in throughput for this embodiment. Ten of the twelve plates were filled using the BioMek method CRRES001 with TSB-D in columns 1–5 and 0.0, 0.05, 0.1, 0.5, 1, 5, 10, and 50 mg/l of $K_2Cr_2O_7$ in TSB-D in columns 6–12, and then identically inoculated with one strain per row. Thus, there were 10 identical plates containing one strain per row and $K_2Cr_2O_7$ concentrations ranging from 0 to 50 mg/l.

After inoculation, the plates were incubated at 32° C., and the growth monitored by the BioMek 1000. At various times (0, 246, 426, 547, 615, 682, and 1283 minutes), whole plates were assayed for microbial growth and for Cr(VI) concentrations. FIG. 16 shows the results for 10 mg/l of $K_2Cr_2O_7$. The experiment also generated curves for the six other concentrations of $K_2Cr_2O_7$ and the no $K_2Cr_2O_7$ control. In this Figure, each data point was from a single well of a 96-well microtiter plate, and the data for each time point was from a different plate-thus the seven time points were from seven different plates. While all the eight strains eventually reduce the 10 mg/l of $K_2Cr_2O_7$, the strains show considerable differences in the rate of reduction. At 50 mg/l, the strains differentiated themselves into two groups that cluster into early and late logarithmic phase reduction of Cr(VI). Thus, FIG. 16 demonstrates the feasibility of measuring kinetics of bioremediation processes with the BioMek 1000. Thus, the method of the present invention is suitable to determine the initial rates of detoxification, as well as the Michaelis-Menton kinetic rate parameters, $V_{max}$ and $K_M$, and then used to quantify the impact of changes in physiological and environmental conditions on the detoxification rates.

EXAMPLE 20

Figure 19:
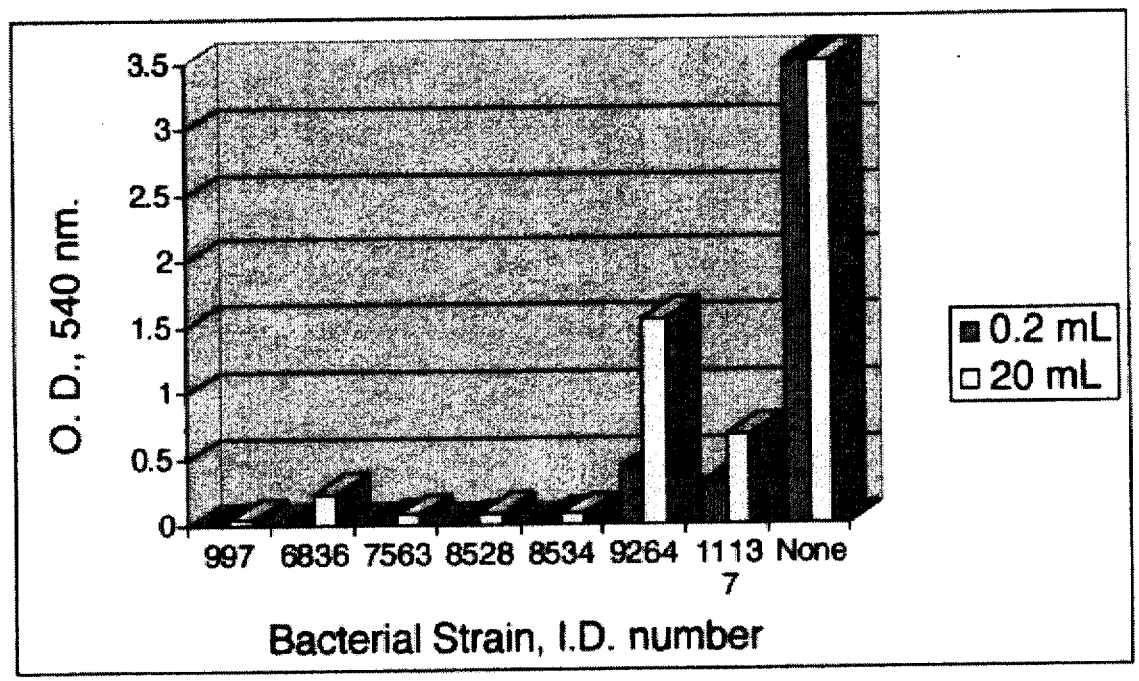
FIG. 19 shows a comparison of the results obtained with scaling volumes from 200 μl to 20 ml.
Figure 20:
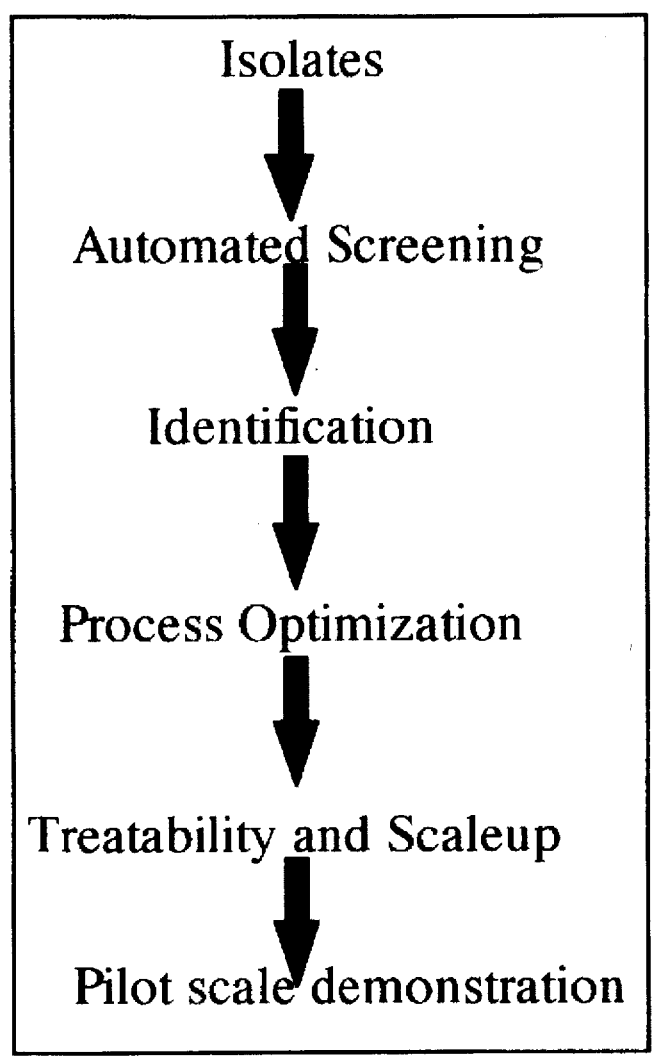
FIG. 20 shows an approach to develop specific bioremediation processes.

In this experiment, volume scale-up from 200 µl to larger volumes was investigated to determine if the results obtained in the 200 µl volumes in 96-well microtiter plate would scaleup to larger volumes and other geometries. A Cr(VI) detoxification experiment was designed using a 100-fold range of volumes of 200 µl and 20 ml. The 200 µl volumes were in 96-well microtiter plates and the 20 ml volumes in 250 ml beakers. Overnight cultures were grown in TSB (Difco) with 50 mg/l $K_2Cr_2O_7$, and were used to inoculate TSB at 1:100 for both volumes. For the cultures in 96-well microtiter plates, 8 wells per strain were inoculated. All the cultures were grown without shaking in the same 32° C. incubator. After 21 hours of incubation, 200 µl aliquots were added to a 96-well microtiter plate in quadruplicate and the CRAS2PL1 method run, to assay the Cr(VI) level remaining in the wells. The results are shown in FIG. 19. In FIG. 19, the values shown along the ordinate represent the optical density at 540 nm. The Biolog strain numbers are listed along the abscissa; growth seen in the 0.2 ml cultures is shown using shaded bars for each strain; growth seen in the 20 ml cultures is shown using open bars for each strain listed.

FIG. 19 shows that the 0.2 ml and 20 ml cultures showed similar results except for strain 9264. FIG. 19 demonstrates that scaleup by 100-fold was successful for most of the strains. This further validates the use of 96-well microtiter plates in a screen and validates the automated screening system developed on the BioMek.

The above examples demonstrate the suitability of the present invention's robotic screening of microorganisms for bioremediation processes.

APPENDIX

The following appendix includes a step by step description of how the various methods are performed, to better assist in their comprehension.

INOCULATION METHODS
INOC24V1

Setup. Tray 2 holds a 24-well plate containing stock microbial strains, Tray 3 holds an uninoculated 24-well plate that contains growth media. Pipette 40 µl from each well of Tray 2 to the corresponding well in Tray 3, changing tips each time.

INOCSQV0
see flow diagram FIG. 21
INOCSQV2
see flow diagram FIG. 22
INOCSQV3
see flow diagram FIG. 23
INOCSQV5

Setup. 24-well microtiter plate with sample cultures in Tray 2. 2 µl deep well microtiter plate in Tray 1 contains TSB-D or other media. Transfer 200 µl as shown below, mixing of 200 µl 7 times at source and 7 times at destination, changing tips each time.

Source at Tray 2 The sample are being transferred in the following manner:

| Source well in Tray 2 | Destination well in Tray 1 |
|---|---|
| A1 | A1 |
| A2 | B1 |
| A3 | C1 |
| A4 | D1 |
| A5 | E1 |
| A6 | F1 |
| B1 | G1 |
| B2 | H1 |
| B3 | A2 |
| B4 | B2 |
| B5 | C2 |
| B6 | D2 |
| C1 | E2 |
| C2 | F2 |
| C3 | G2 |
| C4 | H2 |

INOC96V1

Setup. P250 tips. Tray 1 holds a 2 ml deep-well microtiter plate with microorganisms in columns 1 and 2. Trays 2 and 3 hold 96-well microtiter plate containing growth media (typically 200 µl of TSB-D). Pipette using 20 µl of culture column 1 of the 2 ml deep-well microtiter plate repeatedly to each column of the 96-well microtiter plate in tray 2. Change tips. Pipette using 20 µl of culture from column 2 of the 2 ml deep-well microtiter plate repeatedly to each column of the 96-well microtiter plate in tray 3.

INCOPY96
Setup. P250 tips. Tray 2 holds a 96-well microtiter plate containing stock microbial strains. Tray 3 holds an uninoculated 96-well microtiter plate that contains growth media (typically 190 μl). Pipette 10 μl from each well of Tray 2 to the corresponding well in Tray 3, mixing seven times of 20 μl at both the source and destination plates and changing tips each time.

ASSAY METHODS

---

General microbial growth assays: For use with methods 2PL660V8 & 2PL66V10

---

Setup reagents, tips, tools, reservoirs, and 96-well microtiter plates
Loop
  Loop
    Measure O.D. at 660 nm. of cultures; store data.
    Pause
  Next
  Add water to counterbalance evaporation
Next

---

General Cr(VI) Assay Method: for use with as Adapted for CRAS2PL1 and CRASS2P1

Setup reagents, tips, tools, reservoirs, and 96-well microtiter plates
Measure O.D. at 660 nm. of 96-well microtiter plate at Tray 2; store data.
Measure O.D. at 660 nm. of 96-well microtiter plate at Tray 3; store data.
Measure O.D. at 540 nm. referenced to 660 nm. of 96-well microtiter plate at Tray 2; store data.
Measure O.D. at 540 nm. referenced to 660 nm. of 96-well microtiter plate at Tray 3; store data.
Add 20 μl of DPC to each well of the 96-well microtiter plate in Tray 2.
Changes tips.
Add 20 μl of DPC to each well of the 96-well microtiter plate in Tray 3.
Add 60 μl of 10% $H_2SO_4$ to each well of the 96-well microtiter plate in Tray 2.
Changes tips.
Add 60 μl of 10% $H_2SO_4$ to each well of the 96-well microtiter plate in Tray 3.
Pauses for color development
Measure O.D. at 540 nm. referenced to 660 nm. of 96-well microtiter plate at Tray 2 to quantify the Cr(VI) assay. Store data.
Measure O.D. at 540 nm. referenced to 660 nm. of 96-well microtiter plate at Tray 3 to quantify the Cr(VI) assay. Store data.

CRAS2DIL method
Setup reagents, tips, tools, reservoirs, and 2 96-well microtiter plates. Tray 1 contains a 2 ml deep-well microtiter plate with reagents for the Microscale Cr(VI) Assay™. Tray 2 holds 96-well microtiter plate with samples, Tray 3 holds an empty plate.

---

Run Subrouting 190Bulk2
  Dispense 190 μl of high purity water from the reservoir into 96-well microtiter
    plate in Tray 3.
  Subroutine 10P2TO31.
    Pipette 10 μl from each well of a 96-well microtiter plate in Tray 2 to each well of a 96-well microtiter plate in Tray 3.
    Mixed two times at destination. Mix volume is 20 μl.
  Run Subroutine CRAS2DIL (performs a version of the Microscale Cr(VI) Assay ™ on both
    96-well microtiter plates).
    Add 20 μl of DPC to each well of the 96-well microtiter plate in Tray 2.
    Changes tips.
    Add 20 μl of DPC to each well of the 96-well microtiter plate in Tray 3.
    Add 60 μl of 10% $H_2SO_4$ to each well of the 96-well microtiter plate in Tray 2.
    Changes tips.
    Add 60 μl of 10% H2SO4 to each well of the 96-well microtiter plate in Tray 3.
    Pauses 4 min for color development
    Measure O.D. at 540 nm. referenced to 660 nm. of 96-well microtiter plate at Tray 2 to quantify the Cr(VI) assay. Store data.
    Measure O.D. at 650 nm. referenced to 660 nm. of 96-well microtiter plate at Tray 3 to quantify the Cr(VI) assay. Store data.

---

2PL66AS1 method

---

Run Microbial growth assay
  Setup reagents, tips, tools, 2 ml deep-well microtiter plate, and 96-well microtiter plate
  Loop 4 times.
    Loop 6 times.
      Measure O.D. at 660 nm. of 96-well microtiter plate in Tray 2; store data.
      Measure O.D. at 660 nm. of 96-well microtiter plate in Tray 3; store data.
      Pause 45 min.
    Next
    Adds 45 μl water to each well in Tray 2 and 3 to counterbalance evaporation
  Next
Run Microscale Cr(VI) Assay ™

-continued

Measure O.D. at 660 nm. of 96-well microtiter plate at Tray 2; store data.
Measure O.D. at 660 nm. of 96-well microtiter plate at Tray 3; store data.
Measure O.D. at 540 nm. referenced to 660 nm. of 96-well microtiter plate at Tray 2; store data.
Measure O.D. at 540 nm. referenced to 660 nm. of 96-well microtiter plate at Tray 3; store data.
Adds 20 µl of DPC to each well of the 96-well microtiter plate in Tray 2.
Changes tips.
Add 20 µl of DPC to each well of the 96-well microtiter plate in Tray 3.
Add 60 µl of 10% $H_2SO_4$ to each well of the 96-well microtiter plate in Tray 2.
Changes tips.
Add 60 µl of 10% $H_2SO_4$ to each well of the 96-well microtiter plate in Tray 3.
Pauses for color development
Measure O.D. at 540 nm. referenced to 660 nm. of 96-well microtiter plate at Tray 2 to quantify the Cr(VI) assay. Store data.
Measure O.D. at 540 nm. referenced to 660 nm. of 96-well microtiter plate at Tray 3 to quantify the Cr(VI) assay. Store data.

Utility Methods
CRRES001
Setup reagents, tips, tools, reservoirs. Tray 1 contains four two-column quarter modules with liquid. Trays 2 and 3 hold empty 96-well microtiter plates.
Pipette from left side of module A1 (Tray 1) to first five columns of the 96-well microtiter plate in Tray 2.
Pipette from left side of module A1 (Tray 1) to first five columns of the 96-well minicrotiter plate in Tray 3.
Pipette from right side of module A1 (Tray 1) to column six of the 96-well microtiter plate in Tray 2.
Pipette from left side of module B1 (Tray 1) to column seven of the 96-well microtiter plate in Tray 2.
Pipette from right side of module B1 (Tray 1) to column eight of the 96-well microtiter plate in Tray 2.
Pipette from left side of module C1 (Tray 1) to column nine of the 96-well microtiter plate in Tray 2.
Pipette from right side of module C1 (Tray 1) to column ten of the 96-well microtiter plate in Tray 2.
Pipette from left side of module D1 (Tray 1) to column eleven of the 96-well microtiter plate in Tray 2.
Pipette from right side of module D1 (Tray 1) to column twelve of the 96-well microtiter plate in Tray 2.
Change tips.
Pipette from right side of module A1 (Tray 1) to column six of the 96-well microtiter plate in Tray 3.
Pipette from left side of module B1 (Tray 1) to column seven of the 96-well microtiter plate in Tray 3.
Pipette from right side of module B1 (Tray 1) to column eight of the 96-well microtiter plate in Tray 3.
Pipette from left side of module C1 (Tray 1) to column nine of the 96-well microtiter plate in Tray 3.
Pipette from right side of module C1 (Tray 1) to column ten of the 96-well microtiter plate in Tray 3.
Pipette from left side of module D1 (Tray 1) to column eleven of the 96-well microtiter plate in Tray 3.
Pipette from right side of module D1 (Tray 1) to column twelve of the 96-well microtiter plate in Tray 3.
190Bulk2
Dispense 190 µl of high purity water from the reservoir into 96-well microtiter plate in Tray 3.
20P2TO31
Pipette 20 µl from each well of a 96-well microtiter plate in Tray 2 to each well of a 96-well microtiter plate in Tray 3.
10P2TO32
Pipette 10 µl from each well of a 96-well microtiter plate in Tray 2 to each well of a 96-well microtiter plate in Tray 3.
Mixed two times at destination. Mix volume is 20 µl.

200MP200
Dispense 200 µl from a single well half module at tray 1C into each well of a 96-well microtiter plate at Tray 2.

I claim:

1. An automated method for screening microorganisms capable of detoxifying a compound, comprising the steps of:
   a. providing:
      i. a plurality of samples in a pair of final holders having separate vessels, each final holder separating the samples into said vessels, said samples suspected of containing microorganisms,
      ii. a chemical compound, and
      iii. an automated workstation;
   b. exposing said samples to said chemical compound to form test samples in said final holders; and
   c. performing at least one of a plurality of assay methods on said test samples to generate test output data, wherein said automated workstation performs said assay methods.

2. The method of screening for microorganisms according to claim 1 wherein the step of providing a plurality of samples further comprises the steps of:
   a. providing a sample source in a source holder; and
   b. performing at least one of a plurality of inoculation methods to transfer a portion of said sample to said final holders, wherein said automated workstation performs said inoculation methods.

3. The method of screening for organisms according to claim 2 wherein said inoculation transfer methods, comprise the steps of distributing a portion of said sample from said sample source in said source holder to particular vessels of said pair of final holders in a manner in which creates specific patterns of distribution that said automated workstation maintains in memory and operates to effect said distribution under predetermined conditions.

4. The method of screening microorganisms according to claim 1 wherein the step of providing a chemical compound further comprises the steps of:
   a. providing a chemical source of the chemical compound; and
   b. performing at least one of a plurality of utility transfer methods to transfer said chemical compound to said pair of final holders, wherein said automated workstation performs said utility transfer methods.

5. The method of screening for organisms according to claim 4 wherein said utility transfer methods comprise the steps of distributing a portion of said chemical compound from said chemical source to said pair of final holders in a manner in which creates patterns of distribution that said automated workstation maintains in memory operates under predetermined conditions.

6. The method of screening for microorganisms according to claim 1 wherein said assay methods further comprise the step of detecting changes in the physical condition of said test samples and recording said detected changes to generate output data.

7. The method of screening for microorganisms according to claim 6 further comprising the step of calculating a growth curve based on said detected changes.

8. The method of screening for microorganisms according to claim 1 wherein said chemical compound is chromium.

9. The method of screening for microorganisms according to claim 1 wherein said automated workstation is a BioMek 1000.

10. The method of screening for microorganisms according to claim 1 wherein said plurality of samples is obtained from a contaminated site.

11. The method of screening for microorganisms according to claim 1 wherein said step of exposing said samples to said chemical compound to form test samples in said final holders is carried out so that said samples are exposed to said chemical compound in varying amounts.

12. A method of creating a growth curve while screening for microorganisms capable of detoxifying a compound, comprising the steps of:
   a. i) an automated workstation;
      ii) at least one chemical compound;
      and iii) at least one sample;
   b. measuring the optical density of at least one test sample;
   c. calculating a growth curve for said microorganisms based on said optical density; and
   d. performing operations on said test sample during said calculation step.

13. A method as recited in claim 12, prior to said measuring step, said method comprising the steps of:
   a. providing:
      i. a plurality of samples in a pair of final holders having separate vessels, each final holder separating the samples into said vessels, said samples suspected of containing microorganisms,
      ii. a chemical compound, and
   b. exposing said samples to said chemical compound to form said test samples in said final holders.

14. The method as recited in claim 13 wherein the step of providing a plurality of samples further comprises the steps of:
   a. providing a sample source in a source holder; and
   b. performing at least one of a plurality of inoculation methods to transfer a portion of said sample to said final holders, wherein said automated workstation performs said inoculation methods.

15. The method as recited in claim 14 wherein said inoculation transfer methods, comprise the steps of distributing a portion of said sample from said sample source in said source holder to particular vessels of said pair of final holders in a manner in which creates specific patterns of distribution that said automated workstation maintains in memory and operates to effect said distribution under predetermined conditions.

16. The method of screening microorganisms according to claim 12 wherein the step of providing a chemical compound further comprises the steps of:
   a. providing a chemical source of the chemical compound; and
   b. performing at least one of a plurality of utility transfer methods to transfer said chemical compound to said pair of final holders.

17. The method as recited in claim 16 wherein said utility transfer methods comprise the steps of distributing a portion of said chemical compound from said chemical source to said pair of final holders in a manner in which creates patterns of distribution that said automated workstation maintains in said memory operates to effect under predetermined conditions.

18. The method as recited in claim 12 wherein said chemical compound is chromium.

19. The method as recited in 12 wherein said automated workstation is a BioMek 1000.

20. The method as recited in claim 12 wherein said plurality of samples is obtained from a contaminated site.

21. A method for screening microorganisms capable of detoxifying one or more compounds, comprising the steps of:
   a) providing:
      i) at least one sample suspected of containing said microorganisms; and
      ii) at least one chemical compound; and
      iii) an automated workstation;
   b) exposing said sample to said chemical compound to produce a test sample; and
   c) assaying said test sample for the presence of said chemical compound, wherein said assaying is performed by said automated workstation.

22. The method of claim 21, wherein said chemical compound is chromium.

23. The method of claim 21, wherein said sample is obtained from a contaminated site.

24. The method of claim 21, comprising the further step of providing optimal conditions for detoxification of said chemical compound by said microorganisms.

25. The method of claim 21, wherein said samples are exposed to varying concentrations of said chemical compound.

26. The method of claim 21, wherein said automated workstation is a BioMek 1000.

27. The method of claim 21, wherein said assay methods further comprise the step of detecting changes in the physical condition of said test samples and recording said detected changes to generate output data.

28. A method of creating a growth curve for microorganisms capable of detoxifying a compound, comprising the steps of:
   a) providing:
      i) a sample suspected of containing said microorganisms; and
      ii) at least one chemical compound; and
      iii) an automated workstation;
   b) exposing said sample to said chemical compound to provide a test sample;
   c) measuring the optical density of said test sample to provide an optical density determination, wherein said measuring is performed by said automated workstation; and
   d) calculating a growth curve for said microorganisms from said optical density determination.

29. The method of claim 28, wherein said measuring said growth curve is calculated by said automated workstation.

30. The method of claim 28, wherein said automated workstation is a BioMek 1000.

31. The method of claim 28, wherein said chemical compound is chromium.

32. The method of claim 28, wherein said sample is obtained from a contaminated site.

* * * * *